(12) United States Patent
Lagarias et al.

(10) Patent No.: US 7,795,397 B2
(45) Date of Patent: Sep. 14, 2010

(54) RED AND NEAR INFRARED FLOURESCENT PHYOTOCHROME

(75) Inventors: John Clark Lagarias, Davis, CA (US); Amanda J. Fischer, Davis, CA (US)

(73) Assignee: The Regents of the University of California, Oakland, CA (US)

(*) Notice: Subject to any disclaimer, the term of this patent is extended or adjusted under 35 U.S.C. 154(b) by 693 days.

(21) Appl. No.: 11/123,692

(22) Filed: May 5, 2005

(65) Prior Publication Data

US 2006/0110827 A1 May 25, 2006

Related U.S. Application Data

(60) Provisional application No. 60/569,310, filed on May 6, 2004, provisional application No. 60/598,661, filed on Aug. 3, 2004, provisional application No. 60/640,867, filed on Dec. 30, 2004.

(51) Int. Cl.
*A61K 36/00* (2006.01)
*C12N 5/04* (2006.01)
*C07H 21/04* (2006.01)

(52) U.S. Cl. .................. 530/370; 435/419; 536/23.2

(58) Field of Classification Search ........................ None
See application file for complete search history.

(56) References Cited

U.S. PATENT DOCUMENTS

| | | | |
|---|---|---|---|
| 4,542,104 | A | 9/1985 | Stryer et al. |
| 4,859,528 | A | 8/1989 | Lee et al. |
| 5,268,526 | A | 12/1993 | Hershey et al. |
| 5,538,885 | A | 7/1996 | Hollis et al. |
| 5,639,952 | A | 6/1997 | Quail et al. |
| 5,656,496 | A | 8/1997 | Quail et al. |
| 6,017,734 | A | 1/2000 | Summers et al. |
| 6,046,014 | A | 4/2000 | Lagarias et al. |
| 6,294,714 | B1 | 9/2001 | Matsunaga et al. |
| 6,740,507 | B2 | 5/2004 | Glazer et al. |
| 6,858,429 | B2 | 2/2005 | Quail et al. |
| 6,887,688 | B2 | 5/2005 | Lagarias et al. |
| 6,916,973 | B2 | 7/2005 | Kim et al. |
| 7,005,511 | B2 | 2/2006 | Tsien et al. |
| 7,033,806 | B2 | 4/2006 | Lagarias et al. |
| 7,045,680 | B2 | 5/2006 | Kohichi et al. |
| 7,056,683 | B2 | 6/2006 | Ting |
| 7,060,793 | B2 | 6/2006 | Tsien et al. |
| 7,060,869 | B2 | 6/2006 | Tsien et al. |
| 2004/0009559 | A1 | 1/2004 | Glazer et al. |
| 2004/0014151 | A1 | 1/2004 | Glazer et al. |

OTHER PUBLICATIONS

Chica et al. Curr Opin Biotechnol. Aug. 2005;16(4):378-84.*
Berkelman and Lagarias (1986) "Visualization of Bilin-Linked Peptides and Proteins in Polyacry;amide Gels." *Analytical Biochemistry*, 156: 194-201.

Chiesa et al. (2001) "Recombinant aequorin and green fluorescent protein as valuable tools in the study of cell signalling." *Biochemical Journal*, 355(Part 1): 1-12.
Cubitt et al. (1995) "Understanding, improving and using green fluorescent proteins.". *Trends in Biochemical Sciences*, 20(11): 448-455.
Dorland'S Illlustrated Medical Dictionary (1988), pp. 113, 1362.
Gambetta and Lagarias (2001) "Genetic engineering of phyochrome biosynthesis in bacteria." *Proceedings of the National Academy of Sciences*, USA, 98(19): 10566-10571.
Gil et al. (2000) "Photocontrol of subcellular partitioning of phytochrome-B:GFP fusion protein in tobacco seedlings." *The Plant Journal*, 22(2): 135-145.
Guralnick et al. (1996) "Transport of DNA into the Nuclei of Xanopus Oocytes by a Modified VirE2 Protein of Agrobacterium." *The Plant Cell*, 8: 363-373.
Hailey et al. (2000) "Fluorescence Resonance Energy Transfer Using Color Variants of Green Fluorescent Protein." *Methods in Enzymology*, 351: 34-49.
Halliday et al. (1999) "POC1 : An *Arabidopsis* mutant perturbed in phytochrome signaling because of aT DNA insertion in the promoter of PIF3, a gene encoding a phytochrome-interacting bHLH protein." *Proceedings of the National Academy of Sciences*, USA, 96(10): 5832-5837.
Heim and Tsien (1996) "Engineering green fluorescent protein for improved brightness, longer wavelengths and fluorescence resonance energy transfer." *Current Biology*, 6: 178-182.
Hisada et al. (2000) "Light-Induced Nuclear Translocation of Endogenous Pea Phytochrome A Visualized by Immunocytochemical Procedures." *The Plant Cell*, 12: 1063-1078.
Kim et al. (2000) "Light-induced nuclear import of phytochrome-A:GFP fusion proteins is differentially regulated in transgenic tobacco and *Arabidopsis*." *The Plant Journal*, 22(2): 125-133.
Kircher et al. (1999) "Light Quality-Dependent Nuclear Import of the Plant Photoreceptors Phytochrome A and B." *The Plant Cell*, 11: 1145-1156.
Kosugi et al. (2002) "Interactions of the *Arabidopsis* E2F and DP Proteins Confers Their Concomitant Nuclear Translocation and Transactivation." *Plant Physiology*, 128: 833-843.
Laemmli (1970) "Cleavage of Structural Proteins during the Assembly of the Head Bacteriophage T4." *Nature*, 227: 680-685.
Lagarias and Lagarias (1989) "Self-assembly of synthetic phytochrome holoprotein in vitro." *Proceedings of the National Academy of Sciences*, USA, 86(15): 5778-5780.
Lamparter et al. (2002) "Phytochrome from *Agrobacterium tumefaciens* has unusual spectral properties and reveals an N-terminal chromophore attachment site." *Proceedings of the National Academy of Sciences*, USA, 99(18): 11628-11633.
Li and Lagarias (1994) "Phytochrome assembly in living cells of the yeast *Saccharomyces cerevisiae*." *Proceedings of the National Academy of Sciences*, USA, 91(26): 12535-12539.
Lin et al. Sequence Listing Search Result, 2003, p. 1.
Martínez-García et al. (2000) "Cirect Targeting of Light Signals to a Promoter Element-Bound Transcription Factor." *Science*, 288: 859-863.

(Continued)

*Primary Examiner*—Christian L Fronda
(74) *Attorney, Agent, or Firm*—Weaver Austin Villeneuve & Sampson LLP; Tom Hunter

(57) ABSTRACT

This invention provides fluorescent adducts that emit in the far red and/or near infrared. In certain embodiments, the adducts comprise a mutant apoprotein and a bilin.

11 Claims, 25 Drawing Sheets

OTHER PUBLICATIONS

Matz et al. (1999) "Fluorescent proteins from nonbioluminescent *Anthozoa* species." *Nature Biotechnology*, 17(10): 969-973.

Murphy and Lagarias (1997) "The Phyofluors: a new class of fluorescent protein probes." *Current Biology*, 7: 870-876.

Nagatani (1997) "Spatial Distribution of Pytochromes." *Journal of Plant Research*, 110: 123-130.

Nagy and Schäfer (1999) "Control of nuclear import and phytochromes." *Trends in Plant Science*, 4(4): 125-126.

Nagy and Schäfer (2000) "Nuclear and cytosolic events of light-induced, phytochrome-regulated signaling in higher plants." *EMBO Journal*, 19(2): 157-163.

Nagy and Schäfer (2000) "Phytochromes, pif3 and light signalling go nuclear." *Current Opinion in Plant Biology*, 3: 450-454.

Nagy et al. (2000) "Nucleo-cytoplasmic partitioning of the plant photoreceptors phytochromes." *Seminars in Cell & Development Biology*, 11: 505-510.

Ni et al. (1998) "PIF3, a Phytochrome-Interacting Factor Necessary for Normal Photinduced Signal Transduction, Is a Novel Basic Helix-Loop-Helix Protein." *Cell*, 95: 657-667.

Ni et al. (1999) "Binding of phytochrome B to its nuclear signalling partner PIF3 is reversibly induced by light." *Nature*, 400: 781-784.

Sakamoto and Nagatani (1996) "Nuclear localization activity of phytochrome B." *The Plant Journal*, 10(5): 859-868.

Shimizu-Sato et al. (2002) "A light-switchable gene promoter system." *Nature Biotechnology*, 20(10): 1041-1044.

Taiz et al. (1998) "Phytochrome." Chapter 17, *Plant Physiology* 2.sup.nd Ed. Sinauer Associates, Inc. Publishers, p. 483-488.

Terry and Lagarias (1991) "Holophytochrome Assembly." *The Journal of Biological Chemistry*, 266(33): 22215-22221.

White ((1973) Prinicples of Biochemistry, McGraw-Hill, Inc. p. 215.

Yamaguchi et al. (1999) "Light-dependant Translocation of a Phytochrome B-GFP Fusion Protein to the Nucleus in Transgenic *Arabidopsis*." *The Journal of Cell Biology*, 145(3): 437-445.

Zhang et al. (2002) "Creating New Fluorescent Probes For Cell Biology." *Nature Reviews Molecular Cell Biology*, 3(12): 906-918.

Zhu et al. (2000) "Phytochrome B binds with greater apparent affinity thatn phytochrome A to the basic helix-loop-helidx factor PIF3 in a reaction requiring the PAS domain of PIF3" *Proceedings of the National Academy of Sciences*, USA, 97(24): 13419-13424.

\* cited by examiner

```
ATGGCCACCACCGTACAACTCAGCGACCAATCCCTCCGTCAGCTAGAAACCC
TCGCCATCCACACCGCCCACCTGATTCAGCCCCACGGTTTAGTGGTGGTCCT
GCAGGAACCAGACCTCACCATCAGCCAAATTAGCACCAACTGCACCGGCATT
TTAGGGCGATCGCCAGAGGATTTGTTGGGCAGAACCCTAGGGGAAGTGTTTG
ATAGCTTTCAGATTGATCCCATCCAGAGTCGCCTAACGGCCGGACAAATCAG
CAGCCTCAACCCCAGTAAACTTTGGGCGCGGGTCATGGGGGACGACTTTGTC
ATTTTTGACGGGGTTTTTCATCGCAACAGTGACGGTTTATTGGTATGTGAAC
TcGAGCCAGCCTACACTTCCGATAATCTGCCCTTCCTCGGTTTTTATCACAT
GGCCAACGCTGCCCTGAATCGGTTGCGCCAACAAGCTAATCTACGGGATTTC
TACGATGTTATTGTCGAAGAAGTCCGCCGTATGACTGGCTTTGACCGGGTGA
TGCTACCGCTTTGATGAAAATAACCACGGTGATGTCATTGCCGAAGATAA
ACGGGATGATATGGAACCCTATTTGGGCCTGCACTATCCCGAATCGGATATT
CCCCAACCCGCCCGTCGGCTATTTATCCACAACCCCATTCGAGTAATTCCCG
ATGTTTATGGTGTGGCGGTGCCCCTGACCCCAGCGGTTAACCCCAGCACCAA
CCGAGCGGTGGATTTAACAGAATCCAATCTGCGCAGTGCGTACCATTGCCAC
TTGACCTATCTGAAAAATATGGGGGTAGGAGCGTCTTTAACCATTTCCCTAA
TTAAGGACGGCCATCTCTGGGGGCTCATTGCCTGCCACCATCAAACCCCCAA
AGTAATTCCCTTTGAACTGCGTAAAGCCTGCGAATTTTTTGGTCGGGTGGTG
TTTAGCAACATTTCCGCCCAGGAAGATACGGAAACCTTCGATTACCGGGTGC
AGcTGGCGGAGCATGAAGCGGTTTTATTGGACAAAATGACCACGGCGGCGGA
TTTTGTCGAAGGATTAACTAATCATCCCGATCGCCTGTTGGGATTAACGGGC
TCCCAGGGGGCGGCCATTTGCTTTGGGGAAAAATTGATTTTAGTAGGGGAAA
CCCCGGACGAGAAAGCAGTGCAATATTTACTGCAATGGTTGGAGAATCGGGA
AGTGCAAGACGTTTTCTTCACCTCTTCCCTCTCACAAATTTATCCTGATGCA
GTGAATTTTAAATCCGTGGCCAGTGGCTTATTGGCCATTCCCATTGCCCGTC
ACAACTTTTTGCTCTGGTTTCGCCCTGAAGTGTTGCAAACGGTTAATTGGGG
CGGTGACCCAAATCATGCTTACGAAGCTACCCAGGAAGACGGTAAAATCGAG
CTCCATCCCCGCCAATCCTTTGACCTCTGGAAAGAATTGTCCGACTCCAAT
CTTTGCCCTGGCAATCGGTGGAAATCCAAAGTGCCCTGGCCCTGAAAAAGGC
GATCGTCAACCTCATTTTGCGCCAGGCAGAAGAA
```

*Fig. 1A*

MATTVQLSDQSLRQLETLAIHTAHLIQPHGLVVVLQEPDLTISQIS
TNCTGILGRSPEDLLGRTLGEVFDSFQIDPIQSRLTAGQISSLNPS
KLWARVMGDDFVIFDGVFHRNSDGLLVCELEPAYTSDNLPFLGFYH
MANAALNRLRQQANLRDFYDVIVEEVRRMTGFDRVMLHRFDENNHG
DVIAEDKRDDMEPYLGLHYPESDIPQPARRLFIHNPIRVIPDVYGV
AVPLTPAVNPSTNRAVDLTESNLRSAYHCHLTYLKNMGVGASLTIS
LIKDGHLWGLIACHHQTPKVIPFELRKACEFFGRVVFSNISAQEDT
ETFDYRVQLAEHEAVLLDKMTTAADFVEGLTNHPDRLLGLTGSQGA
AICFGEKLILVGETPDEKAVQYLLQWLENREVQDVFFTSSLSQIYP
DAVNFKSVASGLLAIPIARHNFLLWFRPEVLQTVNWGGDPNHAYEA
TQEDGKIELHPRQSFDLWKEIVRLQSLPWQSVEIQSALALKKAIVN
LILRQAEE

*Fig. 1B*

```
ATGGCCACCACCGTACAACTCAGCGACCAATCCCTCCGTCAGCTAGAAACCC
TCGCCATCCACACCGCCCACCTGATTCAGCCCCACGGTTTAGTGGTGGTCCT
GCAGGAACCAGACCTCACCATCAGCCAAATTAGCGCCAACTGCACCGGCATT
TTAGGGCGATCGCCAGAGGATTTGTTGGGCAGAACCCTAGGGGAAGTGTTTG
ATAGCTTTCAGATTGATCCCATCCAGAGTCGCCTAACGGCCGGACAAATCAG
CAGCCTCAACCCCAGTAAACTTTGGGCGCGGGTCATGGGGACGACTTTGTC
ATTTTTGACGGGGTTTTTCATCGCAACAGTGACGGTTTATTGGTATGTGAAC
TcGAGCCAGCCTACACTTCCGATAATCTGCCCTTCCTCGGTTTTTATCACAT
GGCCAACGCTGCCCTGAATCGGTTGCGCCAACAAGCTAATCTACGGGATTTC
TACGATGTTATTGTCGAAGAAGTCCGCCGTATGACTGGCTTTGACCGGGTGA
TGCTATACCGCTTTGATGAAAATAACCACGGTGATGTCATTGCCGAAGATAA
ACGGGATGATATGGAACCCTATTTGGGCCTGCACTATCCCGAATCGGATATT
CCCCAACCCGCCCGTCGGCTATTTATCCACAACCCCATTCGAGTAATTCCCG
ATGTTTATGGTGTGGCGGTGCCCCTGACCCCAGCGGTTAACCCCAGCACCAA
CCGAGCGGTGGATTTAACAGAATCCATTCTGCGCAGTGCGTACCATTGCCAC
TTGACCTATCTGAAAAATATGGGGTAGGAGCGTCTTTAACCATTTCCCTAA
TTAAGGACGGCCATCTCTGGGGGCTCATTGCCTGCCACCATCAAACCCCCAA
AGTAATTCCCTTTGAACTGCGTAAAGCCTGCGAATTTTTTGGTCGGGTGGTG
TTTAGCAACATTTCCGCCCAGGAAGATACGGAAACCTTCGATTACCGGGTGC
AGcTGGCGGAGCATGAAGCGGTTTTATTGGACAAAATGACCACGGCGGCGGA
TTTTGTCGAAGGATTAACTAATCATCCCGATCGCCTGTTGGGATTAACGGGC
TCCCAGGGGGCGGCCATTTGCTTTGGGGAAAAATTGATTTTAGTAGGGGAAA
CCCCGGACGAGAAAGCAGTGCAATATTTACTGCAATGGTTGGAGAATCGGGA
AGTGCAAGACGTTTTCTTCACCTCTTCCCTCTCACAAATTTATCCTGATGCA
GTGAATTTTAAATCCGTGGCCAGTGGCTTATTGGCCATTCCCATTGCCCGTC
ACAACTTTTTGCTCTGGTTTCGCCCTGAAGTGTTGCAAACGGTTAATTGGGG
CGGTGACCCAAATCATGCTTACGAAGCTACCCAGGAAGACGGTAAAATCGAG
CTCCATCCCCGCCAATCCTTTGACCTCTGGAAAGAATTGTCCGACTCCAAT
CTTTGCCCTGGCAATCGGTGGAAATCCAAAGTGCCCTGGCCCTGAAAAAGGC
GATCGTCAACCTCATTTTGCGCCAGGCAGAAGAA
```

Fig. 2A

MATTVQLSDQSLRQLETLAIHTAHLIQPHGLVVVLQEPDLTISQIS
ANCTGILGRSPEDLLGRTLGEVFDSFQIDPIQSRLTAGQISSLNPS
KLWARVMGDDFVIFDGVFHRNSDGLLVCELEPAYTSDNLPFLGFYH
MANAALNRLRQQANLRDFYDVIVEEVRRMTGFDRVMLYRFDENNHG
DVIAEDKRDDMEPYLGLHYPESDIPQPARRLFIHNPIRVIPDVYGV
AVPLTPAVNPSTNRAVDLTESILRSAYHCHLTYLKNMGVGASLTIS
LIKDGHLWGLIACHHQTPKVIPFELRKACEFFGRVVFSNISAQEDT
ETFDYRVQLAEHEAVLLDKMTTAADFVEGLTNHPDRLLGLTGSQGA
AICFGEKLILVGETPDEKAVQYLLQWLENREVQDVFFTSSLSQIYP
DAVNFKSVASGLLAIPIARHNFLLWFRPEVLQTVNWGGDPNHAYEA
TQEDGKIELHPRQSFDLWKEIVRLQSLPWQSVEIQSALALKKAIVN
LILRQAEE

*Fig. 2B*

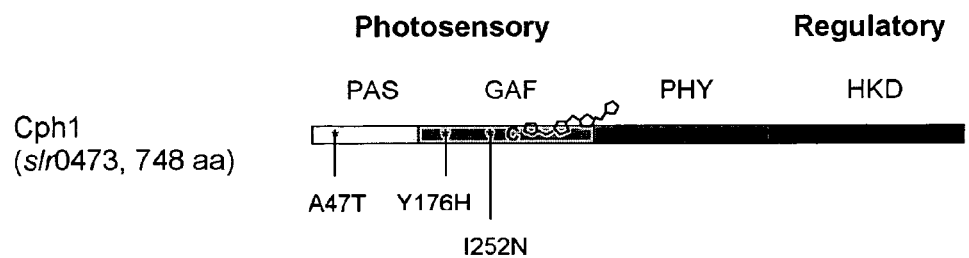

Cph1
(slr0473, 748 aa)

*Fig. 3*

Figure 2S. All Alignments 072404
Phenotypic Class WT: No alteration in Pr/Pfr Abs, max. or photoconversion (25)

Phenotypic Class MI: Pr and Pfr shifted to the blue (17)

Fig. 14

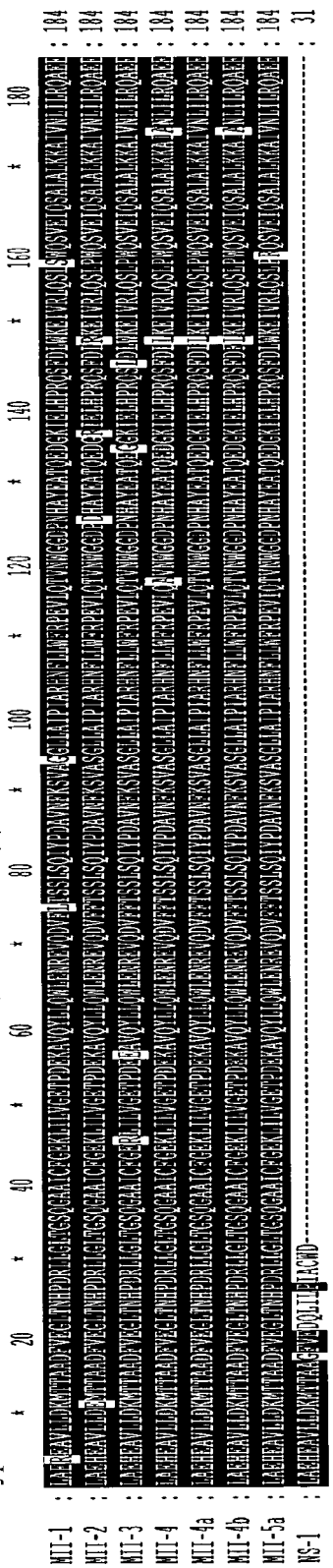
Fig. 14 Cont.

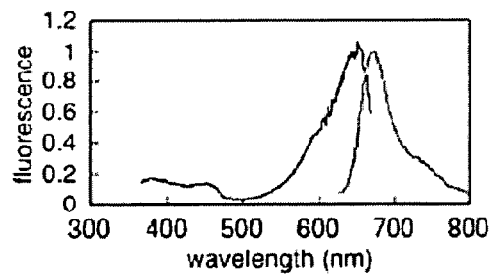
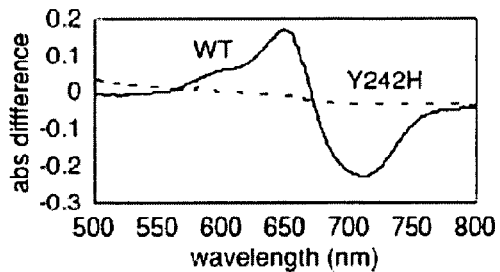
*Fig. 16*
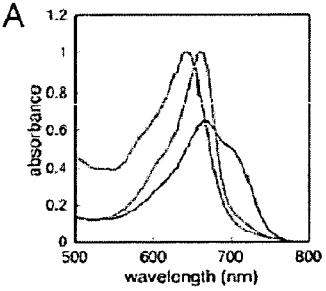
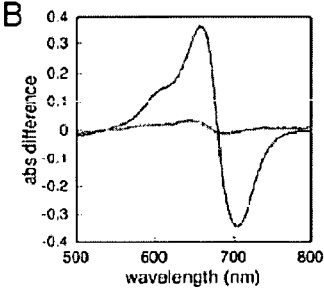
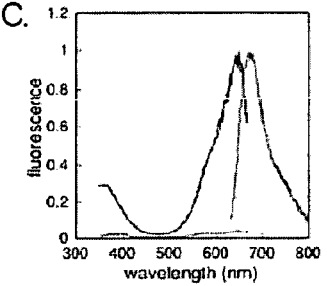
*Fig. 17*

SEQUENCE LISTING

<160> NUMBER OF SEQ ID NOS: 112

<210> SEQ ID NO 1
<211> LENGTH: 1542
<212> TYPE: DNA
<213> ORGANISM: Syncechocystis sp.

<400> SEQUENCE: 1

| | | | | | |
|---|---|---|---|---|---|
| atggccacca | ccgtacaact | cagcgaccaa | tccctccgtc | agctagaaac | cctcgccatc | 60 |
| cacaccgccc | acctgattca | gccccacggt | ttagtggtgg | tcctgcagga | accagacctc | 120 |
| accatcagcc | aaattagcac | caactgcacc | ggcattttag | ggcgatcgcc | agaggatttg | 180 |
| ttgggcagaa | ccctagggga | agtgtttgat | agctttcaga | ttgatcccat | ccagagtcgc | 240 |
| ctaacggccg | gacaaatcag | cagcctcaac | cccagtaaac | tttgggcgcg | gtcatgggg | 300 |
| gacgactttg | tcattttga | cggggttttt | catcgcaaca | gtgacggttt | attggtatgt | 360 |
| gaactcgagc | cagcctacac | ttccgataat | ctgcccttcc | tcggttttta | tcacatggcc | 420 |
| aacgctgccc | tgaatcggtt | gcgccaacaa | gctaatctac | gggatttcta | cgatgttatt | 480 |
| gtcgaagaag | tccgccgtat | gactggcttt | gaccgggtga | tgctacaccg | ctttgatgaa | 540 |
| aataaccacg | tgatgtcat | tgccgaagat | aaacggatg | atatggaacc | ctatttgggc | 600 |
| ctgcactatc | ccgaatcgga | tattccccaa | cccgcccgtc | ggctatttat | ccacaacccc | 660 |
| attcgagtaa | ttcccgatgt | ttatggtgtg | gcggtgcccc | tgaccccagc | ggttaacccc | 720 |
| agcaccaacc | gagcggtgga | tttaacagaa | tccaatctgc | gcagtgcgta | ccattgccac | 780 |
| ttgacctatc | tgaaaaatat | gggggtagga | gcgtctttaa | ccatttccct | aattaaggac | 840 |
| ggccatctct | gggggctcat | tgcctgccac | catcaaaccc | ccaaagtaat | tccctttgaa | 900 |
| ctgcgtaaag | cctgcgaatt | ttttggtcgg | gtggtgttta | gcaacatttc | cgcccaggaa | 960 |
| gatacggaaa | ccttcgatta | ccgggtgcag | ctggcggagc | atgaagcggt | tttattggac | 1020 |
| aaaatgacca | cggcggcgga | ttttgtcgaa | ggattaacta | atcatcccga | tcgcctgttg | 1080 |
| ggattaacgg | gctcccaggg | ggcggccatt | tgctttgggg | aaaaattgat | tttagtaggg | 1140 |
| gaaccccgg | acgagaaagc | agtgcaatat | ttactgcaat | ggttggagaa | tcggaagtg | 1200 |
| caagacgttt | tcttcacctc | ttccctctca | caaatttatc | ctgatgcagt | gaattttaaa | 1260 |
| tccgtggcca | gtggcttatt | ggccattccc | attgcccgtc | acaacttttt | gctctggttt | 1320 |
| cgccctgaag | tgttgcaaac | ggttaattgg | ggcggtgacc | caaatcatgc | ttacgaagct | 1380 |
| acccaggaag | acggtaaaat | cgagctccat | ccccgccaat | cctttgacct | ctggaaagaa | 1440 |
| attgtccgac | tccaatcttt | gccctggcaa | tcggtggaaa | tccaaagtgc | cctggccctg | 1500 |
| aaaaaggcga | tcgtcaacct | cattttgcgc | caggcagaag | aa | | 1542 |

<210> SEQ ID NO 2
<211> LENGTH: 514
<212> TYPE: PRT
<213> ORGANISM: Syncechocystis sp.

<400> SEQUENCE: 2

Met Ala Thr Thr Val Gln Leu Ser Asp Gln Ser Leu Arg Gln Leu Glu
1               5                   10                  15

Thr Leu Ala Ile His Thr Ala His Leu Ile Gln Pro His Gly Leu Val
            20                  25                  30

Val Val Leu Gln Glu Pro Asp Leu Thr Ile Ser Gln Ile Ser Thr Asn

-continued

```
                35                  40                  45
Cys Thr Gly Ile Leu Gly Arg Ser Pro Glu Asp Leu Leu Gly Arg Thr
 50                  55                  60
Leu Gly Glu Val Phe Asp Ser Phe Gln Ile Asp Pro Ile Gln Ser Arg
 65                  70                  75                  80
Leu Thr Ala Gly Gln Ile Ser Ser Leu Asn Pro Ser Lys Leu Trp Ala
                 85                  90                  95
Arg Val Met Gly Asp Asp Phe Val Ile Phe Asp Gly Val Phe His Arg
                100                 105                 110
Asn Ser Asp Gly Leu Leu Val Cys Glu Leu Glu Pro Ala Tyr Thr Ser
            115                 120                 125
Asp Asn Leu Pro Phe Leu Gly Phe Tyr His Met Ala Asn Ala Ala Leu
130                 135                 140
Asn Arg Leu Arg Gln Gln Ala Asn Leu Arg Asp Phe Tyr Asp Val Ile
145                 150                 155                 160
Val Glu Glu Val Arg Arg Met Thr Gly Phe Asp Arg Val Met Leu His
                165                 170                 175
Arg Phe Asp Glu Asn Asn His Gly Asp Val Ile Ala Glu Asp Lys Arg
            180                 185                 190
Asp Asp Met Glu Pro Tyr Leu Gly Leu His Tyr Pro Glu Ser Asp Ile
        195                 200                 205
Pro Gln Pro Ala Arg Arg Leu Phe Ile His Asn Pro Ile Arg Val Ile
    210                 215                 220
Pro Asp Val Tyr Gly Val Ala Val Pro Leu Thr Pro Ala Val Asn Pro
225                 230                 235                 240
Ser Thr Asn Arg Ala Val Asp Leu Thr Glu Ser Asn Leu Arg Ser Ala
                245                 250                 255
Tyr His Cys His Leu Thr Tyr Leu Lys Asn Met Gly Val Gly Ala Ser
            260                 265                 270
Leu Thr Ile Ser Leu Ile Lys Asp Gly His Leu Trp Gly Leu Ile Ala
        275                 280                 285
Cys His His Gln Thr Pro Lys Val Ile Pro Phe Glu Leu Arg Lys Ala
    290                 295                 300
Cys Glu Phe Phe Gly Arg Val Val Phe Ser Asn Ile Ser Ala Gln Glu
305                 310                 315                 320
Asp Thr Glu Thr Phe Asp Tyr Arg Val Gln Leu Ala Glu His Glu Ala
                325                 330                 335
Val Leu Leu Asp Lys Met Thr Thr Ala Ala Asp Phe Val Glu Gly Leu
            340                 345                 350
Thr Asn His Pro Asp Arg Leu Leu Gly Leu Thr Gly Ser Gln Gly Ala
        355                 360                 365
Ala Ile Cys Phe Gly Glu Lys Leu Ile Leu Val Gly Glu Thr Pro Asp
    370                 375                 380
Glu Lys Ala Val Gln Tyr Leu Leu Gln Trp Leu Glu Asn Arg Glu Val
385                 390                 395                 400
Gln Asp Val Phe Phe Thr Ser Ser Leu Ser Gln Ile Tyr Pro Asp Ala
                405                 410                 415
Val Asn Phe Lys Ser Val Ala Ser Gly Leu Leu Ala Ile Pro Ile Ala
            420                 425                 430
Arg His Asn Phe Leu Leu Trp Phe Arg Pro Glu Val Leu Gln Thr Val
        435                 440                 445
Asn Trp Gly Gly Asp Pro Asn His Ala Tyr Glu Ala Thr Gln Glu Asp
    450                 455                 460
```

```
Gly Lys Ile Glu Leu His Pro Arg Gln Ser Phe Asp Leu Trp Lys Glu
465                 470                 475                 480

Ile Val Arg Leu Gln Ser Leu Pro Trp Gln Ser Val Glu Ile Gln Ser
                485                 490                 495

Ala Leu Ala Leu Lys Lys Ala Ile Val Asn Leu Ile Leu Arg Gln Ala
            500                 505                 510

Glu Glu

<210> SEQ ID NO 3
<211> LENGTH: 1542
<212> TYPE: DNA
<213> ORGANISM: Syncechocystis sp.

<400> SEQUENCE: 3
atggccacca ccgtacaact cagcgaccaa tccctccgtc agctagaaac cctcgccatc      60
cacaccgccc acctgattca gccccacggt ttagtggtgg tcctgcagga accagacctc     120
accatcagcc aaattagcgc caactgcacc ggcattttag gcgatcgcc agaggatttg     180 ttgggcagaa ccctagggga agtgtttgat agctttcaga ttgatcccat ccagagtcgc     240
ctaacggccg acaaatcag cagcctcaac cccagtaaac tttgggcgcg gtcatgggg     300 gacgactttg tcattttga cggggttttt catcgcaaca gtgacggttt attggtatgt     360
gaactcgagc cagcctacac ttccgataat ctgcccttcc tcggttttta tcacatggcc     420
aacgctgccc tgaatcggtt cgccaacaa gctaatctac gggatttcta cgatgttatt     480
gtcgaagaag tccgccgtat gactggcttt gaccgggtga tgctataccg ctttgatgaa     540
aataaccacg tgatgtcat tgccgaagat aaacgggatg atatggaacc ctatttgggc     600
ctgcactatc ccgaatcgga tattccccaa cccgcccgtc ggctatttat ccacaaccc     660 attcgagtaa ttcccgatgt ttatggtgtg cgcggtgccc tgaccccagc ggttaaccc      720 agcaccaacc gagcggtgga tttaacagaa tccattctgc gcagtgcgta ccattgccac     780
ttgacctatc tgaaaaatat gggggtagga gcgtctttaa ccatttccct aattaaggac     840
ggccatctct ggggggctcat tgcctgccac catcaaaccc caaagtaat tccctttgaa     900 ctgcgtaaag cctgcgaatt ttttggtcgg gtggtgttta gcaacattc cgcccaggaa     960 gatacggaaa ccttcgatta ccgggtgcag ctggcggagc atgaagcggt tttattggac    1020
aaaatgacca cggcggcgga ttttgtcgaa ggattaacta atcatcccga tcgcctgttg    1080
ggattaacgg gctcccaggg ggcggccatt tgctttgggg aaaaattgat tttagtaggg    1140
gaaaccccgg acgagaaagc agtgcaatat ttactgcaat ggttggagaa tcggaagtg     1200 caagacgttt tcttcacctc ttccctctca caaatttatc ctgatgcagt gaattttaaa    1260
tccgtggcca gtggcttatt ggccattccc attgcccgtc acaacttttt gctctggttt    1320
cgccctgaag tgttgcaaac ggttaattgg ggcggtgacc caaatcatgc ttacgaagct    1380
acccaggaag acgtaaaaat cgagctccat ccccgccaat cctttgacct ctggaaagaa    1440
attgtccgac tccaatcttt gccctggcaa tcggtggaaa tccaaagtgc cctggccctg    1500
aaaaaggcga tcgtcaacct catttttgcgc caggcagaag aa                      1542

<210> SEQ ID NO 4
<211> LENGTH: 514
<212> TYPE: PRT
<213> ORGANISM: Syncechocystis sp.

<400> SEQUENCE: 4
```

-continued

```
Met Ala Thr Thr Val Gln Leu Ser Asp Gln Ser Leu Arg Gln Leu Glu
1               5                   10                  15

Thr Leu Ala Ile His Thr Ala His Leu Ile Gln Pro His Gly Leu Val
            20                  25                  30

Val Val Leu Gln Glu Pro Asp Leu Thr Ile Ser Gln Ile Ser Ala Asn
        35                  40                  45

Cys Thr Gly Ile Leu Gly Arg Ser Pro Glu Asp Leu Leu Gly Arg Thr
    50                  55                  60

Leu Gly Glu Val Phe Asp Ser Phe Gln Ile Asp Pro Ile Gln Ser Arg
65                  70                  75                  80

Leu Thr Ala Gly Gln Ile Ser Ser Leu Asn Pro Ser Lys Leu Trp Ala
                85                  90                  95

Arg Val Met Gly Asp Asp Phe Val Ile Phe Asp Gly Val Phe His Arg
            100                 105                 110

Asn Ser Asp Gly Leu Leu Val Cys Glu Leu Glu Pro Ala Tyr Thr Ser
        115                 120                 125

Asp Asn Leu Pro Phe Leu Gly Phe Tyr His Met Ala Asn Ala Ala Leu
    130                 135                 140

Asn Arg Leu Arg Gln Gln Ala Asn Leu Arg Asp Phe Tyr Asp Val Ile
145                 150                 155                 160

Val Glu Glu Val Arg Arg Met Thr Gly Phe Asp Arg Val Met Leu Tyr
                165                 170                 175

Arg Phe Asp Glu Asn Asn His Gly Asp Val Ile Ala Glu Asp Lys Arg
            180                 185                 190

Asp Asp Met Glu Pro Tyr Leu Gly Leu His Tyr Pro Glu Ser Asp Ile
        195                 200                 205

Pro Gln Pro Ala Arg Arg Leu Phe Ile His Asn Pro Ile Arg Val Ile
    210                 215                 220

Pro Asp Val Tyr Gly Val Ala Val Pro Leu Thr Pro Ala Val Asn Pro
225                 230                 235                 240

Ser Thr Asn Arg Ala Val Asp Leu Thr Glu Ser Ile Leu Arg Ser Ala
                245                 250                 255

Tyr His Cys His Leu Thr Tyr Leu Lys Asn Met Gly Val Gly Ala Ser
            260                 265                 270

Leu Thr Ile Ser Leu Ile Lys Asp Gly His Leu Trp Gly Leu Ile Ala
        275                 280                 285

Cys His His Gln Thr Pro Lys Val Ile Pro Phe Glu Leu Arg Lys Ala
    290                 295                 300

Cys Glu Phe Phe Gly Arg Val Val Phe Ser Asn Ile Ser Ala Gln Glu
305                 310                 315                 320

Asp Thr Glu Thr Phe Asp Tyr Arg Val Gln Leu Ala Glu His Glu Ala
                325                 330                 335

Val Leu Leu Asp Lys Met Thr Thr Ala Ala Asp Phe Val Glu Gly Leu
            340                 345                 350

Thr Asn His Pro Asp Arg Leu Leu Gly Leu Thr Gly Ser Gln Gly Ala
        355                 360                 365

Ala Ile Cys Phe Gly Glu Lys Leu Ile Leu Val Gly Glu Thr Pro Asp
    370                 375                 380

Glu Lys Ala Val Gln Tyr Leu Leu Gln Trp Leu Glu Asn Arg Glu Val
385                 390                 395                 400

Gln Asp Val Phe Phe Thr Ser Ser Leu Ser Gln Ile Tyr Pro Asp Ala
                405                 410                 415
```

-continued

```
Val Asn Phe Lys Ser Val Ala Ser Gly Leu Leu Ala Ile Pro Ile Ala
            420                 425                 430

Arg His Asn Phe Leu Leu Trp Phe Arg Pro Glu Val Leu Gln Thr Val
        435                 440                 445

Asn Trp Gly Gly Asp Pro Asn His Ala Tyr Glu Ala Thr Gln Glu Asp
    450                 455                 460

Gly Lys Ile Glu Leu His Pro Arg Gln Ser Phe Asp Leu Trp Lys Glu
465                 470                 475                 480

Ile Val Arg Leu Gln Ser Leu Pro Trp Gln Ser Val Glu Ile Gln Ser
                485                 490                 495

Ala Leu Ala Leu Lys Lys Ala Ile Val Asn Leu Ile Leu Arg Gln Ala
            500                 505                 510

Glu Glu

<210> SEQ ID NO 5
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 5
gggctaacag gaggaattaa ccatg                                        25

<210> SEQ ID NO 6
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 6
gcaagcttgt tcttctgcct ggcg                                         24

<210> SEQ ID NO 7
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 7
cttcgattac cgggtgcagc tg                                           22

<210> SEQ ID NO 8
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 8
gcaagcttgt tcttctgcct ggcg                                         24

<210> SEQ ID NO 9
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 9
gggctaacag gaggaattaa ccatg                                        25
```

<210> SEQ ID NO 10
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 10
cggaagtgta ggctggctcg                                          20

<210> SEQ ID NO 11
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 11
gacggtttat ggtatgtgaa ctcg                                     24

<210> SEQ ID NO 12
<211> LENGTH: 27
<212> TYPE: DNA
<213> ORGANISM: Artificial
<220> FEATURE:
<223> OTHER INFORMATION: Synthetic oligonucleotide PCR primer

<400> SEQUENCE: 12
caataaaacc gcttcatgct ccgccag                                  27

<210> SEQ ID NO 13
<211> LENGTH: 36
<212> TYPE: DNA
<213> ORGANISM: Artificial
<220> FEATURE:
<223> OTHER INFORMATION: Synthetic oligonucleotide PCR primer

<400> SEQUENCE: 13
gaccgggtga tgctagcgcg ctttgatgaa aataac                        36

<210> SEQ ID NO 14
<211> LENGTH: 36
<212> TYPE: DNA
<213> ORGANISM: Artificial
<220> FEATURE:
<223> OTHER INFORMATION: Synthetic oligonucleotide PCR primer

<400> SEQUENCE: 14
gttattttca tcaaagcgcg ctagcatcac ccggtc                        36

<210> SEQ ID NO 15
<211> LENGTH: 36
<212> TYPE: DNA
<213> ORGANISM: Artificial
<220> FEATURE:
<223> OTHER INFORMATION: Synthetic oligonucleotide PCR primer

<400> SEQUENCE: 15
gaccgggtga tgctatgccg ctttgatgaa aataac                        36

<210> SEQ ID NO 16
<211> LENGTH: 36
<212> TYPE: DNA
<213> ORGANISM: Artificial
<220> FEATURE:

-continued

<223> OTHER INFORMATION: Synthetic oligonucleotide PCR primer

<400> SEQUENCE: 16 gttatttca tcaaagcggc atagcatcac ccggtc        36

<210> SEQ ID NO 17
<211> LENGTH: 36
<212> TYPE: DNA
<213> ORGANISM: Artificial
<220> FEATURE:
<223> OTHER INFORMATION: Synthetic oligonucleotide PCR primer

<400> SEQUENCE: 17
gaccgggtga tgctagaacg ctttgatgaa aataac        36

<210> SEQ ID NO 18
<211> LENGTH: 36
<212> TYPE: DNA
<213> ORGANISM: Artificial
<220> FEATURE:
<223> OTHER INFORMATION: Synthetic oligonucleotide PCR primer

<400> SEQUENCE: 18 gttatttca tcaaagcgtt ctagcatcac ccggtc        36

<210> SEQ ID NO 19
<211> LENGTH: 39
<212> TYPE: DNA
<213> ORGANISM: Artificial
<220> FEATURE:
<223> OTHER INFORMATION: Synthetic oligonucleotide PCR primer

<400> SEQUENCE: 19
ccgggtgatg ctatttcgct ttgatgaaaa taaccacgg        39

<210> SEQ ID NO 20
<211> LENGTH: 36
<212> TYPE: DNA
<213> ORGANISM: Artificial
<220> FEATURE:
<223> OTHER INFORMATION: Synthetic oligonucleotide PCR primer

<400> SEQUENCE: 20
ttcatcaaag cggaatagca tcacccggtc aaagcc        36

<210> SEQ ID NO 21
<211> LENGTH: 35
<212> TYPE: DNA
<213> ORGANISM: Artificial
<220> FEATURE:
<223> OTHER INFORMATION: Synthetic oligonucleotide PCR primer

<400> SEQUENCE: 21
ccgggtgatg ctacaccgct tgatgaaaa taacc        35

<210> SEQ ID NO 22
<211> LENGTH: 34
<212> TYPE: DNA
<213> ORGANISM: Artificial
<220> FEATURE:
<223> OTHER INFORMATION: Synthetic oligonucleotide PCR primer

<400> SEQUENCE: 22
catcaaagcg gtgtagcatc acccggtcaa agcc        34

<210> SEQ ID NO 23
<211> LENGTH: 36
<212> TYPE: DNA
<213> ORGANISM: Artificial
<220> FEATURE:
<223> OTHER INFORMATION: Synthetic oligonucleotide PCR primer

<400> SEQUENCE: 23
gaccgggtga tgctacagcg ctttgatgaa aataac        36

<210> SEQ ID NO 24
<211> LENGTH: 36
<212> TYPE: DNA
<213> ORGANISM: Artificial
<220> FEATURE:
<223> OTHER INFORMATION: Synthetic oligonucleotide PCR primer

<400> SEQUENCE: 24
gttattttca tcaaagcgct gtagcatcac ccggtc        36

<210> SEQ ID NO 25
<211> LENGTH: 36
<212> TYPE: DNA
<213> ORGANISM: Artificial
<220> FEATURE:
<223> OTHER INFORMATION: Synthetic oligonucleotide PCR primer

<400> SEQUENCE: 25
gaccgggtga tgctaagccg ctttgatgaa aataac        36

<210> SEQ ID NO 26
<211> LENGTH: 36
<212> TYPE: DNA
<213> ORGANISM: Artificial
<220> FEATURE:
<223> OTHER INFORMATION: Synthetic oligonucleotide PCR primer

<400> SEQUENCE: 26
gttattttca tcaaagcggc ttagcatcac ccggtc        36

<210> SEQ ID NO 27
<211> LENGTH: 39
<212> TYPE: DNA
<213> ORGANISM: Artificial
<220> FEATURE:
<223> OTHER INFORMATION: Synthetic oligonucleotide PCR primer

<400> SEQUENCE: 27
ccgggtgatg ctatggcgct ttgatgaaaa taaccacgg        39

<210> SEQ ID NO 28
<211> LENGTH: 36
<212> TYPE: DNA
<213> ORGANISM: Artificial
<220> FEATURE:
<223> OTHER INFORMATION: Synthetic oligonucleotide PCR primer

<400> SEQUENCE: 28
ttcatcaaag cgccatagca tcacccggtc aaagcc        36

<210> SEQ ID NO 29
<211> LENGTH: 30
<212> TYPE: DNA
<213> ORGANISM: Artificial
<220> FEATURE:
<223> OTHER INFORMATION: Synthetic oligonucleotide PCR primer -continued

<210> SEQ ID NO 29 catgccatgg ccaccaccgt acaactcagc            30

<210> SEQ ID NO 30
<211> LENGTH: 30
<212> TYPE: DNA
<213> ORGANISM: Artificial
<220> FEATURE:
<223> OTHER INFORMATION: Synthetic oligonucleotide PCR primer

<400> SEQUENCE: 30
cccaagcttc ttcgacaaaa tccgccgccg            30

<210> SEQ ID NO 31
<211> LENGTH: 34
<212> TYPE: DNA
<213> ORGANISM: Artificial
<220> FEATURE:
<223> OTHER INFORMATION: Synthetic oligonucleotide PCR primer

<400> SEQUENCE: 31
gacagggtga tggctcacaa gtttcatgaa gatg            34

<210> SEQ ID NO 32
<211> LENGTH: 34
<212> TYPE: DNA
<213> ORGANISM: Artificial
<220> FEATURE:
<223> OTHER INFORMATION: Synthetic oligonucleotide PCR primer

<400> SEQUENCE: 32
catcttcatg aaacttgtga gccatcaccc tgtc            34

<210> SEQ ID NO 33
<211> LENGTH: 763
<212> TYPE: PRT
<213> ORGANISM: Syncechocystis sp.

<400> SEQUENCE: 33

Met Ala Thr Thr Val Gln Leu Ser Asp Gln Ser Leu Arg Gln Leu Glu
1               5                   10                  15

Thr Leu Ala Ile His Thr Ala His Leu Ile Gln Pro His Gly Leu Val
            20                  25                  30

Val Val Leu Gln Glu Pro Asp Leu Thr Ile Ser Gln Ile Ser Ala Asn
        35                  40                  45

Cys Thr Gly Ile Leu Gly Arg Ser Pro Glu Asp Leu Leu Gly Arg Thr
    50                  55                  60

Leu Gly Glu Val Phe Asp Ser Phe Gln Ile Asp Pro Ile Gln Ser Arg
65                  70                  75                  80

Leu Thr Ala Gly Gln Ile Ser Ser Leu Asn Pro Ser Lys Leu Trp Ala
                85                  90                  95

Arg Val Met Gly Asp Asp Phe Val Ile Phe Asp Gly Val Phe His Arg
            100                 105                 110

Asn Ser Asp Gly Leu Leu Val Cys Glu Leu Glu Pro Ala Tyr Thr Ser
        115                 120                 125

Asp Asn Leu Pro Phe Leu Gly Phe Tyr His Met Ala Asn Ala Ala Leu
    130                 135                 140

Asn Arg Leu Arg Gln Gln Ala Asn Leu Arg Asp Phe Tyr Asp Val Ile
145                 150                 155                 160

Val Glu Glu Val Arg Arg Met Thr Gly Phe Asp Arg Val Met Leu Tyr

-continued

```
              165                 170                 175
Arg Phe Asp Glu Asn Asn His Gly Asp Val Ile Ala Glu Asp Lys Arg
            180                 185                 190

Asp Asp Met Glu Pro Tyr Leu Gly Leu His Tyr Pro Glu Ser Asp Ile
        195                 200                 205

Pro Gln Pro Ala Arg Arg Leu Phe Ile His Asn Pro Ile Arg Val Ile
    210                 215                 220

Pro Asp Val Tyr Gly Val Ala Val Pro Leu Thr Pro Ala Val Asn Pro
225                 230                 235                 240

Ser Thr Asn Arg Ala Val Asp Leu Thr Glu Ser Ile Leu Arg Ser Ala
                245                 250                 255

Tyr His Cys His Leu Thr Tyr Leu Lys Asn Met Gly Val Gly Ala Ser
            260                 265                 270

Leu Thr Ile Ser Leu Ile Lys Asp Gly His Leu Trp Gly Leu Ile Ala
        275                 280                 285

Cys His His Gln Thr Pro Lys Val Ile Pro Phe Glu Leu Arg Lys Ala
    290                 295                 300

Cys Glu Phe Phe Gly Arg Val Val Phe Ser Asn Ile Ser Ala Gln Glu
305                 310                 315                 320

Asp Thr Glu Thr Phe Asp Tyr Arg Val Gln Leu Ala Glu His Glu Ala
                325                 330                 335

Val Leu Leu Asp Lys Met Thr Thr Ala Ala Asp Phe Val Glu Gly Leu
            340                 345                 350

Thr Asn His Pro Asp Arg Leu Leu Gly Leu Thr Gly Ser Gln Gly Ala
        355                 360                 365

Ala Ile Cys Phe Gly Glu Lys Leu Ile Leu Val Gly Glu Thr Pro Asp
    370                 375                 380

Glu Lys Ala Val Gln Tyr Leu Leu Gln Trp Leu Glu Asn Arg Glu Val
385                 390                 395                 400

Gln Asp Val Phe Phe Thr Ser Ser Leu Ser Gln Ile Tyr Pro Asp Ala
                405                 410                 415

Val Asn Phe Lys Ser Val Ala Ser Gly Leu Leu Ala Ile Pro Ile Ala
            420                 425                 430

Arg His Asn Phe Leu Leu Trp Phe Arg Pro Glu Val Leu Gln Thr Val
        435                 440                 445

Asn Trp Gly Gly Asp Pro Asn His Ala Tyr Glu Ala Thr Gln Glu Asp
    450                 455                 460

Gly Lys Ile Glu Leu His Pro Arg Gln Ser Phe Asp Leu Trp Lys Glu
465                 470                 475                 480

Ile Val Arg Leu Gln Ser Leu Pro Trp Gln Ser Val Glu Ile Gln Ser
                485                 490                 495

Ala Leu Ala Leu Lys Lys Ala Ile Val Asn Leu Ile Leu Arg Gln Ala
            500                 505                 510

Glu Glu Leu Ala Gln Leu Ala Arg Asn Leu Glu Arg Ser Asn Ala Asp
        515                 520                 525

Leu Lys Lys Phe Ala Tyr Ile Ala Ser His Asp Leu Gln Glu Pro Leu
    530                 535                 540

Asn Gln Val Ser Asn Tyr Val Gln Leu Leu Glu Met Arg Tyr Ser Glu
545                 550                 555                 560

Ala Leu Asp Glu Asp Ala Lys Asp Phe Ile Asp Phe Ala Val Thr Gly
                565                 570                 575

Val Ser Leu Met Gln Thr Leu Ile Asp Asp Ile Leu Thr Tyr Ala Lys
            580                 585                 590
```

Val Asp Thr Gln Tyr Ala Gln Leu Thr Phe Thr Asp Val Gln Glu Val
            595                 600                 605

Val Asp Lys Ala Leu Ala Asn Leu Lys Gln Arg Ile Glu Glu Ser Gly
            610                 615                 620

Ala Glu Ile Glu Val Gly Ser Met Pro Ala Val Met Ala Asp Gln Ile
625                 630                 635                 640

Gln Leu Met Gln Val Phe Gln Asn Leu Ile Ala Asn Gly Ile Lys Phe
            645                 650                 655

Ala Gly Asp Lys Ser Pro Lys Ile Lys Ile Trp Gly Asp Arg Gln Glu
            660                 665                 670

Asp Ala Trp Val Phe Ala Val Gln Asp Asn Gly Ile Gly Ile Asp Pro
            675                 680                 685

Gln Phe Phe Glu Arg Ile Phe Val Ile Phe Gln Arg Leu His Thr Arg
            690                 695                 700

Asp Glu Tyr Lys Gly Thr Gly Met Gly Leu Ala Ile Cys Lys Lys Ile
705                 710                 715                 720

Ile Glu Gly His Gln Gly Gln Ile Trp Leu Glu Ser Asn Pro Gly Glu
            725                 730                 735

Gly Ser Thr Phe Tyr Phe Ser Ile Pro Ile Gly Asn Gly Arg Pro Ala
            740                 745                 750

Gly Ser Ala Trp Arg His Pro Gln Phe Gly Gly
            755                 760

<210> SEQ ID NO 34
<211> LENGTH: 774
<212> TYPE: PRT
<213> ORGANISM: Syncechocystis sp.

<400> SEQUENCE: 34

Met Ala Thr Thr Val Gln Leu Ser Asp Gln Ser Leu Arg Gln Leu Glu
1               5                   10                  15

Thr Leu Ala Ile His Thr Ala His Leu Ile Gln Pro His Gly Leu Val
            20                  25                  30

Val Val Leu Gln Glu Pro Asp Leu Thr Ile Ser Gln Ile Ser Ala Asn
            35                  40                  45

Cys Thr Gly Ile Leu Gly Arg Ser Pro Glu Asp Leu Leu Gly Arg Thr
        50                  55                  60

Leu Gly Glu Val Phe Asp Ser Phe Gln Ile Asp Pro Ile Gln Ser Arg
65              70                  75                  80

Leu Thr Ala Gly Gln Ile Ser Ser Leu Asn Pro Ser Lys Leu Trp Ala
            85                  90                  95

Arg Val Met Gly Asp Asp Phe Val Ile Phe Asp Gly Val Phe His Arg
                100                 105                 110

Asn Ser Asp Gly Leu Leu Val Cys Glu Leu Glu Pro Ala Tyr Thr Ser
            115                 120                 125

Asp Asn Leu Pro Phe Leu Gly Phe Tyr His Met Ala Asn Ala Ala Leu
        130                 135                 140

Asn Arg Leu Arg Gln Gln Ala Asn Leu Arg Asp Phe Tyr Asp Val Ile
145                 150                 155                 160

Val Glu Glu Val Arg Arg Met Thr Gly Phe Asp Arg Val Met Leu Tyr
                165                 170                 175

Arg Phe Asp Glu Asn Asn His Gly Asp Val Ile Ala Glu Asp Lys Arg
            180                 185                 190

Asp Asp Met Glu Pro Tyr Leu Gly Leu His Tyr Pro Glu Ser Asp Ile

-continued

```
              195                 200                 205
Pro Gln Pro Ala Arg Arg Leu Phe Ile His Asn Pro Ile Arg Val Ile
    210                 215                 220

Pro Asp Val Tyr Gly Val Ala Val Pro Leu Thr Pro Ala Val Asn Pro
225                 230                 235                 240

Ser Thr Asn Arg Ala Val Asp Leu Thr Glu Ser Ile Leu Arg Ser Ala
                245                 250                 255

Tyr His Cys His Leu Thr Tyr Leu Lys Asn Met Gly Val Gly Ala Ser
                260                 265                 270

Leu Thr Ile Ser Leu Ile Lys Asp Gly His Leu Trp Gly Leu Ile Ala
            275                 280                 285

Cys His Gln Thr Pro Lys Val Ile Pro Phe Glu Leu Arg Lys Ala
        290                 295                 300

Cys Glu Phe Phe Gly Arg Val Val Phe Ser Asn Ile Ser Ala Gln Glu
305                 310                 315                 320

Asp Thr Glu Thr Phe Asp Tyr Arg Val Gln Leu Ala Glu His Glu Ala
                325                 330                 335

Val Leu Leu Asp Lys Met Thr Thr Ala Ala Asp Phe Val Glu Gly Leu
                340                 345                 350

Thr Asn His Pro Asp Arg Leu Leu Gly Leu Thr Gly Ser Gln Gly Ala
                355                 360                 365

Ala Ile Cys Phe Gly Glu Lys Leu Ile Leu Val Gly Glu Thr Pro Asp
    370                 375                 380

Glu Lys Ala Val Gln Tyr Leu Leu Gln Trp Leu Glu Asn Arg Glu Val
385                 390                 395                 400

Gln Asp Val Phe Phe Thr Ser Ser Leu Ser Gln Ile Tyr Pro Asp Ala
                405                 410                 415

Val Asn Phe Lys Ser Val Ala Ser Gly Leu Leu Ala Ile Pro Ile Ala
                420                 425                 430

Arg His Asn Phe Leu Leu Trp Phe Arg Pro Glu Val Leu Gln Thr Val
                435                 440                 445

Asn Trp Gly Gly Asp Pro Asn His Ala Tyr Glu Ala Thr Gln Glu Asp
    450                 455                 460

Gly Lys Ile Glu Leu His Pro Arg Gln Ser Phe Asp Leu Trp Lys Glu
465                 470                 475                 480

Ile Val Arg Leu Gln Ser Leu Pro Trp Gln Ser Val Glu Ile Gln Ser
                485                 490                 495

Ala Leu Ala Leu Lys Lys Ala Ile Val Asn Leu Ile Leu Arg Gln Ala
                500                 505                 510

Glu Glu Leu Ala Gln Leu Ala Arg Asn Leu Glu Arg Ser Asn Ala Asp
                515                 520                 525

Leu Lys Lys Phe Ala Tyr Ile Ala Ser His Asp Leu Gln Glu Pro Leu
    530                 535                 540

Asn Gln Val Ser Asn Tyr Val Gln Leu Leu Glu Met Arg Tyr Ser Glu
545                 550                 555                 560

Ala Leu Asp Glu Asp Ala Lys Asp Phe Ile Asp Phe Ala Val Thr Gly
                565                 570                 575

Val Ser Leu Met Gln Thr Leu Ile Asp Asp Ile Leu Thr Tyr Ala Lys
                580                 585                 590

Val Asp Thr Gln Tyr Ala Gln Leu Thr Phe Thr Asp Val Gln Glu Val
            595                 600                 605

Val Asp Lys Ala Leu Ala Asn Leu Lys Gln Arg Ile Glu Glu Ser Gly
    610                 615                 620
```

```
Ala Glu Ile Glu Val Gly Ser Met Pro Ala Val Met Ala Asp Gln Ile
625                 630                 635                 640

Gln Leu Met Gln Val Phe Gln Asn Leu Ile Ala Asn Gly Ile Lys Phe
            645                 650                 655

Ala Gly Asp Lys Ser Pro Lys Ile Lys Ile Trp Gly Asp Arg Gln Glu
        660                 665                 670

Asp Ala Trp Val Phe Ala Val Gln Asp Asn Gly Ile Gly Ile Asp Pro
            675                 680                 685

Gln Phe Phe Glu Arg Ile Phe Val Ile Phe Gln Arg Leu His Thr Arg
690                 695                 700

Asp Glu Tyr Lys Gly Thr Gly Met Gly Leu Ala Ile Cys Lys Lys Ile
705                 710                 715                 720

Ile Glu Gly His Gln Gly Gln Ile Trp Leu Ser Asn Pro Gly Glu
                725                 730                 735

Gly Ser Thr Phe Tyr Phe Ser Ile Pro Ile Gly Asn Gly Arg Ser Phe
            740                 745                 750

Leu Glu Gln Lys Leu Ile Ser Glu Glu Asp Leu Asn Ser Ala Val Asp
        755                 760                 765

His His His His His His
        770

<210> SEQ ID NO 35
<211> LENGTH: 770
<212> TYPE: PRT
<213> ORGANISM: Syncechocystis sp.

<400> SEQUENCE: 35

Ala Asx Asx Tyr Tyr Ala Pro Met Ala Thr Thr Val Gln Leu Ser Asp
1               5                   10                  15

Gln Ser Leu Arg Gln Leu Glu Thr Leu Ala Ile His Thr Ala His Leu
            20                  25                  30

Ile Gln Pro His Gly Leu Val Val Leu Gln Glu Pro Asp Leu Thr
        35                  40                  45

Ile Ser Gln Ile Ser Ala Asn Cys Thr Gly Ile Leu Gly Arg Ser Pro
50                  55                  60

Glu Asp Leu Leu Gly Arg Thr Leu Gly Glu Val Phe Asp Ser Phe Gln
65                  70                  75                  80

Ile Asp Pro Ile Gln Ser Arg Leu Thr Ala Gly Gln Ile Ser Ser Leu
            85                  90                  95

Asn Pro Ser Lys Leu Trp Ala Arg Val Met Gly Asp Asp Phe Val Ile
        100                 105                 110

Phe Asp Gly Val Phe His Arg Asn Ser Asp Gly Leu Leu Val Cys Glu
        115                 120                 125

Leu Glu Pro Ala Tyr Thr Ser Asp Asn Leu Pro Phe Leu Gly Phe Tyr
    130                 135                 140

His Met Ala Asn Ala Ala Leu Asn Arg Leu Arg Gln Gln Ala Asn Leu
145                 150                 155                 160

Arg Asp Phe Tyr Asp Val Ile Val Glu Glu Val Arg Arg Met Thr Gly
                165                 170                 175

Phe Asp Arg Val Met Leu His Arg Phe Asp Glu Asn Asn His Gly Asp
            180                 185                 190

Val Ile Ala Glu Asp Lys Arg Asp Asp Met Glu Pro Tyr Leu Gly Leu
        195                 200                 205

His Tyr Pro Glu Ser Asp Ile Pro Gln Pro Ala Arg Arg Leu Phe Ile
```

-continued

```
            210                 215                 220
His Asn Pro Ile Arg Val Ile Pro Asp Val Tyr Gly Val Ala Val Pro
225                 230                 235                 240

Leu Thr Pro Ala Val Asn Pro Ser Thr Asn Arg Ala Val Asp Leu Thr
                245                 250                 255

Glu Ser Ile Leu Arg Ser Ala Tyr His Cys His Leu Thr Tyr Leu Lys
                260                 265                 270

Asn Met Gly Val Gly Ala Ser Leu Thr Ile Ser Leu Ile Lys Asp Gly
                275                 280                 285

His Leu Trp Gly Leu Ile Ala Cys His His Gln Thr Pro Lys Val Ile
290                 295                 300

Pro Phe Glu Leu Arg Lys Ala Cys Glu Phe Phe Gly Arg Val Val Phe
305                 310                 315                 320

Ser Asn Ile Ser Ala Gln Glu Asp Thr Glu Thr Phe Asp Tyr Arg Val
                325                 330                 335

Gln Leu Ala Glu His Glu Ala Val Leu Leu Asp Lys Met Thr Thr Ala
                340                 345                 350

Ala Asp Phe Val Glu Gly Leu Thr Asn His Pro Asp Arg Leu Leu Gly
                355                 360                 365

Leu Thr Gly Ser Gln Gly Ala Ala Ile Cys Phe Gly Glu Lys Leu Ile
                370                 375                 380

Leu Val Gly Glu Thr Pro Asp Glu Lys Ala Val Gln Tyr Leu Leu Gln
385                 390                 395                 400

Trp Leu Glu Asn Arg Glu Val Gln Asp Val Phe Phe Thr Ser Ser Leu
                405                 410                 415

Ser Gln Ile Tyr Pro Asp Ala Val Asn Phe Lys Ser Val Ala Ser Gly
                420                 425                 430

Leu Leu Ala Ile Pro Ile Ala Arg His Asn Phe Leu Leu Trp Phe Arg
                435                 440                 445

Pro Glu Val Leu Gln Thr Val Asn Trp Gly Gly Asp Pro Asn His Ala
                450                 455                 460

Tyr Glu Ala Thr Gln Glu Asp Gly Lys Ile Glu Leu His Pro Arg Gln
465                 470                 475                 480

Ser Phe Asp Leu Trp Lys Glu Ile Val Arg Leu Gln Ser Leu Pro Trp
                485                 490                 495

Gln Ser Val Glu Ile Gln Ser Ala Leu Ala Leu Lys Lys Ala Ile Val
                500                 505                 510

Asn Leu Ile Leu Arg Gln Ala Glu Glu Leu Ala Gln Leu Ala Arg Asn
                515                 520                 525

Leu Glu Arg Ser Asn Ala Asp Leu Lys Lys Phe Ala Tyr Ile Ala Ser
530                 535                 540

His Asp Leu Gln Glu Pro Leu Asn Gln Val Ser Asn Tyr Val Gln Leu
545                 550                 555                 560

Leu Glu Met Arg Tyr Ser Glu Ala Leu Asp Glu Ala Lys Asp Phe
                565                 570                 575

Ile Asp Phe Ala Val Thr Gly Val Ser Leu Met Gln Thr Leu Ile Asp
                580                 585                 590

Asp Ile Leu Thr Tyr Ala Lys Val Asp Thr Gln Tyr Ala Gln Leu Thr
                595                 600                 605

Phe Thr Asp Val Gln Glu Val Val Asp Lys Ala Leu Ala Asn Leu Lys
                610                 615                 620

Gln Arg Ile Glu Glu Ser Gly Ala Glu Ile Glu Val Gly Ser Met Pro
625                 630                 635                 640
```

```
Ala Val Met Ala Asp Gln Ile Gln Leu Met Gln Val Phe Gln Asn Leu
                645                 650                 655
Ile Ala Asn Gly Ile Lys Phe Ala Gly Asp Lys Ser Pro Lys Ile Lys
            660                 665                 670
Ile Trp Gly Asp Arg Gln Glu Asp Ala Trp Val Phe Ala Val Gln Asp
        675                 680                 685
Asn Gly Ile Gly Ile Asp Pro Gln Phe Phe Glu Arg Ile Phe Val Ile
    690                 695                 700
Phe Gln Arg Leu His Thr Arg Asp Glu Tyr Lys Gly Thr Gly Met Gly
705                 710                 715                 720
Leu Ala Ile Cys Lys Lys Ile Ile Glu Gly His Gln Gly Gln Ile Trp
                725                 730                 735
Leu Glu Ser Asn Pro Gly Glu Gly Ser Thr Phe Tyr Phe Ser Ile Pro
            740                 745                 750
Ile Gly Asn Gly Arg Pro Ala Gly Ser Ala Trp Arg His Pro Gln Phe
        755                 760                 765
Gly Gly
    770

<210> SEQ ID NO 36
<211> LENGTH: 539
<212> TYPE: PRT
<213> ORGANISM: Syncechocystis sp.

<400> SEQUENCE: 36

Met Ala Thr Thr Val Gln Leu Ser Asp Gln Ser Leu Arg Gln Leu Glu
1               5                   10                  15
Thr Leu Ala Ile His Thr Ala His Leu Ile Gln Pro His Gly Leu Val
            20                  25                  30
Val Val Leu Gln Glu Pro Asp Leu Thr Ile Ser Gln Ile Ser Ala Asn
        35                  40                  45
Cys Thr Gly Ile Leu Gly Arg Ser Pro Glu Asp Leu Leu Gly Arg Thr
    50                  55                  60
Leu Gly Glu Val Phe Asp Ser Phe Gln Ile Asp Pro Ile Gln Ser Arg
65                  70                  75                  80
Leu Thr Ala Gly Gln Ile Ser Ser Leu Asn Pro Ser Lys Leu Trp Ala
                85                  90                  95
Arg Val Met Gly Asp Asp Phe Val Ile Phe Asp Gly Val Phe His Arg
            100                 105                 110
Asn Ser Asp Gly Leu Leu Val Cys Glu Leu Glu Pro Ala Tyr Thr Ser
        115                 120                 125
Asp Asn Leu Pro Phe Leu Gly Phe Tyr His Met Ala Asn Ala Ala Leu
    130                 135                 140
Asn Arg Leu Arg Gln Gln Ala Asn Leu Arg Asp Phe Tyr Asp Val Ile
145                 150                 155                 160
Val Glu Glu Val Arg Arg Met Thr Gly Phe Asp Arg Val Met Leu Tyr
                165                 170                 175
Arg Phe Asp Glu Asn Asn His Gly Asp Val Ile Ala Glu Asp Lys Arg
            180                 185                 190
Asp Asp Met Glu Pro Tyr Leu Gly Leu His Tyr Pro Glu Ser Asp Ile
        195                 200                 205
Pro Gln Pro Ala Arg Arg Leu Phe Ile His Asn Pro Ile Arg Val Ile
    210                 215                 220
Pro Asp Val Tyr Gly Val Ala Val Pro Leu Thr Pro Ala Val Asn Pro
```

```
                225                 230                 235                 240
Ser Thr Asn Arg Ala Val Asp Leu Thr Glu Ser Ile Leu Arg Ser Ala
                245                 250                 255

Tyr His Cys His Leu Thr Tyr Leu Lys Asn Met Gly Val Gly Ala Ser
            260                 265                 270

Leu Thr Ile Ser Leu Ile Lys Asp Gly His Leu Trp Gly Leu Ile Ala
        275                 280                 285

Cys His His Gln Thr Pro Lys Val Ile Pro Phe Glu Leu Arg Lys Ala
    290                 295                 300

Cys Glu Phe Phe Gly Arg Val Val Phe Ser Asn Ile Ser Ala Gln Glu
305                 310                 315                 320

Asp Thr Glu Thr Phe Asp Tyr Arg Val Gln Leu Ala Glu His Glu Ala
                325                 330                 335

Val Leu Leu Asp Lys Met Thr Thr Ala Ala Asp Phe Val Glu Gly Leu
            340                 345                 350

Thr Asn His Pro Asp Arg Leu Leu Gly Leu Thr Gly Ser Gln Gly Ala
        355                 360                 365

Ala Ile Cys Phe Gly Glu Lys Leu Ile Leu Val Gly Glu Thr Pro Asp
    370                 375                 380

Glu Lys Ala Val Gln Tyr Leu Leu Gln Trp Leu Glu Asn Arg Glu Val
385                 390                 395                 400

Gln Asp Val Phe Phe Thr Ser Ser Leu Ser Gln Ile Tyr Pro Asp Ala
                405                 410                 415

Val Asn Phe Lys Ser Val Ala Ser Gly Leu Leu Ala Ile Pro Ile Ala
            420                 425                 430

Arg His Asn Phe Leu Leu Trp Phe Arg Pro Glu Val Leu Gln Thr Val
        435                 440                 445

Asn Trp Gly Gly Asp Pro Asn His Ala Tyr Glu Ala Thr Gln Glu Asp
    450                 455                 460

Gly Lys Ile Glu Leu His Pro Arg Gln Ser Phe Asp Leu Trp Lys Glu
465                 470                 475                 480

Ile Val Arg Leu Gln Ser Leu Pro Trp Gln Ser Val Glu Ile Gln Ser
                485                 490                 495

Ala Leu Ala Leu Lys Lys Ala Ile Val Asn Leu Ile Leu Arg Gln Ala
            500                 505                 510

Glu Gln Ala Tyr Val Glu Gln Lys Leu Ile Ser Glu Glu Asp Leu
        515                 520                 525

Asn Ser Ala Val Asp His His His His His
    530                 535

<210> SEQ ID NO 37
<211> LENGTH: 539
<212> TYPE: PRT
<213> ORGANISM: Syncechocystis sp.

<400> SEQUENCE: 37

Met Ala Thr Thr Val Gln Leu Ser Asp Gln Ser Leu Arg Gln Leu Glu
1               5                   10                  15

Thr Leu Ala Ile His Thr Ala His Leu Ile Gln Pro His Gly Leu Val
            20                  25                  30

Val Val Leu Gln Glu Pro Asp Leu Thr Ile Ser Gln Ile Ser Ala Asn
        35                  40                  45

Cys Thr Gly Ile Leu Gly Arg Ser Pro Glu Asp Leu Leu Gly Arg Thr
    50                  55                  60
```

-continued

```
Leu Gly Glu Val Phe Asp Ser Phe Gln Ile Asp Pro Ile Gln Ser Arg
 65                  70                  75                  80

Leu Thr Ala Gly Gln Ile Ser Ser Leu Asn Pro Ser Lys Leu Trp Ala
                 85                  90                  95

Arg Val Met Gly Asp Asp Phe Val Ile Phe Asp Gly Val Phe His Arg
            100                 105                 110

Asn Ser Asp Gly Leu Leu Val Cys Glu Leu Glu Pro Ala Tyr Thr Ser
        115                 120                 125

Asp Asn Leu Pro Phe Leu Gly Phe Tyr His Met Ala Asn Ala Ala Leu
130                 135                 140

Asn Arg Leu Arg Gln Gln Ala Asn Leu Arg Asp Phe Tyr Asp Val Ile
145                 150                 155                 160

Val Glu Glu Val Arg Arg Met Thr Gly Phe Asp Arg Val Met Leu His
                165                 170                 175

Arg Phe Asp Glu Asn Asn His Gly Asp Val Ile Ala Glu Asp Lys Arg
            180                 185                 190

Asp Asp Met Glu Pro Tyr Leu Gly Leu His Tyr Pro Glu Ser Asp Ile
        195                 200                 205

Pro Gln Pro Ala Arg Arg Leu Phe Ile His Asn Pro Ile Arg Val Ile
210                 215                 220

Pro Asp Val Tyr Gly Val Ala Val Pro Leu Thr Pro Ala Val Asn Pro
225                 230                 235                 240

Ser Thr Asn Arg Ala Val Asp Leu Thr Glu Ser Ile Leu Arg Ser Ala
                245                 250                 255

Tyr His Cys His Leu Thr Tyr Leu Lys Asn Met Gly Val Gly Ala Ser
            260                 265                 270

Leu Thr Ile Ser Leu Ile Lys Asp Gly His Leu Trp Gly Leu Ile Ala
        275                 280                 285

Cys His His Gln Thr Pro Lys Val Ile Pro Phe Glu Leu Arg Lys Ala
290                 295                 300

Cys Glu Phe Phe Gly Arg Val Val Phe Ser Asn Ile Ser Ala Gln Glu
305                 310                 315                 320

Asp Thr Glu Thr Phe Asp Tyr Arg Val Gln Leu Ala Glu His Glu Ala
                325                 330                 335

Val Leu Leu Asp Lys Met Thr Thr Ala Ala Asp Phe Val Glu Gly Leu
            340                 345                 350

Thr Asn His Pro Asp Arg Leu Leu Gly Leu Thr Gly Ser Gln Gly Ala
        355                 360                 365

Ala Ile Cys Phe Gly Glu Lys Leu Ile Leu Val Gly Glu Thr Pro Asp
370                 375                 380

Glu Lys Ala Val Gln Tyr Leu Leu Gln Trp Leu Glu Asn Arg Glu Val
385                 390                 395                 400

Gln Asp Val Phe Phe Thr Ser Ser Leu Ser Gln Ile Tyr Pro Asp Ala
                405                 410                 415

Val Asn Phe Lys Ser Val Ala Ser Gly Leu Leu Ala Ile Pro Ile Ala
            420                 425                 430

Arg His Asn Phe Leu Leu Trp Phe Arg Pro Glu Val Leu Gln Thr Val
        435                 440                 445

Asn Trp Gly Gly Asp Pro Asn His Ala Tyr Glu Ala Thr Gln Glu Asp
450                 455                 460

Gly Lys Ile Glu Leu His Pro Arg Gln Ser Phe Asp Leu Trp Lys Glu
465                 470                 475                 480

Ile Val Arg Leu Gln Ser Leu Pro Trp Gln Ser Val Glu Ile Gln Ser
```

```
                        485                 490                 495
Ala Leu Ala Leu Lys Lys Ala Ile Val Asn Leu Ile Leu Arg Gln Ala
                500                 505                 510
Glu Glu Gln Ala Tyr Val Glu Gln Lys Leu Ile Ser Glu Glu Asp Leu
            515                 520                 525
Asn Ser Ala Val Asp His His His His His
        530                 535

<210> SEQ ID NO 38
<211> LENGTH: 375
<212> TYPE: PRT
<213> ORGANISM: Syncechocystis sp.

<400> SEQUENCE: 38

Met Ala Thr Thr Val Gln Leu Ser Asp Gln Ser Leu Arg Gln Leu Glu
1               5                   10                  15
Thr Leu Ala Ile His Thr Ala His Leu Ile Gln Pro His Gly Leu Val
            20                  25                  30
Val Val Leu Gln Glu Pro Asp Leu Thr Ile Ser Gln Ile Ser Ala Asn
        35                  40                  45
Cys Thr Gly Ile Leu Gly Arg Ser Pro Glu Asp Leu Leu Gly Arg Thr
    50                  55                  60
Leu Gly Glu Val Phe Asp Ser Phe Gln Ile Asp Pro Ile Gln Ser Arg
65                  70                  75                  80
Leu Thr Ala Gly Gln Ile Ser Ser Leu Asn Pro Ser Lys Leu Trp Ala
                85                  90                  95
Arg Val Met Gly Asp Asp Phe Val Ile Phe Asp Gly Val Phe His Arg
            100                 105                 110
Asn Ser Asp Gly Leu Leu Val Cys Glu Leu Glu Pro Ala Tyr Thr Ser
        115                 120                 125
Asp Asn Leu Pro Phe Leu Gly Phe Tyr His Met Ala Asn Ala Ala Leu
    130                 135                 140
Asn Arg Leu Arg Gln Gln Ala Asn Leu Arg Asp Phe Tyr Asp Val Ile
145                 150                 155                 160
Val Glu Glu Val Arg Arg Met Thr Gly Phe Asp Arg Val Met Leu Tyr
                165                 170                 175
Arg Phe Asp Glu Asn Asn His Gly Asp Val Ile Ala Glu Asp Lys Arg
            180                 185                 190
Asp Asp Met Glu Pro Tyr Leu Gly Leu His Tyr Pro Glu Ser Asp Ile
        195                 200                 205
Pro Gln Pro Ala Arg Arg Leu Phe Ile His Asn Pro Ile Arg Val Ile
    210                 215                 220
Pro Asp Val Tyr Gly Val Ala Val Pro Leu Thr Pro Ala Val Asn Pro
225                 230                 235                 240
Ser Thr Asn Arg Ala Val Asp Leu Thr Glu Ser Ile Leu Arg Ser Ala
                245                 250                 255
Tyr His Cys His Leu Thr Tyr Leu Lys Asn Met Gly Val Gly Ala Ser
            260                 265                 270
Leu Thr Ile Ser Leu Ile Lys Asp Gly His Leu Trp Gly Leu Ile Ala
        275                 280                 285
Cys His His Gln Thr Pro Lys Val Ile Pro Phe Glu Leu Arg Lys Ala
    290                 295                 300
Cys Glu Phe Phe Gly Arg Val Val Phe Ser Asn Ile Ser Ala Gln Glu
305                 310                 315                 320
```

Asp Thr Glu Thr Phe Asp Tyr Arg Val Gln Leu Ala Glu His Glu Ala
            325                 330                 335

Val Leu Leu Asp Lys Met Thr Thr Ala Ala Asp Phe Val Glu Glu Ala
            340                 345                 350

Tyr Val Glu Gln Lys Leu Ile Ser Glu Glu Asp Leu Asn Ser Ala Val
            355                 360                 365

Asp His His His His His
            370                 375

<210> SEQ ID NO 39
<211> LENGTH: 375
<212> TYPE: PRT
<213> ORGANISM: Syncechocystis sp.

<400> SEQUENCE: 39

Met Ala Thr Thr Val Gln Leu Ser Asp Gln Ser Leu Arg Gln Leu Glu
1               5                   10                  15

Thr Leu Ala Ile His Thr Ala His Leu Ile Gln Pro His Gly Leu Val
            20                  25                  30

Val Val Leu Gln Glu Pro Asp Leu Thr Ile Ser Gln Ile Ser Ala Asn
            35                  40                  45

Cys Thr Gly Ile Leu Gly Arg Ser Pro Glu Asp Leu Leu Gly Arg Thr
        50                  55                  60

Leu Gly Glu Val Phe Asp Ser Phe Gln Ile Asp Pro Ile Gln Ser Arg
65                  70                  75                  80

Leu Thr Ala Gly Gln Ile Ser Ser Leu Asn Pro Ser Lys Leu Trp Ala
                85                  90                  95

Arg Val Met Gly Asp Asp Phe Val Ile Phe Asp Gly Val Phe His Arg
            100                 105                 110

Asn Ser Asp Gly Leu Leu Val Cys Glu Leu Glu Pro Ala Tyr Thr Ser
        115                 120                 125

Asp Asn Leu Pro Phe Leu Gly Phe Tyr His Met Ala Asn Ala Ala Leu
    130                 135                 140

Asn Arg Leu Arg Gln Gln Ala Asn Leu Arg Asp Phe Tyr Asp Val Ile
145                 150                 155                 160

Val Glu Glu Val Arg Arg Met Thr Gly Phe Asp Arg Val Met Leu His
                165                 170                 175

Arg Phe Asp Glu Asn Asn His Gly Asp Val Ile Ala Glu Asp Lys Arg
            180                 185                 190

Asp Asp Met Glu Pro Tyr Leu Gly Leu His Tyr Pro Glu Ser Asp Ile
        195                 200                 205

Pro Gln Pro Ala Arg Arg Leu Phe Ile His Asn Pro Ile Arg Val Ile
    210                 215                 220

Pro Asp Val Tyr Gly Val Ala Val Pro Leu Thr Pro Ala Val Asn Pro
225                 230                 235                 240

Ser Thr Asn Arg Ala Val Asp Leu Thr Glu Ser Ile Leu Arg Ser Ala
                245                 250                 255

Tyr His Cys His Leu Thr Tyr Leu Lys Asn Met Gly Val Gly Ala Ser
            260                 265                 270

Leu Thr Ile Ser Leu Ile Lys Asp Gly His Leu Trp Gly Leu Ile Ala
        275                 280                 285

Cys His His Gln Thr Pro Lys Val Ile Pro Phe Glu Leu Arg Lys Ala
    290                 295                 300

Cys Glu Phe Phe Gly Arg Val Val Phe Ser Asn Ile Ser Ala Gln Glu
305                 310                 315                 320

```
Asp Thr Glu Thr Phe Asp Tyr Arg Val Gln Leu Ala Glu His Glu Ala
            325                 330                 335

Val Leu Leu Asp Lys Met Thr Thr Ala Ala Asp Phe Val Glu Glu Ala
            340                 345                 350

Tyr Val Glu Gln Lys Leu Ile Ser Glu Glu Asp Leu Asn Ser Ala Val
            355                 360                 365

Asp His His His His His His
            370                 375

<210> SEQ ID NO 40
<211> LENGTH: 390
<212> TYPE: PRT
<213> ORGANISM: Syncechocystis sp.

<400> SEQUENCE: 40

Met Ala Asn Leu Arg Asp Phe Tyr Asp Val Ile Val Glu Glu Val Arg
1               5                   10                  15

Arg Met Thr Gly Phe Asp Arg Val Met Leu Tyr Arg Phe Asp Glu Asn
            20                  25                  30

Asn His Gly Asp Val Ile Ala Glu Asp Lys Arg Asp Asp Met Glu Pro
        35                  40                  45

Tyr Leu Gly Leu His Tyr Pro Glu Ser Asp Ile Pro Gln Pro Ala Arg
    50                  55                  60

Arg Leu Phe Ile His Asn Pro Ile Arg Val Ile Pro Asp Val Tyr Gly
65                  70                  75                  80

Val Ala Val Pro Leu Thr Pro Ala Val Asn Pro Ser Thr Asn Arg Ala
                85                  90                  95

Val Asp Leu Thr Glu Ser Ile Leu Arg Ser Ala Tyr His Cys His Leu
            100                 105                 110

Thr Tyr Leu Lys Asn Met Gly Val Gly Ala Ser Leu Thr Ile Ser Leu
        115                 120                 125

Ile Lys Asp Gly His Leu Trp Gly Leu Ile Ala Cys His His Gln Thr
130                 135                 140

Pro Lys Val Ile Pro Phe Glu Leu Arg Lys Ala Cys Glu Phe Phe Gly
145                 150                 155                 160

Arg Val Val Phe Ser Asn Ile Ser Ala Gln Glu Asp Thr Glu Thr Phe
                165                 170                 175

Asp Tyr Arg Val Gln Leu Ala Glu His Glu Ala Val Leu Leu Asp Lys
            180                 185                 190

Met Thr Thr Ala Ala Asp Phe Val Glu Gly Leu Thr Asn His Pro Asp
        195                 200                 205

Arg Leu Leu Gly Leu Thr Gly Ser Gln Gly Ala Ala Ile Cys Phe Gly
    210                 215                 220

Glu Lys Leu Ile Leu Val Gly Glu Thr Pro Asp Glu Lys Ala Val Gln
225                 230                 235                 240

Tyr Leu Leu Gln Trp Leu Glu Asn Arg Glu Val Gln Asp Val Phe Phe
                245                 250                 255

Thr Ser Ser Leu Ser Gln Ile Tyr Pro Asp Ala Val Asn Phe Lys Ser
            260                 265                 270

Val Ala Ser Gly Leu Leu Ala Ile Pro Ile Ala Arg His Asn Phe Leu
        275                 280                 285

Leu Trp Phe Arg Pro Glu Val Leu Gln Thr Val Asn Trp Gly Gly Asp
    290                 295                 300

Pro Asn His Ala Tyr Glu Ala Thr Gln Glu Asp Gly Lys Ile Glu Leu
```

```
                305                 310                 315                 320
His Pro Arg Gln Ser Phe Asp Leu Trp Lys Glu Ile Val Arg Leu Gln
                    325                 330                 335

Ser Leu Pro Trp Gln Ser Val Glu Ile Gln Ser Ala Leu Ala Leu Lys
                340                 345                 350

Lys Ala Ile Val Asn Leu Ile Leu Arg Gln Ala Glu Glu Gln Ala Tyr
                    355                 360                 365

Val Glu Gln Lys Leu Ile Ser Glu Glu Asp Leu Asn Ser Ala Val Asp
                370                 375                 380

His His His His His His
385                 390

<210> SEQ ID NO 41
<211> LENGTH: 226
<212> TYPE: PRT
<213> ORGANISM: Syncechocystis sp.

<400> SEQUENCE: 41

Met Ala Asn Leu Arg Asp Phe Tyr Asp Val Ile Val Glu Glu Val Arg
1               5                   10                  15

Arg Met Thr Gly Phe Asp Arg Val Met Leu Tyr Arg Phe Asp Glu Asn
                    20                  25                  30

Asn His Gly Asp Val Ile Ala Glu Asp Lys Arg Asp Asp Met Glu Pro
                35                  40                  45

Tyr Leu Gly Leu His Tyr Pro Glu Ser Asp Ile Pro Gln Pro Ala Arg
            50                  55                  60

Arg Leu Phe Ile His Asn Pro Ile Arg Val Ile Pro Asp Val Tyr Gly
65                  70                  75                  80

Val Ala Val Pro Leu Thr Pro Ala Val Asn Pro Ser Thr Asn Arg Ala
                    85                  90                  95

Val Asp Leu Thr Glu Ser Ile Leu Arg Ser Ala Tyr His Cys His Leu
                100                 105                 110

Thr Tyr Leu Lys Asn Met Gly Val Gly Ala Ser Leu Thr Ile Ser Leu
                115                 120                 125

Ile Lys Asp Gly His Leu Trp Gly Leu Ile Ala Cys His His Gln Thr
130                 135                 140

Pro Lys Val Ile Pro Phe Glu Leu Arg Lys Ala Cys Glu Phe Phe Gly
145                 150                 155                 160

Arg Val Val Phe Ser Asn Ile Ser Ala Gln Glu Asp Thr Glu Thr Phe
                    165                 170                 175

Asp Tyr Arg Val Gln Leu Ala Glu His Glu Ala Val Leu Leu Asp Lys
                180                 185                 190

Met Thr Thr Ala Ala Asp Phe Val Glu Glu Ala Tyr Val Glu Gln Lys
                195                 200                 205

Leu Ile Ser Glu Glu Asp Leu Asn Ser Ala Val Asp His His His His
            210                 215                 220

His His
225

<210> SEQ ID NO 42
<211> LENGTH: 539
<212> TYPE: PRT
<213> ORGANISM: Syncechocystis sp.

<400> SEQUENCE: 42

Met Ala Thr Thr Val Gln Leu Ser Asp Gln Ser Leu Arg Gln Leu Glu
```

-continued

```
  1               5              10              15
Thr Leu Ala Ile His Thr Ala His Leu Ile Gln Pro His Gly Leu Val
             20              25              30
Val Val Leu Gln Glu Pro Asp Leu Thr Ile Ser Gln Ile Ser Ala Asn
             35              40              45
Cys Thr Gly Ile Leu Gly Arg Ser Pro Glu Asp Leu Leu Gly Arg Thr
             50              55              60
Leu Gly Glu Val Phe Asp Ser Phe Gln Ile Asp Pro Ile Gln Ser Arg
 65              70              75              80
Leu Thr Ala Gly Gln Ile Ser Ser Leu Asn Pro Ser Lys Leu Trp Ala
             85              90              95
Arg Val Met Gly Asp Asp Phe Val Ile Phe Asp Gly Val Phe His Arg
             100             105             110
Asn Ser Asp Gly Leu Leu Val Cys Glu Leu Glu Pro Ala Tyr Thr Ser
             115             120             125
Asp Asn Leu Pro Phe Leu Gly Phe Tyr His Met Ala Asn Ala Ala Leu
             130             135             140
Asn Arg Leu Arg Gln Gln Ala Asn Leu Arg Asp Phe Tyr Asp Val Ile
145             150             155             160
Val Glu Glu Val Arg Arg Met Thr Gly Phe Asp Arg Val Met Leu His
             165             170             175
Arg Phe Asp Glu Asn Asn His Gly Asp Val Ile Ala Glu Asp Lys Arg
             180             185             190
Asp Asp Met Glu Pro Tyr Leu Gly Leu His Tyr Pro Glu Ser Asp Ile
             195             200             205
Pro Gln Pro Ala Arg Arg Leu Phe Ile His Asn Pro Ile Arg Val Ile
             210             215             220
Pro Asp Val Tyr Gly Val Ala Val Pro Leu Thr Pro Ala Val Asn Pro
225             230             235             240
Ser Thr Asn Arg Ala Val Asp Leu Thr Glu Ser Ile Leu Arg Ser Ala
             245             250             255
Tyr His Cys His Leu Thr Tyr Leu Lys Asn Met Gly Val Gly Ala Ser
             260             265             270
Leu Thr Ile Ser Leu Ile Lys Asp Gly His Leu Trp Gly Leu Ile Ala
             275             280             285
Cys His His Gln Thr Pro Lys Val Ile Pro Phe Glu Leu Arg Lys Ala
             290             295             300
Cys Glu Phe Phe Gly Arg Val Val Phe Ser Asn Ile Ser Ala Gln Glu
305             310             315             320
Asp Thr Glu Thr Phe Asp Tyr Arg Val Gln Leu Ala Glu His Glu Ala
             325             330             335
Val Leu Leu Asp Lys Met Thr Thr Ala Ala Asp Phe Val Glu Gly Leu
             340             345             350
Thr Asn His Pro Asp Arg Leu Leu Gly Leu Thr Gly Ser Gln Gly Ala
             355             360             365
Ala Ile Cys Phe Gly Glu Lys Leu Ile Leu Val Gly Glu Thr Pro Asp
             370             375             380
Glu Lys Ala Val Gln Tyr Leu Leu Gln Trp Leu Glu Asn Arg Glu Val
385             390             395             400
Gln Asp Val Phe Phe Thr Ser Ser Leu Ser Gln Ile Tyr Pro Asp Ala
             405             410             415
Val Asn Phe Lys Ser Val Ala Ser Gly Leu Leu Ala Ile Pro Ile Ala
             420             425             430
```

```
Arg His Asn Phe Leu Leu Trp Phe Arg Pro Glu Val Leu Gln Thr Val
            435                 440                 445

Asn Trp Gly Gly Asp Pro Asn His Ala Tyr Glu Ala Thr Gln Glu Asp
            450                 455                 460

Gly Lys Ile Glu Leu His Pro Arg Gln Ser Phe Asp Leu Trp Lys Glu
465                 470                 475                 480

Ile Val Arg Leu Gln Ser Leu Pro Trp Gln Ser Val Glu Ile Gln Ser
                485                 490                 495

Ala Leu Ala Leu Lys Lys Ala Ile Val Asn Leu Ile Leu Arg Gln Ala
            500                 505                 510

Glu Glu Gln Ala Tyr Val Glu Gln Lys Leu Ile Ser Glu Glu Asp Leu
            515                 520                 525

Asn Ser Ala Val Asp His His His His His
            530                 535

<210> SEQ ID NO 43
<211> LENGTH: 539
<212> TYPE: PRT
<213> ORGANISM: Syncechocystis sp.

<400> SEQUENCE: 43

Met Ala Thr Thr Val Gln Leu Ser Asp Gln Ser Leu Arg Gln Leu Glu
1               5                   10                  15

Thr Leu Ala Ile His Thr Ala His Leu Ile Gln Pro His Gly Leu Val
                20                  25                  30

Val Val Leu Gln Glu Pro Asp Leu Thr Ile Ser Gln Ile Ser Ala Asn
            35                  40                  45

Cys Thr Gly Ile Leu Gly Arg Ser Pro Glu Asp Leu Leu Gly Arg Thr
        50                  55                  60

Leu Gly Glu Val Phe Asp Ser Phe Gln Ile Asp Pro Ile Gln Ser Arg
65                  70                  75                  80

Leu Thr Ala Gly Gln Ile Ser Ser Leu Asn Pro Ser Lys Leu Trp Ala
                85                  90                  95

Arg Val Met Gly Asp Asp Phe Val Ile Phe Asp Gly Val Phe His Arg
            100                 105                 110

Asn Ser Asp Gly Leu Leu Val Cys Glu Leu Glu Pro Ala Tyr Thr Ser
            115                 120                 125

Asp Asn Leu Pro Phe Leu Gly Phe Tyr His Met Ala Asn Ala Ala Leu
        130                 135                 140

Asn Arg Leu Arg Gln Gln Ala Asn Leu Arg Asp Phe Tyr Asp Val Ile
145                 150                 155                 160

Val Glu Glu Val Arg Arg Met Thr Gly Phe Asp Arg Val Met Leu Ala
                165                 170                 175

Arg Phe Asp Glu Asn Asn His Gly Asp Val Ile Ala Glu Asp Lys Arg
            180                 185                 190

Asp Asp Met Glu Pro Tyr Leu Gly Leu His Tyr Pro Glu Ser Asp Ile
            195                 200                 205

Pro Gln Pro Ala Arg Arg Leu Phe Ile His Asn Pro Ile Arg Val Ile
        210                 215                 220

Pro Asp Val Tyr Gly Val Ala Val Pro Leu Thr Pro Ala Val Asn Pro
225                 230                 235                 240

Ser Thr Asn Arg Ala Val Asp Leu Thr Glu Ser Ile Leu Arg Ser Ala
                245                 250                 255

Tyr His Cys His Leu Thr Tyr Leu Lys Asn Met Gly Val Gly Ala Ser
```

-continued

```
                260                 265                 270
Leu Thr Ile Ser Leu Ile Lys Asp Gly His Leu Trp Gly Leu Ile Ala
            275                 280                 285
Cys His His Gln Thr Pro Lys Val Ile Pro Phe Glu Leu Arg Lys Ala
        290                 295                 300
Cys Glu Phe Phe Gly Arg Val Val Phe Ser Asn Ile Ser Ala Gln Glu
305                 310                 315                 320
Asp Thr Glu Thr Phe Asp Tyr Arg Val Gln Leu Ala Glu His Glu Ala
                325                 330                 335
Val Leu Leu Asp Lys Met Thr Thr Ala Ala Asp Phe Val Glu Gly Leu
            340                 345                 350
Thr Asn His Pro Asp Arg Leu Leu Gly Leu Thr Gly Ser Gln Gly Ala
        355                 360                 365
Ala Ile Cys Phe Gly Glu Lys Leu Ile Leu Val Gly Glu Thr Pro Asp
    370                 375                 380
Glu Lys Ala Val Gln Tyr Leu Leu Gln Trp Leu Glu Asn Arg Glu Val
385                 390                 395                 400
Gln Asp Val Phe Phe Thr Ser Ser Leu Ser Gln Ile Tyr Pro Asp Ala
                405                 410                 415
Val Asn Phe Lys Ser Val Ala Ser Gly Leu Leu Ala Ile Pro Ile Ala
            420                 425                 430
Arg His Asn Phe Leu Leu Trp Phe Arg Pro Glu Val Leu Gln Thr Val
        435                 440                 445
Asn Trp Gly Gly Asp Pro Asn His Ala Tyr Glu Ala Thr Gln Glu Asp
    450                 455                 460
Gly Lys Ile Glu Leu His Pro Arg Gln Ser Phe Asp Leu Trp Lys Glu
465                 470                 475                 480
Ile Val Arg Leu Gln Ser Leu Pro Trp Gln Ser Val Glu Ile Gln Ser
                485                 490                 495
Ala Leu Ala Leu Lys Lys Ala Ile Val Asn Leu Ile Leu Arg Gln Ala
            500                 505                 510
Glu Glu Gln Ala Tyr Val Glu Gln Lys Leu Ile Ser Glu Glu Asp Leu
        515                 520                 525
Asn Ser Ala Val Asp His His His His His His
    530                 535
```

<210> SEQ ID NO 44
<211> LENGTH: 539
<212> TYPE: PRT
<213> ORGANISM: Syncechocystis sp.

<400> SEQUENCE: 44

```
Met Ala Thr Thr Val Gln Leu Ser Asp Gln Ser Leu Arg Gln Leu Glu
1               5                   10                  15
Thr Leu Ala Ile His Thr Ala Leu Ile Gln Pro His Gly Leu Val
            20                  25                  30
Val Val Leu Gln Glu Pro Asp Leu Thr Ile Ser Gln Ile Ser Ala Asn
        35                  40                  45
Cys Thr Gly Ile Leu Gly Arg Ser Pro Glu Asp Leu Leu Gly Arg Thr
    50                  55                  60
Leu Gly Glu Val Phe Asp Ser Phe Gln Ile Asp Pro Ile Gln Ser Arg
65                  70                  75                  80
Leu Thr Ala Gly Gln Ile Ser Ser Leu Asn Pro Ser Lys Leu Trp Ala
                85                  90                  95
```

```
Arg Val Met Gly Asp Asp Phe Val Ile Phe Asp Gly Val Phe His Arg
                100                 105                 110

Asn Ser Asp Gly Leu Leu Val Cys Glu Leu Glu Pro Ala Tyr Thr Ser
            115                 120                 125

Asp Asn Leu Pro Phe Leu Gly Phe Tyr His Met Ala Asn Ala Ala Leu
        130                 135                 140

Asn Arg Leu Arg Gln Gln Ala Asn Leu Arg Asp Phe Tyr Asp Val Ile
145                 150                 155                 160

Val Glu Glu Val Arg Arg Met Thr Gly Phe Asp Arg Val Met Leu Cys
                165                 170                 175

Arg Phe Asp Glu Asn Asn His Gly Asp Val Ile Ala Glu Asp Lys Arg
            180                 185                 190

Asp Asp Met Glu Pro Tyr Leu Gly Leu His Tyr Pro Glu Ser Asp Ile
        195                 200                 205

Pro Gln Pro Ala Arg Arg Leu Phe Ile His Asn Pro Ile Arg Val Ile
    210                 215                 220

Pro Asp Val Tyr Gly Val Ala Val Pro Leu Thr Pro Ala Val Asn Pro
225                 230                 235                 240

Ser Thr Asn Arg Ala Val Asp Leu Thr Glu Ser Ile Leu Arg Ser Ala
                245                 250                 255

Tyr His Cys His Leu Thr Tyr Leu Lys Asn Met Gly Val Gly Ala Ser
            260                 265                 270

Leu Thr Ile Ser Leu Ile Lys Asp Gly His Leu Trp Gly Leu Ile Ala
        275                 280                 285

Cys His His Gln Thr Pro Lys Val Ile Pro Phe Glu Leu Arg Lys Ala
    290                 295                 300

Cys Glu Phe Phe Gly Arg Val Phe Ser Asn Ile Ser Ala Gln Glu
305                 310                 315                 320

Asp Thr Glu Thr Phe Asp Tyr Arg Val Gln Leu Ala Glu His Glu Ala
                325                 330                 335

Val Leu Leu Asp Lys Met Thr Thr Ala Ala Asp Phe Val Glu Gly Leu
            340                 345                 350

Thr Asn His Pro Asp Arg Leu Leu Gly Leu Thr Gly Ser Gln Gly Ala
        355                 360                 365

Ala Ile Cys Phe Gly Glu Lys Leu Ile Leu Val Gly Glu Thr Pro Asp
    370                 375                 380

Glu Lys Ala Val Gln Tyr Leu Leu Gln Trp Leu Glu Asn Arg Glu Val
385                 390                 395                 400

Gln Asp Val Phe Phe Thr Ser Ser Leu Ser Gln Ile Tyr Pro Asp Ala
                405                 410                 415

Val Asn Phe Lys Ser Val Ala Ser Gly Leu Leu Ala Ile Pro Ile Ala
            420                 425                 430

Arg His Asn Phe Leu Leu Trp Phe Arg Pro Glu Val Leu Gln Thr Val
        435                 440                 445

Asn Trp Gly Gly Asp Pro Asn His Ala Tyr Glu Ala Thr Gln Glu Asp
    450                 455                 460

Gly Lys Ile Glu Leu His Pro Arg Gln Ser Phe Asp Leu Trp Lys Glu
465                 470                 475                 480

Ile Val Arg Leu Gln Ser Leu Pro Trp Gln Ser Val Glu Ile Gln Ser
                485                 490                 495

Ala Leu Ala Leu Lys Lys Ala Ile Val Asn Leu Ile Leu Arg Gln Ala
            500                 505                 510

Glu Glu Gln Ala Tyr Val Glu Gln Lys Leu Ile Ser Glu Glu Asp Leu
```

```
                515                 520                 525
Asn Ser Ala Val Asp His His His His His
    530                 535

<210> SEQ ID NO 45
<211> LENGTH: 539
<212> TYPE: PRT
<213> ORGANISM: Syncechocystis sp.

<400> SEQUENCE: 45

Met Ala Thr Thr Val Gln Leu Ser Asp Gln Ser Leu Arg Gln Leu Glu
1               5                   10                  15

Thr Leu Ala Ile His Thr Ala His Leu Ile Gln Pro His Gly Leu Val
            20                  25                  30

Val Val Leu Gln Glu Pro Asp Leu Thr Ile Ser Gln Ile Ser Ala Asn
        35                  40                  45

Cys Thr Gly Ile Leu Gly Arg Ser Pro Glu Asp Leu Leu Gly Arg Thr
    50                  55                  60

Leu Gly Glu Val Phe Asp Ser Phe Gln Ile Asp Pro Ile Gln Ser Arg
65                  70                  75                  80

Leu Thr Ala Gly Gln Ile Ser Ser Leu Asn Pro Ser Lys Leu Trp Ala
                85                  90                  95

Arg Val Met Gly Asp Asp Phe Val Ile Phe Asp Gly Val Phe His Arg
            100                 105                 110

Asn Ser Asp Gly Leu Leu Val Cys Glu Leu Glu Pro Ala Tyr Thr Ser
        115                 120                 125

Asp Asn Leu Pro Phe Leu Gly Phe Tyr His Met Ala Asn Ala Ala Leu
    130                 135                 140

Asn Arg Leu Arg Gln Gln Ala Asn Leu Arg Asp Phe Tyr Asp Val Ile
145                 150                 155                 160

Val Glu Glu Val Arg Arg Met Thr Gly Phe Asp Arg Val Met Leu Glu
                165                 170                 175

Arg Phe Asp Glu Asn Asn His Gly Asp Val Ile Ala Glu Asp Lys Arg
            180                 185                 190

Asp Asp Met Glu Pro Tyr Leu Gly Leu His Tyr Pro Glu Ser Asp Ile
        195                 200                 205

Pro Gln Pro Ala Arg Arg Leu Phe Ile His Asn Pro Ile Arg Val Ile
    210                 215                 220

Pro Asp Val Tyr Gly Val Ala Val Pro Leu Thr Pro Ala Val Asn Pro
225                 230                 235                 240

Ser Thr Asn Arg Ala Val Asp Leu Thr Glu Ser Ile Leu Arg Ser Ala
                245                 250                 255

Tyr His Cys His Leu Thr Tyr Leu Lys Asn Met Gly Val Gly Ala Ser
            260                 265                 270

Leu Thr Ile Ser Leu Ile Lys Asp Gly His Leu Trp Gly Leu Ile Ala
        275                 280                 285

Cys His His Gln Thr Pro Lys Val Ile Pro Phe Glu Leu Arg Lys Ala
    290                 295                 300

Cys Glu Phe Phe Gly Arg Val Val Phe Ser Asn Ile Ser Ala Gln Glu
305                 310                 315                 320

Asp Thr Glu Thr Phe Asp Tyr Arg Val Gln Leu Ala Glu His Glu Ala
                325                 330                 335

Val Leu Leu Asp Lys Met Thr Thr Ala Ala Asp Phe Val Glu Gly Leu
            340                 345                 350
```

```
Thr Asn His Pro Asp Arg Leu Leu Gly Leu Thr Gly Ser Gln Gly Ala
        355                 360                 365

Ala Ile Cys Phe Gly Glu Lys Leu Ile Leu Val Gly Glu Thr Pro Asp
    370                 375                 380

Glu Lys Ala Val Gln Tyr Leu Leu Gln Trp Leu Glu Asn Arg Glu Val
385                 390                 395                 400

Gln Asp Val Phe Phe Thr Ser Ser Leu Ser Gln Ile Tyr Pro Asp Ala
                405                 410                 415

Val Asn Phe Lys Ser Val Ala Ser Gly Leu Leu Ala Ile Pro Ile Ala
                420                 425                 430

Arg His Asn Phe Leu Leu Trp Phe Arg Pro Glu Val Leu Gln Thr Val
            435                 440                 445

Asn Trp Gly Gly Asp Pro Asn His Ala Tyr Glu Ala Thr Gln Glu Asp
    450                 455                 460

Gly Lys Ile Glu Leu His Pro Arg Gln Ser Phe Asp Leu Trp Lys Glu
465                 470                 475                 480

Ile Val Arg Leu Gln Ser Leu Pro Trp Gln Ser Val Glu Ile Gln Ser
                485                 490                 495

Ala Leu Ala Leu Lys Lys Ala Ile Val Asn Leu Ile Leu Arg Gln Ala
            500                 505                 510

Glu Glu Gln Ala Tyr Val Glu Gln Lys Leu Ile Ser Glu Glu Asp Leu
    515                 520                 525

Asn Ser Ala Val Asp His His His His His His
        530                 535

<210> SEQ ID NO 46
<211> LENGTH: 539
<212> TYPE: PRT
<213> ORGANISM: Syncechocystis sp.

<400> SEQUENCE: 46

Met Ala Thr Thr Val Gln Leu Ser Asp Gln Ser Leu Arg Gln Leu Glu
1               5                   10                  15

Thr Leu Ala Ile His Thr Ala His Leu Ile Gln Pro His Gly Leu Val
            20                  25                  30

Val Val Leu Gln Glu Pro Asp Leu Thr Ile Ser Gln Ile Ser Ala Asn
        35                  40                  45

Cys Thr Gly Ile Leu Gly Arg Ser Pro Glu Asp Leu Leu Gly Arg Thr
    50                  55                  60

Leu Gly Glu Val Phe Asp Ser Phe Gln Ile Asp Pro Ile Gln Ser Arg
65                  70                  75                  80

Leu Thr Ala Gly Gln Ile Ser Ser Leu Asn Pro Ser Lys Leu Trp Ala
                85                  90                  95

Arg Val Met Gly Asp Asp Phe Val Ile Phe Asp Gly Val Phe His Arg
            100                 105                 110

Asn Ser Asp Gly Leu Leu Val Cys Glu Leu Glu Pro Ala Tyr Thr Ser
        115                 120                 125

Asp Asn Leu Pro Phe Leu Gly Phe Tyr His Met Ala Asn Ala Ala Leu
    130                 135                 140

Asn Arg Leu Arg Gln Gln Ala Asn Leu Arg Asp Phe Tyr Asp Val Ile
145                 150                 155                 160

Val Glu Glu Val Arg Arg Met Thr Gly Phe Asp Arg Val Met Leu Phe
                165                 170                 175

Arg Phe Asp Glu Asn Asn His Gly Asp Val Ile Ala Glu Asp Lys Arg
            180                 185                 190
```

```
Asp Asp Met Glu Pro Tyr Leu Gly Leu His Tyr Pro Glu Ser Asp Ile
        195                 200                 205

Pro Gln Pro Ala Arg Arg Leu Phe Ile His Asn Pro Ile Arg Val Ile
    210                 215                 220

Pro Asp Val Tyr Gly Val Ala Val Pro Leu Thr Pro Ala Val Asn Pro
225                 230                 235                 240

Ser Thr Asn Arg Ala Val Asp Leu Thr Glu Ser Ile Leu Arg Ser Ala
                245                 250                 255

Tyr His Cys His Leu Thr Tyr Leu Lys Asn Met Gly Val Gly Ala Ser
            260                 265                 270

Leu Thr Ile Ser Leu Ile Lys Asp Gly His Leu Trp Gly Leu Ile Ala
        275                 280                 285

Cys His His Gln Thr Pro Lys Val Ile Pro Phe Glu Leu Arg Lys Ala
    290                 295                 300

Cys Glu Phe Phe Gly Arg Val Val Phe Ser Asn Ile Ser Ala Gln Glu
305                 310                 315                 320

Asp Thr Glu Thr Phe Asp Tyr Arg Val Gln Leu Ala Glu His Glu Ala
                325                 330                 335

Val Leu Leu Asp Lys Met Thr Thr Ala Ala Asp Phe Val Glu Gly Leu
            340                 345                 350

Thr Asn His Pro Asp Arg Leu Leu Gly Leu Thr Gly Ser Gln Gly Ala
        355                 360                 365

Ala Ile Cys Phe Gly Glu Lys Leu Ile Leu Val Gly Glu Thr Pro Asp
    370                 375                 380

Glu Lys Ala Val Gln Tyr Leu Leu Gln Trp Leu Glu Asn Arg Glu Val
385                 390                 395                 400

Gln Asp Val Phe Phe Thr Ser Ser Leu Ser Gln Ile Tyr Pro Asp Ala
                405                 410                 415

Val Asn Phe Lys Ser Val Ala Ser Gly Leu Leu Ala Ile Pro Ile Ala
            420                 425                 430

Arg His Asn Phe Leu Leu Trp Phe Arg Pro Glu Val Leu Gln Thr Val
        435                 440                 445

Asn Trp Gly Gly Asp Pro Asn His Ala Tyr Glu Ala Thr Gln Glu Asp
    450                 455                 460

Gly Lys Ile Glu Leu His Pro Arg Gln Ser Phe Asp Leu Trp Lys Glu
465                 470                 475                 480

Ile Val Arg Leu Gln Ser Leu Pro Trp Gln Ser Val Glu Ile Gln Ser
                485                 490                 495

Ala Leu Ala Leu Lys Lys Ala Ile Val Asn Leu Ile Leu Arg Gln Ala
            500                 505                 510

Glu Glu Gln Ala Tyr Val Glu Gln Lys Leu Ile Ser Glu Glu Asp Leu
        515                 520                 525

Asn Ser Ala Val Asp His His His His His
    530                 535

<210> SEQ ID NO 47
<211> LENGTH: 539
<212> TYPE: PRT
<213> ORGANISM: Syncechocystis sp.

<400> SEQUENCE: 47

Met Ala Thr Thr Val Gln Leu Ser Asp Gln Ser Leu Arg Gln Leu Glu
1               5                   10                  15

Thr Leu Ala Ile His Thr Ala His Leu Ile Gln Pro His Gly Leu Val
```

-continued

```
                     20                  25                  30
Val Val Leu Gln Glu Pro Asp Leu Thr Ile Ser Gln Ile Ser Ala Asn
             35                  40                  45
Cys Thr Gly Ile Leu Gly Arg Ser Pro Glu Asp Leu Leu Gly Arg Thr
         50                  55                  60
Leu Gly Glu Val Phe Asp Ser Phe Gln Ile Asp Pro Ile Gln Ser Arg
 65                  70                  75                  80
Leu Thr Ala Gly Gln Ile Ser Ser Leu Asn Pro Ser Lys Leu Trp Ala
                 85                  90                  95
Arg Val Met Gly Asp Asp Phe Val Ile Phe Asp Gly Val Phe His Arg
            100                 105                 110
Asn Ser Asp Gly Leu Leu Val Cys Glu Leu Glu Pro Ala Tyr Thr Ser
            115                 120                 125
Asp Asn Leu Pro Phe Leu Gly Phe Tyr His Met Ala Asn Ala Ala Leu
        130                 135                 140
Asn Arg Leu Arg Gln Ala Asn Leu Arg Asp Phe Tyr Asp Val Ile
145                 150                 155                 160
Val Glu Glu Val Arg Arg Met Thr Gly Phe Asp Arg Val Met Leu Gln
                165                 170                 175
Arg Phe Asp Glu Asn Asn His Gly Asp Val Ile Ala Glu Asp Lys Arg
            180                 185                 190
Asp Asp Met Glu Pro Tyr Leu Gly Leu His Tyr Pro Glu Ser Asp Ile
        195                 200                 205
Pro Gln Pro Ala Arg Arg Leu Phe Ile His Asn Pro Ile Arg Val Ile
    210                 215                 220
Pro Asp Val Tyr Gly Val Ala Val Pro Leu Thr Pro Ala Val Asn Pro
225                 230                 235                 240
Ser Thr Asn Arg Ala Val Asp Leu Thr Glu Ser Ile Leu Arg Ser Ala
                245                 250                 255
Tyr His Cys His Leu Thr Tyr Leu Lys Asn Met Gly Val Gly Ala Ser
            260                 265                 270
Leu Thr Ile Ser Leu Ile Lys Asp Gly His Leu Trp Gly Leu Ile Ala
        275                 280                 285
Cys His His Gln Thr Pro Lys Val Ile Pro Phe Glu Leu Arg Lys Ala
    290                 295                 300
Cys Glu Phe Phe Gly Arg Val Val Phe Ser Asn Ile Ser Ala Gln Glu
305                 310                 315                 320
Asp Thr Glu Thr Phe Asp Tyr Arg Val Gln Leu Ala Glu His Glu Ala
                325                 330                 335
Val Leu Leu Asp Lys Met Thr Thr Ala Ala Asp Phe Val Glu Gly Leu
            340                 345                 350
Thr Asn His Pro Asp Arg Leu Leu Gly Leu Thr Gly Ser Gln Gly Ala
        355                 360                 365
Ala Ile Cys Phe Gly Glu Lys Leu Ile Leu Val Gly Glu Thr Pro Asp
    370                 375                 380
Glu Lys Ala Val Gln Tyr Leu Leu Gln Trp Leu Glu Asn Arg Glu Val
385                 390                 395                 400
Gln Asp Val Phe Phe Thr Ser Ser Leu Ser Gln Ile Tyr Pro Asp Ala
                405                 410                 415
Val Asn Phe Lys Ser Val Ala Ser Gly Leu Leu Ala Ile Pro Ile Ala
            420                 425                 430
Arg His Asn Phe Leu Leu Trp Phe Arg Pro Glu Val Leu Gln Thr Val
        435                 440                 445
```

-continued

Asn Trp Gly Gly Asp Pro Asn His Ala Tyr Glu Ala Thr Gln Glu Asp
    450                 455                 460

Gly Lys Ile Glu Leu His Pro Arg Gln Ser Phe Asp Leu Trp Lys Glu
465                 470                 475                 480

Ile Val Arg Leu Gln Ser Leu Pro Trp Gln Ser Val Glu Ile Gln Ser
                485                 490                 495

Ala Leu Ala Leu Lys Lys Ala Ile Val Asn Leu Ile Leu Arg Gln Ala
            500                 505                 510

Glu Glu Gln Ala Tyr Val Glu Gln Lys Leu Ile Ser Glu Glu Asp Leu
        515                 520                 525

Asn Ser Ala Val Asp His His His His His
    530                 535

<210> SEQ ID NO 48
<211> LENGTH: 539
<212> TYPE: PRT
<213> ORGANISM: Syncechocystis sp.

<400> SEQUENCE: 48

Met Ala Thr Thr Val Gln Leu Ser Asp Gln Ser Leu Arg Gln Leu Glu
1               5                   10                  15

Thr Leu Ala Ile His Thr Ala His Leu Ile Gln Pro His Gly Leu Val
            20                  25                  30

Val Val Leu Gln Glu Pro Asp Leu Thr Ile Ser Gln Ile Ser Ala Asn
        35                  40                  45

Cys Thr Gly Ile Leu Gly Arg Ser Pro Glu Asp Leu Leu Gly Arg Thr
    50                  55                  60

Leu Gly Glu Val Phe Asp Ser Phe Gln Ile Asp Pro Ile Gln Ser Arg
65                  70                  75                  80

Leu Thr Ala Gly Gln Ile Ser Ser Leu Asn Pro Ser Lys Leu Trp Ala
                85                  90                  95

Arg Val Met Gly Asp Asp Phe Val Ile Phe Asp Gly Val Phe His Arg
            100                 105                 110

Asn Ser Asp Gly Leu Leu Val Cys Glu Leu Glu Pro Ala Tyr Thr Ser
        115                 120                 125

Asp Asn Leu Pro Phe Leu Gly Phe Tyr His Met Ala Asn Ala Ala Leu
    130                 135                 140

Asn Arg Leu Arg Gln Gln Ala Asn Leu Arg Asp Phe Tyr Asp Val Ile
145                 150                 155                 160

Val Glu Glu Val Arg Arg Met Thr Gly Phe Asp Arg Val Met Leu Ser
                165                 170                 175

Arg Phe Asp Glu Asn Asn His Gly Asp Val Ile Ala Glu Asp Lys Arg
            180                 185                 190

Asp Asp Met Glu Pro Tyr Leu Gly Leu His Tyr Pro Glu Ser Asp Ile
        195                 200                 205

Pro Gln Pro Ala Arg Arg Leu Phe Ile His Asn Pro Ile Arg Val Ile
    210                 215                 220

Pro Asp Val Tyr Gly Val Ala Val Pro Leu Thr Pro Ala Val Asn Pro
225                 230                 235                 240

Ser Thr Asn Arg Ala Val Asp Leu Thr Glu Ser Ile Leu Arg Ser Ala
                245                 250                 255

Tyr His Cys His Leu Thr Tyr Leu Lys Asn Met Gly Val Gly Ala Ser
            260                 265                 270

Leu Thr Ile Ser Leu Ile Lys Asp Gly His Leu Trp Gly Leu Ile Ala

-continued

```
                275                 280                 285
Cys His His Gln Thr Pro Lys Val Ile Pro Phe Glu Leu Arg Lys Ala
    290                 295                 300

Cys Glu Phe Phe Gly Arg Val Val Phe Ser Asn Ile Ser Ala Gln Glu
305                 310                 315                 320

Asp Thr Glu Thr Phe Asp Tyr Arg Val Gln Leu Ala Glu His Glu Ala
                325                 330                 335

Val Leu Leu Asp Lys Met Thr Thr Ala Ala Asp Phe Val Glu Gly Leu
            340                 345                 350

Thr Asn His Pro Asp Arg Leu Leu Gly Leu Thr Gly Ser Gln Gly Ala
        355                 360                 365

Ala Ile Cys Phe Gly Glu Lys Leu Ile Leu Val Gly Glu Thr Pro Asp
    370                 375                 380

Glu Lys Ala Val Gln Tyr Leu Leu Gln Trp Leu Glu Asn Arg Glu Val
385                 390                 395                 400

Gln Asp Val Phe Phe Thr Ser Ser Leu Ser Gln Ile Tyr Pro Asp Ala
                405                 410                 415

Val Asn Phe Lys Ser Val Ala Ser Gly Leu Leu Ala Ile Pro Ile Ala
            420                 425                 430

Arg His Asn Phe Leu Leu Trp Phe Arg Pro Glu Val Leu Gln Thr Val
        435                 440                 445

Asn Trp Gly Gly Asp Pro Asn His Ala Tyr Glu Ala Thr Gln Glu Asp
    450                 455                 460

Gly Lys Ile Glu Leu His Pro Arg Gln Ser Phe Asp Leu Trp Lys Glu
465                 470                 475                 480

Ile Val Arg Leu Gln Ser Leu Pro Trp Gln Ser Val Glu Ile Gln Ser
                485                 490                 495

Ala Leu Ala Leu Lys Lys Ala Ile Val Asn Leu Ile Leu Arg Gln Ala
            500                 505                 510

Glu Glu Gln Ala Tyr Val Glu Gln Lys Leu Ile Ser Glu Asp Leu
        515                 520                 525

Asn Ser Ala Val Asp His His His His His
    530                 535
```

<210> SEQ ID NO 49
<211> LENGTH: 539
<212> TYPE: PRT
<213> ORGANISM: Syncechocystis sp.

<400> SEQUENCE: 49

```
Met Ala Thr Thr Val Gln Leu Ser Asp Gln Ser Leu Arg Gln Leu Glu
1               5                   10                  15

Thr Leu Ala Ile His Thr Ala His Leu Ile Gln Pro His Gly Leu Val
            20                  25                  30

Val Val Leu Gln Glu Pro Asp Leu Thr Ile Ser Gln Ile Ser Ala Asn
        35                  40                  45

Cys Thr Gly Ile Leu Gly Arg Ser Pro Glu Asp Leu Leu Gly Arg Thr
    50                  55                  60

Leu Gly Glu Val Phe Asp Ser Phe Gln Ile Asp Pro Ile Gln Ser Arg
65                  70                  75                  80

Leu Thr Ala Gly Gln Ile Ser Ser Leu Asn Pro Ser Lys Leu Trp Ala
                85                  90                  95

Arg Val Met Gly Asp Asp Phe Val Ile Phe Asp Gly Val Phe His Arg
            100                 105                 110
```

-continued

```
Asn Ser Asp Gly Leu Leu Val Cys Glu Leu Glu Pro Ala Tyr Thr Ser
        115                 120                 125
Asp Asn Leu Pro Phe Leu Gly Phe Tyr His Met Ala Asn Ala Ala Leu
130                 135                 140
Asn Arg Leu Arg Gln Gln Ala Asn Leu Arg Asp Phe Tyr Asp Val Ile
145                 150                 155                 160
Val Glu Glu Val Arg Arg Met Thr Gly Phe Asp Arg Val Met Leu Trp
                165                 170                 175
Arg Phe Asp Glu Asn Asn His Gly Asp Val Ile Ala Glu Asp Lys Arg
                180                 185                 190
Asp Asp Met Glu Pro Tyr Leu Gly Leu His Tyr Pro Glu Ser Asp Ile
            195                 200                 205
Pro Gln Pro Ala Arg Arg Leu Phe Ile His Asn Pro Ile Arg Val Ile
    210                 215                 220
Pro Asp Val Tyr Gly Val Ala Val Pro Leu Thr Pro Ala Val Asn Pro
225                 230                 235                 240
Ser Thr Asn Arg Ala Val Asp Leu Thr Glu Ser Ile Leu Arg Ser Ala
                245                 250                 255
Tyr His Cys His Leu Thr Tyr Leu Lys Asn Met Gly Val Gly Ala Ser
                260                 265                 270
Leu Thr Ile Ser Leu Ile Lys Asp Gly His Leu Trp Gly Leu Ile Ala
            275                 280                 285
Cys His His Gln Thr Pro Lys Val Ile Pro Phe Glu Leu Arg Lys Ala
    290                 295                 300
Cys Glu Phe Phe Gly Arg Val Val Phe Ser Asn Ile Ser Ala Gln Glu
305                 310                 315                 320
Asp Thr Glu Thr Phe Asp Tyr Arg Val Gln Leu Ala Glu His Glu Ala
                325                 330                 335
Val Leu Leu Asp Lys Met Thr Thr Ala Ala Asp Phe Val Glu Gly Leu
            340                 345                 350
Thr Asn His Pro Asp Arg Leu Leu Gly Leu Thr Gly Ser Gln Gly Ala
    355                 360                 365
Ala Ile Cys Phe Gly Glu Lys Leu Ile Leu Val Gly Glu Thr Pro Asp
370                 375                 380
Glu Lys Ala Val Gln Tyr Leu Leu Gln Trp Leu Glu Asn Arg Glu Val
385                 390                 395                 400
Gln Asp Val Phe Phe Thr Ser Ser Leu Ser Gln Ile Tyr Pro Asp Ala
                405                 410                 415
Val Asn Phe Lys Ser Val Ala Ser Gly Leu Leu Ala Ile Pro Ile Ala
            420                 425                 430
Arg His Asn Phe Leu Leu Trp Phe Arg Pro Glu Val Leu Gln Thr Val
    435                 440                 445
Asn Trp Gly Gly Asp Pro Asn His Ala Tyr Glu Ala Thr Gln Glu Asp
450                 455                 460
Gly Lys Ile Glu Leu His Pro Arg Gln Ser Phe Asp Leu Trp Lys Glu
465                 470                 475                 480
Ile Val Arg Leu Gln Ser Leu Pro Trp Gln Ser Val Glu Ile Gln Ser
                485                 490                 495
Ala Leu Ala Leu Lys Lys Ala Ile Val Asn Leu Ile Leu Arg Gln Ala
            500                 505                 510
Glu Glu Gln Ala Tyr Val Glu Gln Lys Leu Ile Ser Glu Glu Asp Leu
    515                 520                 525
Asn Ser Ala Val Asp His His His His His His
```

<210> SEQ ID NO 50
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 50
cggatatcat gtcccctata cta                                           23

<210> SEQ ID NO 51
<211> LENGTH: 28
<212> TYPE: DNA
<213> ORGANISM: Artificial
<220> FEATURE:
<223> OTHER INFORMATION: Synthetic oligonucleotide PCR primer

<400> SEQUENCE: 51
gcgcggccgc ttagccgata aattgtcc                                      28

<210> SEQ ID NO 52
<211> LENGTH: 15
<212> TYPE: PRT
<213> ORGANISM: Artificial
<220> FEATURE:
<223> OTHER INFORMATION: Synthetic peptide linker.

<400> SEQUENCE: 52

Gly Gly Gly Gly Ser Gly Gly Gly Gly Ser Gly Gly Gly Gly Ser
1               5                   10                  15

<210> SEQ ID NO 53
<211> LENGTH: 184
<212> TYPE: PRT
<213> ORGANISM: Syncechocystis sp.

<400> SEQUENCE: 53

Leu Gly Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

```
Leu Ile Leu Arg Gln Ala Glu Glu
            180

<210> SEQ ID NO 54
<211> LENGTH: 184
<212> TYPE: PRT
<213> ORGANISM: Syncechocystis sp.

<400> SEQUENCE: 54

Leu Ala Glu His Gly Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Val Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Gly Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Ser Arg Gln Ala Glu Glu
            180

<210> SEQ ID NO 55
<211> LENGTH: 184
<212> TYPE: PRT
<213> ORGANISM: Syncechocystis sp.

<400> SEQUENCE: 55

Leu Ala Glu His Glu Ala Ala Leu Leu Asp Lys Met Pro Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Phe Leu
        35                  40                  45

Val Gly Glu Thr Pro Asp Glu Lys Ala Val Gln Tyr Leu Leu Gln Trp
    50                  55                  60

Leu Glu Asn Arg Asp Val Gln Asp Val Phe Leu Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg Leu Asn Phe Leu Leu Gly Phe Arg Pro
            100                 105                 110

Gly Val Leu Gln Thr Val Ser Arg Gly Gly Asp Pro Asn His Ala Tyr
        115                 120                 125
```

```
Val Ala Thr Gln Glu Asp Gly Lys Ile Glu Leu His Pro Arg Gln Ser
            130                 135                 140

Phe Asp Leu Trp Lys Glu Ile Val Arg Leu Gln Ser Leu Pro Trp Gln
145                 150                 155                 160

Ser Val Gly Ile Arg Ser Ala Leu Ala Leu Lys Lys Ala Ile Val Asn
                165                 170                 175

Leu Ile Leu Arg Gln Ala Glu Glu
            180

<210> SEQ ID NO 56
<211> LENGTH: 184
<212> TYPE: PRT
<213> ORGANISM: Syncechocystis sp.

<400> SEQUENCE: 56

Leu Ala Glu His Glu Ala Val Leu Leu Val Lys Met Thr Thr Ala Ala
1               5                   10                  15

Asp Phe Val Glu Gly Leu Thr Asn His Pro Asp Arg Leu Leu Gly Leu
                20                  25                  30

Thr Gly Ser Gln Gly Ala Ala Ile Cys Phe Gly Glu Lys Leu Ile Leu
            35                  40                  45

Val Gly Glu Thr Pro Asp Glu Lys Ala Val Gln Tyr Leu Leu Gln Trp
        50                  55                  60

Leu Glu Asn Arg Glu Val Gln Asp Gly Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Val Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 57
<211> LENGTH: 184
<212> TYPE: PRT
<213> ORGANISM: Syncechocystis sp.

<400> SEQUENCE: 57

Leu Ala Glu His Glu Ala Val Leu Leu Asp Arg Met Thr Thr Ala Ala
1               5                   10                  15

Asp Phe Val Glu Gly Leu Thr Asn His Pro Asp Arg Leu Leu Gly Leu
                20                  25                  30

Thr Gly Ser Gln Gly Ala Ala Ile Cys Phe Gly Glu Lys Leu Ile Leu
            35                  40                  45

Val Gly Glu Thr Pro Asp Glu Lys Ala Val Gln Tyr Leu Leu Gln Trp
        50                  55                  60

Leu Glu Asn Arg Glu Val Gln Asp Val Phe Phe Thr Ser Ser Leu Ser
65                  70                  75                  80
```

Gln Ile Tyr Pro Asp Ala Val Asn Phe Lys Ser Val Ala Ser Gly Leu
                85                  90                  95

Leu Ala Ile Pro Ile Ala Arg His Asn Ile Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Val Glu Pro His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Asp Leu Lys Lys Ala Ile Val Asn
                165                 170                 175

Leu Ile Leu Arg Gln Ala Glu Glu
            180

<210> SEQ ID NO 58
<211> LENGTH: 184
<212> TYPE: PRT
<213> ORGANISM: Syncechocystis sp.

<400> SEQUENCE: 58

Leu Ala Glu His Glu Ala Val Leu Leu Asp Lys Met Thr Thr Ala Ala
1               5                   10                  15

Asp Phe Val Glu Gly Leu Thr Lys His Pro Asp Arg Leu Leu Gly Leu
            20                  25                  30

Thr Gly Ser Gln Gly Ala Ala Ile Cys Phe Gly Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Ile Leu Lys Ser Val Ala Ser Gly Leu
                85                  90                  95

Leu Ala Ile Pro Ile Ala Arg Arg Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 59
<211> LENGTH: 184
<212> TYPE: PRT
<213> ORGANISM: Syncechocystis sp.

<400> SEQUENCE: 59

Leu Ala Glu His Glu Ala Val Leu Leu Asp Lys Met Thr Thr Ala Ala
1               5                   10                  15

Asp Phe Val Glu Gly Leu Thr Asn His Pro Val Arg Leu Leu Gly Leu
            20                  25                  30

```
Thr Gly Ser Gln Gly Ala Ala Ile Cys Phe Gly Lys Leu Ile Leu
        35                  40                  45

Val Gly Glu Thr Pro Asp Glu Lys Ala Val Gln Tyr Leu Leu Gln Trp
 50                  55                  60

Leu Glu Asn Arg Glu Val Gln Asp Val Phe Thr Ser Ser Leu Ser
 65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 60
<211> LENGTH: 184
<212> TYPE: PRT
<213> ORGANISM: Syncechocystis sp.

<400> SEQUENCE: 60

Leu Ala Glu His Glu Ala Val Leu Leu Asp Lys Met Thr Thr Ala Ala
 1               5                  10                  15

Asp Phe Val Glu Gly Leu Thr Asn His Pro Asp Arg Leu Leu Gly Leu
                20                  25                  30

Thr Gly Ser Gln Gly Ala Ala Thr Cys Phe Gly Lys Leu Ile Leu
        35                  40                  45

Val Gly Glu Thr Pro Asp Glu Lys Ala Val Gln Tyr Leu Leu Gln Trp
 50                  55                  60

Leu Glu Asn Arg Glu Val Gln Asp Val Phe Thr Thr Ser Leu Ser
 65                  70                  75                  80

Arg Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 61
<211> LENGTH: 184
<212> TYPE: PRT
```

-continued

<213> ORGANISM: Syncechocystis sp.

<400> SEQUENCE: 61

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Arg Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 62
<211> LENGTH: 184
<212> TYPE: PRT
<213> ORGANISM: Syncechocystis sp.

<400> SEQUENCE: 62

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Val Gly Gly Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn

Leu Ile Leu Arg Gln Ala Glu Glu
          180

<210> SEQ ID NO 63
<211> LENGTH: 184
<212> TYPE: PRT
<213> ORGANISM: Syncechocystis sp.

<400> SEQUENCE: 63

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Val Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
          180

<210> SEQ ID NO 64
<211> LENGTH: 184
<212> TYPE: PRT
<213> ORGANISM: Syncechocystis sp.

<400> SEQUENCE: 64

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Leu Gln Tyr Leu Leu Gln Trp
    50                  55                  60

Leu Glu Asn Arg Glu Val Gln Asp Val Phe Phe Thr Ser Ser Leu Pro
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr

```
               115                 120                 125
Glu Ala Thr Gln Glu Asp Gly Lys Ile Glu Leu His Pro Arg Gln Ser
        130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 65
<211> LENGTH: 184
<212> TYPE: PRT
<213> ORGANISM: Syncechocystis sp.

<400> SEQUENCE: 65

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
50                  55                  60

Met Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 66
<211> LENGTH: 184
<212> TYPE: PRT
<213> ORGANISM: Syncechocystis sp.

<400> SEQUENCE: 66

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
50                  55                  60

Leu Glu Ser Arg Glu Val Gln Asp Val Phe Phe Thr Ser Ser Leu Ser
```

```
                65                  70                  75                  80
Gln Ile Tyr Pro Asp Ala Val Asn Phe Lys Ser Val Ala Ser Gly Leu
                85                  90                  95

Leu Ala Ile Pro Val Ala Arg His Asn Phe Leu Leu Trp Cys Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 67
<211> LENGTH: 184
<212> TYPE: PRT
<213> ORGANISM: Synechocystis sp.

<400> SEQUENCE: 67

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Thr Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 68
<211> LENGTH: 184
<212> TYPE: PRT
<213> ORGANISM: Synechocystis sp.

<400> SEQUENCE: 68

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
```

-continued

```
                    20                  25                  30

Thr Gly Ser Gln Gly Ala Ala Ile Cys Phe Gly Glu Lys Leu Ile Leu
            35                  40                  45

Val Gly Glu Thr Pro Asp Glu Lys Ala Val Gln Tyr Leu Leu Gln Trp
    50                  55                  60

Leu Glu Asn Arg Val Val Gln Asp Val Phe Phe Thr Ser Ser Leu Pro
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
    115                 120                 125

Glu Ala Thr Gln Glu Asp Gly Lys Ile Glu Leu His Pro Arg Gln Ser
        130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180
```

<210> SEQ ID NO 69
<211> LENGTH: 184
<212> TYPE: PRT
<213> ORGANISM: Syncechocystis sp.

<400> SEQUENCE: 69

```
Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val His Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
    115                 120                 125

Glu Ala Thr Gln Glu Asp Gly Lys Ile Glu Leu His Pro Arg Gln Ser
        130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180
```

<210> SEQ ID NO 70
<211> LENGTH: 184

<212> TYPE: PRT
<213> ORGANISM: Syncechocystis sp.

<400> SEQUENCE: 70

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Tyr Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Ser Pro Trp Gln
145                 150                 155                 160

Ser Val Glu Ile Gln Ser Ala Leu Ala Leu Lys Lys Ala Ile Val Asp
                165                 170                 175

Leu Ile Leu Arg Gln Ala Glu Glu
            180

<210> SEQ ID NO 71
<211> LENGTH: 184
<212> TYPE: PRT
<213> ORGANISM: Syncechocystis sp.

<400> SEQUENCE: 71

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Asn Val Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

```
Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 72
<211> LENGTH: 184
<212> TYPE: PRT
<213> ORGANISM: Syncechocystis sp.

<400> SEQUENCE: 72

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
                20                  25                  30

Thr Gly Ser Gln Gly Ala Ala Ile Cys Phe Gly Glu Lys Leu Ile Leu
            35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asp Phe Leu Leu Trp Phe Arg Pro
                100                 105                 110

Glu Val Leu Gln Thr Val Asn Trp Gly Gly Asp Pro Asn His Ala Tyr
            115                 120                 125

Glu Ala Thr Gln Glu Asp Gly Lys Ile Glu Leu His Pro Arg Gln Ser
130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 73
<211> LENGTH: 184
<212> TYPE: PRT
<213> ORGANISM: Syncechocystis sp.

<400> SEQUENCE: 73

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
                20                  25                  30

Thr Gly Ser Gln Gly Ala Ala Ile Cys Phe Gly Glu Lys Leu Ile Leu
            35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
                100                 105                 110
```

```
Glu Val Leu Gln Thr Val Asn Trp Gly Gly Asp Pro Asn His Ala Phe
            115                 120                 125
Glu Ala Thr Gln Glu Asp Gly Lys Ile Glu Leu His Pro Arg Gln Ser
        130                 135                 140
Phe Asp Leu Trp Lys Glu Ile Val Arg Leu Gln Ser Leu Pro Trp Gln
145                 150                 155                 160
Ser Val Glu Ile Gln Ser Ala Leu Ala Leu Lys Lys Ala Ile Val Asn
                165                 170                 175
Leu Ile Leu Arg Gln Ala Glu Glu
            180
```

<210> SEQ ID NO 74
<211> LENGTH: 184
<212> TYPE: PRT
<213> ORGANISM: Syncechocystis sp.

<400> SEQUENCE: 74

```
Leu Ala Glu His Glu Ala Val Leu Leu Asp Lys Met Thr Thr Ala Ala
1               5                   10                  15
Asp Phe Val Glu Gly Leu Thr Asn His Pro Asp Arg Leu Leu Gly Leu
            20                  25                  30
Thr Gly Ser Gln Gly Ala Ala Ile Cys Phe Gly Glu Lys Leu Ile Leu
        35                  40                  45
Val Gly Glu Thr Pro Asp Glu Lys Ala Val Gln Tyr Leu Leu Gln Trp
    50                  55                  60
Leu Glu Asn Arg Glu Val Gln Asp Val Phe Phe Thr Ser Ser Leu Ser
65                  70                  75                  80
Gln Ile Tyr Pro Asp Ala Val Asn Phe Lys Ser Val Ala Ser Gly Leu
                85                  90                  95
Leu Ala Ile Pro Ile Ala Arg His Asn Phe Leu Leu Trp Phe Arg Pro
            100                 105                 110
Glu Val Leu Gln Thr Val Asn Trp Gly Gly Asp Pro Asn His Ala Tyr
            115                 120                 125
Glu Ala Cys Gln Glu Asp Gly Lys Ile Glu Leu His Pro Arg Gln Ser
        130                 135                 140
Phe Asp Leu Trp Lys Glu Ile Val Arg Leu Gln Ser Leu Pro Trp Gln
145                 150                 155                 160
Ser Val Glu Ile Gln Ser Ala Leu Ala Leu Lys Lys Ala Ile Val Asn
                165                 170                 175
Leu Ile Leu Arg Gln Ala Glu Glu
            180
```

<210> SEQ ID NO 75
<211> LENGTH: 184
<212> TYPE: PRT
<213> ORGANISM: Syncechocystis sp.

<400> SEQUENCE: 75

```
Leu Ala Glu His Glu Ala Val Leu Leu Asp Lys Met Thr Thr Ala Ala
1               5                   10                  15
Asp Phe Val Glu Gly Leu Thr Asn His Pro Asp Arg Leu Leu Gly Leu
            20                  25                  30
Thr Gly Ser Gln Gly Ala Ala Ile Cys Phe Gly Glu Lys Leu Ile Leu
        35                  40                  45
Val Gly Glu Thr Pro Asp Glu Lys Ala Val Gln Tyr Leu Leu Gln Trp
    50                  55                  60
```

```
Leu Glu Asn Arg Glu Val Gln Asp Val Phe Phe Thr Ser Ser Leu Ser
 65                  70                  75                  80

Gln Ile Tyr Pro Asp Ala Val Asn Phe Lys Ser Val Ala Ser Gly Leu
                 85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Glu Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Pro Ile Leu Arg Gln Ala Glu Glu
            180
```

<210> SEQ ID NO 76
<211> LENGTH: 184
<212> TYPE: PRT
<213> ORGANISM: Syncechocystis sp.

<400> SEQUENCE: 76

```
Leu Ala Glu His Glu Ala Val Leu Leu Asp Lys Met Thr Thr Ala Ala
  1               5                  10                  15

Asp Phe Val Glu Gly Leu Thr Asn His Pro Asp Arg Leu Leu Gly Leu
                 20                  25                  30

Thr Gly Ser Gln Gly Ala Ala Ile Cys Phe Gly Glu Lys Leu Ile Leu
             35                  40                  45

Val Gly Glu Thr Pro Asp Glu Lys Ala Val Gln Tyr Leu Leu Gln Trp
 50                  55                  60

Leu Glu Asn Arg Glu Val Gln Asp Val Phe Phe Thr Ser Ser Leu Ser
 65                  70                  75                  80

Gln Ile Tyr Pro Asp Ala Val Asn Phe Lys Ser Val Ala Ser Gly Leu
                 85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Thr Leu Arg Gln Ala Glu Glu
            180
```

<210> SEQ ID NO 77
<211> LENGTH: 184
<212> TYPE: PRT
<213> ORGANISM: Syncechocystis sp.

<400> SEQUENCE: 77

```
Leu Ala Glu His Glu Ala Val Leu Leu Asp Lys Met Thr Thr Ala Ala
  1               5                  10                  15
```

```
Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
 50                  55                  60

Leu Glu Asn Arg Glu Val Gln Asp Val Phe Phe Thr Ser Ser Leu Ser
 65                  70                  75                  80

Gln Ile Tyr Pro Asp Ala Val Asn Phe Lys Ser Val Ala Ser Gly Leu
            85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
            115                 120                 125

Glu Ala Thr Gln Glu Asp Gly Lys Ile Glu Leu Arg Pro Arg Gln Ser
 130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
            165                 170                 175

Leu Ile Phe Ala Pro Gly Arg Arg
            180
```

<210> SEQ ID NO 78
<211> LENGTH: 184
<212> TYPE: PRT
<213> ORGANISM: Artificial
<220> FEATURE:
<223> OTHER INFORMATION: Consensus sequence.

<400> SEQUENCE: 78

```
Leu Ala Glu His Glu Ala Val Leu Leu Asp Lys Met Thr Thr Ala Ala
 1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
 50                  55                  60

Leu Glu Asn Arg Glu Val Gln Asp Val Phe Phe Thr Ser Ser Leu Ser
 65                  70                  75                  80

Gln Ile Tyr Pro Asp Ala Val Asn Phe Lys Ser Val Ala Ser Gly Leu
            85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
            115                 120                 125

Glu Ala Thr Gln Glu Asp Gly Lys Ile Glu Leu His Pro Arg Gln Ser
 130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
            165                 170                 175

Leu Ile Leu Arg Gln Ala Glu Glu
            180
```

<210> SEQ ID NO 79
<211> LENGTH: 112
<212> TYPE: PRT
<213> ORGANISM: Artificial
<220> FEATURE:
<223> OTHER INFORMATION: Consensus sequence

<400> SEQUENCE: 79

Ala Glu Val Asp Lys Thr Asn Asp Ile Cys Phe Glu Ile Glu Val Leu
1               5                   10                  15

Asn Glu Gln Val Phe Ser Ser Gln Asn Phe Ile His Asn Phe Trp Phe
            20                  25                  30

Glu Asn Trp Tyr Glu Thr Ile Glu Leu His Lys Leu Glu Gln Ala Asp
        35                  40                  45

Leu Ile Leu Arg Gln Ala Glu Ala Glu Val Asp Lys Thr Asn Asp
50                  55                  60

Ile Cys Phe Glu Ile Glu Val Leu Asn Glu Gln Val Phe Ser Ser Gln
65                  70                  75                  80

Asn Phe Ile His Asn Phe Trp Phe Glu Asn Trp Tyr Glu Thr Ile Glu
                85                  90                  95

Leu His Lys Leu Glu Gln Ala Asp Leu Ile Leu Arg Gln Ala Glu Glu
            100                 105                 110

<210> SEQ ID NO 80
<211> LENGTH: 184
<212> TYPE: PRT
<213> ORGANISM: Syncechocystis sp.

<400> SEQUENCE: 80

Leu Ala Glu His Glu Ala Val Leu Leu Asp Glu Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asp His Ala Tyr
        115                 120                 125

Glu Ala Thr Gln Glu Asp Gly Arg Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 81
<211> LENGTH: 184
<212> TYPE: PRT

<210> SEQ ID NO 81
<211> LENGTH: 183
<212> TYPE: PRT
<213> ORGANISM: Syncechocystis sp.

<400> SEQUENCE: 81

Leu Ala Glu His Glu Ala Val Leu Leu Asp Lys Val Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Arg Asp Val Phe Phe Thr Ser Thr Leu Ser
65                  70                  75                  80

Leu Ile Tyr Pro Asp Ala Val Asn Phe Lys Ser Val Ala Ser Gly Leu
                85                  90                  95

Leu Ala Thr Pro Ile Ala Arg His Asn Phe Leu Leu Trp Phe Arg Pro
            100                 105                 110

Val Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Trp Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 82
<211> LENGTH: 184
<212> TYPE: PRT
<213> ORGANISM: Syncechocystis sp.

<400> SEQUENCE: 82

Leu Ala Glu His Glu Ala Val Leu Leu Asp Lys Met Ser Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Gly Lys Ala Val Gln Tyr Leu Leu Gln Trp
    50                  55                  60

Met Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asp Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn

Leu Ile Leu Arg Gln Ala Glu Glu
            180

<210> SEQ ID NO 83
<211> LENGTH: 184
<212> TYPE: PRT
<213> ORGANISM: Syncechocystis sp.

<400> SEQUENCE: 83

Leu Ala Glu His Glu Ala Val Leu Leu Asp Lys Met Thr Ser Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala His
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Phe Arg Gln Ala Glu Glu
            180

<210> SEQ ID NO 84
<211> LENGTH: 184
<212> TYPE: PRT
<213> ORGANISM: Syncechocystis sp.

<400> SEQUENCE: 84

Leu Ala Glu His Glu Ala Val Leu Leu Asp Lys Met Thr Thr Ala Ala
1               5                   10                  15

Asp Leu Val Glu Gly Leu Thr Asn His Pro Asp Arg Leu Leu Gly Leu
            20                  25                  30

Thr Gly Ser Gln Gly Ala Ala Ile Arg Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr

-continued

```
            115                 120                 125
Glu Ala Thr Gln Glu Asp Gly Lys Ile Glu Leu His Pro Arg Gln Ser
        130                 135                 140

Phe Asp Leu Trp Lys Glu Ile Val Arg Leu Gln Ser Leu Pro Trp Gln
145                 150                 155                 160

Ser Val Val Ile Gln Ser Ala Leu Ala Leu Lys Lys Ala Ile Val Asn
                165                 170                 175

Leu Ile Leu Arg Gln Ala Glu Glu
            180

<210> SEQ ID NO 85
<211> LENGTH: 184
<212> TYPE: PRT
<213> ORGANISM: Syncechocystis sp.

<400> SEQUENCE: 85

Leu Ala Glu His Glu Ala Val Leu Leu Asp Lys Met Thr Thr Ala Ala
1               5                   10                  15

Asp Phe Asp Glu Gly Leu Thr Asn His Pro Asp Arg Leu Leu Gly Leu
                20                  25                  30

Thr Gly Ser Gln Gly Ala Ala Ile Cys Phe Gly Glu Lys Leu Ile Leu
            35                  40                  45

Val Gly Gly Thr Pro Asp Glu Lys Ala Val Gln Arg Leu Leu Gln Trp
        50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Pro Leu Pro Trp Gln
145                 150                 155                 160

Ser Val Glu Ile Gln Ser Ala Pro Ala Leu Lys Lys Ala Ile Val Asn
                165                 170                 175

Leu Ile Leu Arg Gln Ala Glu Glu
            180

<210> SEQ ID NO 86
<211> LENGTH: 184
<212> TYPE: PRT
<213> ORGANISM: Syncechocystis sp.

<400> SEQUENCE: 86

Leu Ala Glu His Glu Ala Val Leu Leu Asp Lys Met Thr Thr Ala Ala
1               5                   10                  15

Asp Phe Val Gly Gly Leu Thr Asn His Pro Asp Arg Leu Leu Gly Leu
                20                  25                  30

Thr Gly Ser Gln Gly Ala Ala Ile Cys Phe Gly Glu Lys Leu Ile Leu
            35                  40                  45

Val Gly Glu Thr Pro Asp Glu Lys Ala Val Gln Tyr Leu Leu Gln Trp
        50                  55                  60

Leu Glu Asn Arg Glu Val Gln Asp Val Phe Phe Thr Ser Ser Leu Ser
```

```
                65                  70                  75                  80
Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 87
<211> LENGTH: 184
<212> TYPE: PRT
<213> ORGANISM: Syncechocystis sp.

<400> SEQUENCE: 87

Leu Ala Glu His Glu Ala Val Leu Leu Asp Lys Met Thr Thr Ala Ala
1               5                   10                  15

Asp Phe Val Glu Gly Leu Thr Asn Tyr Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Leu Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Val Asp Leu Trp Lys Glu Ile Val Arg Leu Gln Ser Leu Pro Trp Gln
145                 150                 155                 160

Ser Val Glu Ile Gln Ser Ala Gln Ala Leu Lys Lys Ala Ile Val Asn
                165                 170                 175

Leu Val Leu Arg Gln Ala Glu Glu
            180

<210> SEQ ID NO 88
<211> LENGTH: 184
<212> TYPE: PRT
<213> ORGANISM: Syncechocystis sp.

<400> SEQUENCE: 88

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
```

-continued

```
                    20                  25                  30

Thr Gly Ser Gln Gly Ala Ala Ile Cys Phe Gly Glu Lys Leu Ile Leu
            35                  40                  45

Val Gly Glu Thr Pro Asp Glu Lys Ala Val Gln Tyr Leu Leu Gln Trp
        50                  55                  60

Leu Glu Asn Arg Glu Val Gln Asp Val Phe Phe Thr Ser Pro Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Phe Arg Gln Ala Glu Glu
            180

<210> SEQ ID NO 89
<211> LENGTH: 184
<212> TYPE: PRT
<213> ORGANISM: Syncechocystis sp.

<400> SEQUENCE: 89

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Tyr Phe Arg Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Arg Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Pro Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 90
<211> LENGTH: 184
```

```
<212> TYPE: PRT
<213> ORGANISM: Syncechocystis sp.

<400> SEQUENCE: 90

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Gly Leu His Pro Arg Gln Ser
    130                 135                 140

Phe Asp Leu Trp Lys Glu Ile Val Arg Leu Gln Ser Leu Pro Arg Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 91
<211> LENGTH: 184
<212> TYPE: PRT
<213> ORGANISM: Syncechocystis sp.

<400> SEQUENCE: 91

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Arg Ser
    130                 135                 140

Phe Asp Leu Trp Lys Glu Ile Val Arg Leu Gln Ser Leu Pro Trp Gln
145                 150                 155                 160
```

Ser Val Glu Ile Gln Ser Ala Leu Ala Leu Lys Lys Ala Ile Val Asn
            165                 170                 175

Leu Ile Leu Arg Gln Ala Glu Glu
            180

<210> SEQ ID NO 92
<211> LENGTH: 184
<212> TYPE: PRT
<213> ORGANISM: Syncechocystis sp.

<400> SEQUENCE: 92

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Leu Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 93
<211> LENGTH: 82
<212> TYPE: PRT
<213> ORGANISM: Syncechocystis sp.

<400> SEQUENCE: 93

Leu Ala Glu His Glu Ala Val Leu Leu Asp Lys Met Thr Thr Ala Ala
1               5                   10                  15

Asp Phe Val Glu Gly Leu Thr Lys His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile

<210> SEQ ID NO 94
<211> LENGTH: 86
<212> TYPE: PRT

<213> ORGANISM: Syncechocystis sp.

<400> SEQUENCE: 94

```
Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
                20                  25                  30

Thr Gly Ser Gln Gly Ala Ala Ile Cys Phe Gly Glu Lys Leu Ile Leu
            35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala
                85
```

<210> SEQ ID NO 95
<211> LENGTH: 95
<212> TYPE: PRT
<213> ORGANISM: Syncechocystis sp.

<400> SEQUENCE: 95

```
Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
                20                  25                  30

Thr Gly Ser Gln Gly Ala Ala Ile Cys Phe Gly Glu Lys Leu Ile Leu
            35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly
                85                  90                  95
```

<210> SEQ ID NO 96
<211> LENGTH: 106
<212> TYPE: PRT
<213> ORGANISM: Syncechocystis sp.

<400> SEQUENCE: 96

```
Leu Ala Glu His Glu Ala Val Leu Leu Asp Lys Met Thr Thr Ala Ala
1               5                   10                  15

Asp Phe Val Glu Gly Leu Thr Asn His Pro Asp Arg Pro Leu Gly Leu
                20                  25                  30

Thr Gly Ser Gln Gly Ala Ala Ile Cys Phe Gly Glu Lys Leu Ile Leu
            35                  40                  45

Val Gly Glu Thr Pro Asp Glu Lys Ala Val Gln Tyr Leu Leu Gln Trp
    50                  55                  60

Leu Glu Ser Arg Glu Val Gln Asp Val Phe Phe Thr Ser Ser Leu Ser
65                  70                  75                  80

Gln Phe Tyr Pro Asp Ala Val Asn Phe Glu Ser Val Ala Ser Gly Leu
                85                  90                  95

Leu Ala Ile Pro Ile Ala Arg His Asn Phe
                100                 105
```

<210> SEQ ID NO 97

<211> LENGTH: 184
<212> TYPE: PRT
<213> ORGANISM: Syncechocystis sp.

<400> SEQUENCE: 97

Leu Ala Glu Arg Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Leu Thr Ser Ser Leu Ser
65                  70                  75                  80

Gln Ile Tyr Pro Asp Ala Val Asn Phe Lys Ser Val Ala Gly Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Ser Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 98
<211> LENGTH: 184
<212> TYPE: PRT
<213> ORGANISM: Syncechocystis sp.

<400> SEQUENCE: 98

Leu Ala Glu His Glu Ala Val Leu Leu Asp Glu Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asp His Ala Tyr
        115                 120                 125

Glu Ala Thr Gln Glu Asp Gly Arg Ile Glu Leu His Pro Arg Gln Ser
    130                 135                 140

Phe Asp Leu Arg Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
              165                 170                 175

Leu Ile Leu Arg Gln Ala Glu Glu
            180

<210> SEQ ID NO 99
<211> LENGTH: 184
<212> TYPE: PRT
<213> ORGANISM: Syncechocystis sp.

<400> SEQUENCE: 99

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Arg Leu Ile Leu
        35                  40                  45

Val Gly Glu Thr Pro Asp Glu Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Gly Gly Lys Ile Glu Leu His Pro Arg Gln Ser
    130                 135                 140

Leu Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 100
<211> LENGTH: 184
<212> TYPE: PRT
<213> ORGANISM: Syncechocystis sp.

<400> SEQUENCE: 100

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

```
Glu Val Leu Gln Ala Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Leu Lys Glu Ile Val Arg Leu Gln Ser Leu Pro Trp Gln
145                 150                 155                 160

Ser Val Glu Ile Gln Ser Ala Leu Ala Leu Lys Lys Ala Ile Ala Asn
                165                 170                 175

Leu Ile Leu Arg Gln Ala Glu Glu
            180

<210> SEQ ID NO 101
<211> LENGTH: 184
<212> TYPE: PRT
<213> ORGANISM: Syncechocystis sp.

<400> SEQUENCE: 101

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Leu Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 102
<211> LENGTH: 184
<212> TYPE: PRT
<213> ORGANISM: Syncechocystis sp.

<400> SEQUENCE: 102

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60
```

```
Leu Glu Asn Arg Glu Val Gln Asp Val Phe Phe Thr Ser Ser Leu Ser
 65                  70                  75                  80

Gln Ile Tyr Pro Asp Ala Val Asn Phe Lys Ser Val Ala Ser Gly Leu
                 85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Leu Lys Glu Ile Val Arg Leu Gln Ser Leu Pro Trp Gln
145                 150                 155                 160

Ser Val Glu Ile Gln Ser Ala Leu Ala Leu Lys Lys Ala Ile Ala Asn
                165                 170                 175

Leu Ile Leu Arg Gln Ala Glu Glu
            180
```

<210> SEQ ID NO 103
<211> LENGTH: 184
<212> TYPE: PRT
<213> ORGANISM: Syncechocystis sp.

<400> SEQUENCE: 103

```
Leu Ala Glu His Glu Ala Val Leu Leu Asp Lys Met Thr Thr Ala Ala
 1               5                  10                  15

Asp Phe Val Glu Gly Leu Thr Asn His Pro Asp Arg Leu Leu Gly Leu
                20                  25                  30

Thr Gly Ser Gln Gly Ala Ala Ile Cys Phe Gly Glu Lys Leu Ile Leu
            35                  40                  45

Val Gly Glu Thr Pro Asp Glu Lys Ala Val Gln Tyr Leu Leu Gln Trp
        50                  55                  60

Leu Glu Asn Arg Glu Val Gln Asp Val Phe Phe Thr Ser Ser Leu Ser
 65                  70                  75                  80

Gln Ile Tyr Pro Asp Ala Val Asn Phe Lys Ser Val Ala Ser Gly Leu
                 85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Arg Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180
```

<210> SEQ ID NO 104
<211> LENGTH: 31
<212> TYPE: PRT
<213> ORGANISM: Syncechocystis sp.

<400> SEQUENCE: 104

```
Leu Ala Glu His Glu Ala Val Leu Leu Asp Lys Met Thr Thr Ala Ala
 1               5                  10                  15
```

```
Gly Phe Val Glu Asp Gln Leu Ile Ile Pro Ile Ala Cys Trp Asp
            20                  25                  30

<210> SEQ ID NO 105
<211> LENGTH: 184
<212> TYPE: PRT
<213> ORGANISM: Syncechocystis sp.

<400> SEQUENCE: 105

Leu Ala Glu His Glu Ala Val Leu Leu Asp Lys Val Thr Thr Ala Ala
1               5                   10                  15

Asp Phe Val Glu Gly Leu Thr Asn His Pro Asp Arg Leu Leu Gly Leu
                20                  25                  30

Thr Gly Ser Gln Gly Ala Ala Ile Cys Phe Gly Glu Lys Leu Ile Leu
            35                  40                  45

Val Gly Glu Thr Pro Asp Glu Lys Ala Val Gln Tyr Leu Leu Gln Trp
        50                  55                  60

Leu Glu Asn Arg Glu Val Arg Asp Val Phe Phe Thr Ser Thr Leu Ser
65                  70                  75                  80

Leu Ile Tyr Pro Asp Ala Val Asn Phe Lys Ser Val Ala Ser Gly Leu
                85                  90                  95

Leu Ala Thr Pro Ile Ala Arg His Asn Phe Leu Leu Trp Phe Arg Pro
            100                 105                 110

Val Val Leu Gln Thr Val Asn Trp Gly Gly Asp Pro Asn His Ala Tyr
        115                 120                 125

Glu Ala Thr Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 106
<211> LENGTH: 184
<212> TYPE: PRT
<213> ORGANISM: Syncechocystis sp.

<400> SEQUENCE: 106

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
                20                  25                  30

Thr Gly Ser Gln Gly Ala Ala Ile Cys Phe Gly Glu Lys Leu Ile Leu
            35                  40                  45

Val Gly Glu Thr Pro Asp Val Lys Ala Val Gln Tyr Leu Leu Gln Trp
        50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125
```

```
Glu Ala Pro Gln Glu Asp Gly Lys Ile Glu Leu His Pro Arg Gln Ser
        130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 107
<211> LENGTH: 184
<212> TYPE: PRT
<213> ORGANISM: Syncechocystis sp.

<400> SEQUENCE: 107

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
        115                 120                 125

Glu Ala Pro Gln Glu Asp Gly Lys Ile Glu Leu His Pro Arg Gln Ser
    130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 108
<211> LENGTH: 184
<212> TYPE: PRT
<213> ORGANISM: Syncechocystis sp.

<400> SEQUENCE: 108

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30

Thr Gly Ser Gln Gly Ala Ala Ile Cys Phe Gly Glu Lys Leu Ile Leu
        35                  40                  45

Val Gly Glu Thr Pro Asp Glu Lys Ala Val Gln Tyr Leu Leu Gln Trp
    50                  55                  60

Leu Glu Asn Arg Glu Val Gln Asp Val Phe Phe Thr Ser Ser Leu Ser
65                  70                  75                  80
```

```
Gln Ile Tyr Pro Asp Ala Val Asn Phe Lys Ser Val Ala Ser Gly Leu
             85                  90                  95

Leu Ala Ile Pro Ile Ala Arg His Asn Phe Leu Leu Trp Phe Arg Pro
            100                 105                 110

Glu Val Leu Gln Ala Val Asn Trp Gly Gly Asp Pro Asn His Ala Tyr
            115                 120                 125

Glu Ala Thr Gln Glu Asp Gly Lys Ile Glu Leu His Pro Arg Gln Ser
            130                 135                 140

Phe Asp Leu Trp Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180
```

<210> SEQ ID NO 109
<211> LENGTH: 184
<212> TYPE: PRT
<213> ORGANISM: Syncechocystis sp.

<400> SEQUENCE: 109

```
Leu Ala Glu His Glu Ala Val Leu Leu Asp Lys Met Thr Thr Ala Ala
1               5                   10                  15

Asp Phe Val Glu Gly Leu Ser Asn His Pro Asp Arg Leu Leu Gly Leu
            20                  25                  30

Thr Gly Ser Gln Gly Ala Ala Ile Cys Phe Gly Glu Lys Leu Ile Leu
            35                  40                  45

Val Gly Glu Thr Pro Asp Glu Lys Ala Val Gln Tyr Leu Leu Gln Trp
        50                  55                  60

Leu Glu Asn Arg Gly Val Gln Val Val Phe Thr Ser Ser Leu Ser
65                  70                  75                  80

Arg Ile Tyr Pro Asp Ala Val Asn Phe Lys Ser Val Ala Ser Gly Leu
             85                  90                  95

Leu Ala Ile Pro Ile Ala Arg His Asn Phe Leu Leu Trp Phe Arg Pro
            100                 105                 110

Glu Val Leu Gln Thr Val Asn Trp Gly Gly Asp Pro Asn His Ala Tyr
            115                 120                 125

Glu Ala Thr Gln Glu Asp Gly Lys Ile Glu Leu His Pro Arg Gln Ser
            130                 135                 140

Phe Asp Leu Arg Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180
```

<210> SEQ ID NO 110
<211> LENGTH: 184
<212> TYPE: PRT
<213> ORGANISM: Syncechocystis sp.

<400> SEQUENCE: 110

```
Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
            20                  25                  30
```

-continued

Thr Gly Ser Gln Gly Ala Ala Ile Cys Phe Gly Glu Lys Leu Ile Leu
         35                  40                  45

Val Gly Glu Thr Pro Asp Glu Lys Ala Val Gln Tyr Leu Leu Gln Trp
 50                  55                  60

Leu Glu Asn Arg Glu Val Gln Asp Val Phe Phe Thr Ser Ser Leu Ser
 65                  70                  75                  80

Gln Ile Tyr Pro Asp Ala Val Asn Phe Lys Ser Val Ala Ser Gly Leu
                 85                  90                  95

Leu Ala Ile Pro Ile Ala Arg His Asn Phe Leu Leu Trp Phe Arg Pro
                100                 105                 110

Glu Val Leu Gln Thr Val Asn Trp Gly Gly Asp Pro Asn His Ala Tyr
             115                 120                 125

Glu Ala Thr Gln Glu Asp Gly Lys Ile Glu Leu His Pro Arg Gln Ser
         130                 135                 140

Phe Asp Leu Arg Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 111
<211> LENGTH: 184
<212> TYPE: PRT
<213> ORGANISM: Syncechocystis sp.

<400> SEQUENCE: 111

Leu Ala Glu His Glu Ala Val Leu Leu Asp Lys Met Thr Thr Ala Ala
1               5                  10                  15

Asp Phe Val Glu Gly Leu Thr Asn His Pro Asp Arg Leu Leu Gly Leu
             20                  25                  30

Thr Gly Ser Gln Gly Ala Ala Ile Cys Phe Gly Glu Lys Leu Ile Leu
         35                  40                  45

Val Gly Glu Thr Pro Asp Glu Lys Ala Val Gln Tyr Leu Leu Gln Trp
 50                  55                  60

Leu Glu Asn Arg Glu Val Gln Asp Val Phe Phe Thr Ser Ser Leu Ser
 65                  70                  75                  80

Gln Ile Tyr Pro Asp Ala Val Asn Phe Lys Ser Val Ala Ser Gly Leu
                 85                  90                  95

Leu Ala Ile Pro Ile Ala Arg His Asn Phe Leu Leu Trp Phe Arg Pro
                100                 105                 110

Glu Val Leu Gln Thr Val Asn Trp Gly Gly Asp Pro Asn His Ala Tyr
             115                 120                 125

Glu Ala Thr Gln Glu Asp Gly Lys Ile Glu Leu His Pro Arg Gln Ser
         130                 135                 140

Phe Asp Leu Cys Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
            180

<210> SEQ ID NO 112
<211> LENGTH: 184
<212> TYPE: PRT

-continued

```
<213> ORGANISM: Syncechocystis sp.

<400> SEQUENCE: 112

Leu Ala Glu His Glu Ala Val Leu Leu Asp Lys Met Thr Thr Ala Ala
1               5                   10                  15

Asp Phe Val Glu Gly Leu Thr Asn His Pro Asp Arg Leu Leu Gly Leu
                20                  25                  30

Thr Gly Ser Gln Gly Ala Ala Ile Cys Phe Gly Glu Lys Leu Ile Leu
            35                  40                  45

Val Gly Glu Thr Pro Asp Glu Lys Ala Val Gln Tyr Leu Leu Gln Trp
        50                  55                  60

Leu Glu Asn Arg Glu Val Gln Asp Val Phe Phe Thr Ser Ser Leu Ser
65                  70                  75                  80

Gln Ile Tyr Pro Asp Ala Val Asn Phe Lys Ser Val Ala Ser Gly Leu
                85                  90                  95

Leu Ala Ile Pro Ile Ala Arg His Asn Phe Leu Leu Trp Phe Arg Pro
                100                 105                 110

Glu Val Leu Gln Thr Val Asn Trp Gly Gly Asp Pro Asn His Ala Tyr
            115                 120                 125

Glu Ala Thr Gln Glu Asp Gly Lys Ile Glu Leu His Pro Arg Gln Ser
        130                 135                 140

Phe Asp Leu Phe Lys Glu Ile Val Arg Leu Gln Ser Leu Pro Trp Gln
145                 150                 155                 160

Ser Val Glu Ile Gln Ser Ala Leu Ala Leu Lys Lys Ala Ile Val Asn
                165                 170                 175

Leu Ile Leu Arg Gln Ala Glu Glu
                180
```

RED AND NEAR INFRARED FLOURESCENT PHYOTOCHROME

CROSS-REFERENCE TO RELATED APPLICATIONS

This application claims priority to and benefit of U.S. Ser. No. 60/569,310, filed on May 6, 2004, U.S. Ser. No. 60/598,661, filed on Aug. 3, 2004, and U.S. Ser. No. 60/640,867, filed on Dec. 30, 2004, all of which are incorporated herein by reference in their entirety for all purposes.

STATEMENT AS TO RIGHTS TO INVENTIONS MADE UNDER FEDERALLY SPONSORED RESEARCH AND DEVELOPMENT

This work was supported in part by Grant No: PHY-0120999 from the National Science Foundation Center for Biophotonics Science and Technology and by Grant No: GM068552-01 from the National Institutes of Health. The government of the United States of America has certain rights in this invention.

FIELD OF THE INVENTION

This invention pertains to the field of fluorescent markers. In particular, this invention provides fluorescent adducts that emit in the far red and near infra-red portion of the spectrum.

BACKGROUND OF THE INVENTION

Bilin pigments, when associated with proteins, exhibit a wide variety of photophysical properties, i.e. intense fluorescence, photochemical interconversions, and radiationless de-excitation. Differences in the protonation state, conformation and/or ionic environment of bilin pigments can significantly alter their absorption properties. In this way, the protein moiety of biliproteins tunes the spectrum of their bilin chromophore. Plants, some bacteria, and fungi contain phytochromes—self-assembling biliproteins that act as light sensors to modulate growth and development (Frankenberg and Lagarias (2003) Pp. 211-235 In: *The Porphyrin Handbook. Chlorophylls and Bilins: Biosynthesis Structure and Degradation.*, K. M. Kadish, K. M. Smith, and R. Guilard, Editors. Academic Press: New York; Lagarias and Lagarias (1989) *Proc. Natl. Acad. Sci. USA,* 86(15): 5778-5780). Phytochromes' covalently bound bilin prosthetic groups photoisomerize upon absorption of light enabling the protein to photointerconvert between two distinct species, which have absorption maxima in the red and NIR region. Unlike the intensely fluorescent phycobiliproteins, components of the photosynthetic antennae of algae, native phytochromes are non-fluorescent biliproteins because this photoconversion process is so efficient.

The optical properties of phytochromes are highly malleable, as shown by the spectral diversity of phytochromes in nature. In plants, algae, and cyanobacteria, phytochromes are associated with the linear tetrapyrroles phytochromobilin (PφB) or phycocyanobilin (PCB). Binding of an apophytochrome to the unnatural bilin precursor, phycoerythrobilin (PEB) however, affords a strongly fluorescent phytochrome known as a phytofluor, that is unable to isomerize upon light absorption (Murphy and Lagarias (1997) *Current Biology,* 7: 870-876). Phytofluors have been shown to be useful probes in living cells, however, addition of exogenous unnatural bilin precursors is generally necessary. Recently, a new class of phytochromes from bacteria and fungi was identified that attach a different bilin chromophore, biliverdin (BV), to an apparently distinct region of the apoprotein (Lamparter et al. (2002) *Proc. Natl. Acad. Sci. USA,* 99(18): 11628-11633). These studies indicate that molecular evolution has occurred in nature to produce phytochrome mutants with novel spectroscopic properties.

The jellyfish green fluorescent protein (GFP) has revolutionized cell biological studies, allowing for the visualization of protein dynamics in real-time within living cells by in frame fusion to a gene of interest. Applications of GFP and related fluorescent proteins of the GFP family include investigation of protein-protein interactions, spatial and temporal gene expression, and sub-cellular localization. GFPs have also been used to label organelles, to image pH and calcium fluxes, and to test targeting peptides (Chiesa et al. (2001) *Biochemical J.,* 355(Part 1): 1-12).

Despite their utility, as with any technology, GFPs have inherent limitations. During the maturation of the GFP chromophore, where three adjacent amino acid residues within the protein cyclize (S65, Y66, G67) and the tyrosine residue is thereafter dehydrogenated, cytotoxic hydrogen peroxide is produced (Cubitt et al. (1995) *Trends In Biochemical Sciences,* 20(11): 448-455). GFPs are typically homodimers, a property that can interfere with the native function of the fused protein of interest. GFPs are also temperature and pH-sensitive and can be highly susceptible to photobleaching and oxidation. While some of these problems have been overcome by directed evolution (Zhang et al. (2002) *Nature Reviews Molecular Cell Biology,* 3(12): 906-918), many cannot. In particular, directed evolution has been used to engineer an array of color variants of GFP ranging from blue, to cyan, to yellow (Heim and Tsien (1996) *Current Biology,* 6: 178-182). Despite the multiple engineering efforts to date, long wavelength red and NIR emitting GFP variants have not yet been isolated. The recent identification of the orange fluorescent protein DsRed (excitation maximum 558 nm, and emission maximum 583 nm) from the coral genus *Discosoma* has sparked a great deal of interest due to its longer wavelength emission properties (Matz et al. 91999) *Nature Biotechnology,* 17(10): 969-973). However, DsRed exhibits a tendency to tetramerize and long incubation periods are needed to reach steady-state fluorescence levels (Zhang et al. (2002) *Nature Reviews Molecular Cell Biology,* 3(12): 906-918).

SUMMARY OF THE INVENTION

Owing to their strong absorbance in the red (R) and near infrared (NIR) region and their ability to autocatalytically attach a chromophore, phytochromes are good substrates for engineering a Red/NIR fluorescent reporter protein. Fluorescent phytochromes with unique fluorescence excitation/emission spectra, which can be used with commonly available laser-based confocal microscopes and flow cytometers, are valuable complements to green fluorescent protein (GFP). In conjunction with GFPs, fluorescent phytochromes can serve as donor and/or acceptor molecules in fluorescence resonance energy transfer (FRET) applications for studying protein-protein interactions (Hailey et al. (2000) *Meth. Enzymology,* 351: 34-49). R/NIR emitting fluorescent proteins are also well suited for mammalian cell studies as red transmission through these tissues is more efficient. Coupled with the ability to biosynthesize a variety of natural and non-natural chromophores in bacterial cells and to infiltrate bilin chromophores successfully into mammalian, plant and yeast cells, phytochromes are useful as R and/or NIR fluorescent probes (Murphy and Lagarias (1997) *Current Biology,* 7: 870-876; Gambetta and Lagarias (2001) *Proc. Natl. Acad. Sci. USA,*

98(19): 10566-10571; Li and Lagarias (1994) *Proc. Natl. Acad. Sci. USA,* 91(26): 12535-12539).

This invention pertains to the use of a directed evolution approach to creae novel fluorescent phytochrome mutants. Error-prone PCR was employed to generate point mutations at random positions within Cph1. Mutations within the chromophore pocket that appear to sterically inhibit chromophore photoisomerization resulted in a greatly enhanced fluorescence quantum yield. Such mutants yielded far red and/or near infra-red (NIR).

Thus, in one embodiment, this invention provides an apoprotein that, when combined with a bilin, forms a biliprotein fluorophore that emits in the far-red and/or the near infra-red (NIR). The apoprotein typically comprises a Cyanobacterial phytochrome 1 Cph1(N514) protein from *Synechocystis* sp PCC 6803 having one or more mutations within its chromophore binding domains P2, P3 and/or P4 that inhibit bound chromophore photoisomerization. In certain embodiments, the apoprotein comprises a mutation in the P2 PAS domain and/or the P3 GAF domain. In certain embodiments, the apoprotein comprises a mutation in the P2 PAS domain and two mutations in the P3 GAF domain. In certain embodiments, P2 PAS domain at residue 47 (e.g., A47T), and/or a mutation in the P3 GAF domain at residue 176 (e.g., Y176H), and/or a mutation in the P3 GAF domain at residue 252 (e.g., Y176H). In certain embodiments, the apoprotein comprises the amino acid sequence depicted in FIG. 1B (SEQ ID NO:2). In certain embodiments, the apoprotein consists of the amino acid sequence depicted in FIG. 1B (SEQ ID NO:2). In certain embodiments, the apoprotein is attached to a linker (e.g. a carbon linker, a peptide linker, etc.). Also provided are nucleic acids comprising a nucleotide sequence that encodes a mutant apoprotein as described herein. In certain embodiments, the nucleic acid comprises the nucleotide sequence depicted in FIG. 1A (SEQ ID NO:1). In certain embodiments, the nucleic acid consists of the nucleotide sequence depicted in FIG. 1A (SEQ ID NO:1). The nucleic acid can comprise a vector.

In still another embodiment this invention provides a cell or cell line that expresses a mutant apoprotein as described herein. In certain embodiments, the cell or cell line produces an endogenous bilin and/or biliverdin.

Also provided is a fusion protein comprising a mutant apoprotein as described herein. In certain embodiments, the heterologous protein is attached directly to said apoprotein. In certain embodiments, the heterologous protein is attached to the apoprotein through a peptide linker (e.g. Gly$_4$Ser)$_3$ (SEQ ID NO:52).

In certain embodiments, this invention provides a fluorescent adduct comprising a mutant apoprotein as described herein combined with a bilin and/or a biliverdin. In certain embodiments, the bilin is selected from the group consisting of phycocyanobilin (PCB), phytochromobilin (PΦB), biliverdin IX (BV) isomer BV IXα, biliverdin IX (BV) isomer BV IXβ, biliverdin IX (BV) isomer BV IXγ, and biliverdin IX (BV) isomer BV IXδ.

This invention also provides a method of detecting a biological molecule. The method typically involves providing the biological molecule attached to a mutant apoprotein as described herein, contacting the apoprotein with a bilin; and detecting fluorescence of an adduct formed by the bilin and the apoprotein. In certain embodiments, the detecting comprises detecting fluorescence in the far red and/or the near infra-red (NIR). In certain embodiments, the biological molecule is a protein and said providing comprises expressing said protein as a fusion protein with said apoprotein. In certain embodiments, the biological molecule is a nucleic acid and said providing comprises chemically conjugating the nucleic acid to the apoprotein. In certain embodiments, the biological molecule is a single chain antibody and said providing comprises expressing the single chain antibody as a fusion protein with the apoprotein. In certain embodiments, the bilin is selected from the group consisting of phycocyanobilin (PCB), phytochromobilin (PΦB), biliverdin IX (BV) isomer BV IXα, biliverdin IX (BV) isomer BV IXβ, biliverdin IX (BV) isomer BV IXγ, and biliverdin IX (BV) isomer BV IXδ.

Also provided is a method of detecting a biological molecule. The method typically involves providing the biological molecule attached to an apoprotein-bilin adduct comprising an mutant apoprotein as described herein and a bilin and/or biliverdin; and detecting fluorescence of an adduct formed by said bilin and/or biliverdin and the apoprotein. In certain embodiments, the detecting comprises detecting fluorescence in the far red and/or the near infra-red (NIR). In certain embodiments, the bilin is selected from the group consisting of phycocyanobilin (PCB), phytochromobilin (PΦB), biliverdin IX (BV) isomer BV IXα, biliverdin IX (BV) isomer BV IXβ, biliverdin IX (BV) isomer BV IXγ, and biliverdin IX (BV) isomer BV IXδ. In certain embodiments, the biological molecule is selected from the group consisting of a protein, an antibody, a nucleic acid, a sugar, a lectin, and a fat.

In still another embodiment this invention provides an apoprotein that when combined with a bilin forms a fluorophore that emits in the far red and/or the near infra-red (NIR). The apoprotein typically comprises a phytochrome apoprotein comprising one or more mutations within the chromophore pocket that sterically inhibit bound chromophore photoisomerization. In certain embodiments, the apoprotein is an apoprotein selected from the group consisting of a bacterial phytochrome, a plant phytochrome, and an algal phytochrome.

DEFINITIONS

The term "fluorescent adduct" refers to a fluorescent molecule (i.e., one capable of absorbing light of one wavelength and emitting light of a second wavelength) comprising an "apoprotein" (also referred to as an apophytochrome) component joined to, or associated with, a "bilin" or "biliverdin" component, both of which are described herein. The fluorescent phytochrome-bilin conjugates (e.g., phytochrome-PEB adducts), or biliverdin adducts, are also referred to herein as "phytofluors". The manner in which the two components are joined to form an adduct is irrelevant to the present invention. Typically, the two components spontaneously form an adduct through covalent interactions. The components can also be deliberately linked through covalent bonds (e.g., through the use of crosslinking reagents). The fluorescent adducts of this invention do not require pairing of an apoprotein with its corresponding native bilin. To the contrary, the invention contemplates adducts consisting of naturally occurring or engineered apoproteins with bilins derived from different organisms, or with non-naturally occurring synthetic linear pyrroles.

The terms "apoprotein", "apophytochrome", or "apoprotein polypeptide", as used herein, refer to polypeptides derived from eukaryotes, such as vascular plants, non-vascular plants, and algae, or from prokaryotes, such as cyanobacterial and/or mutants thereof. The term encompasses both naturally occurring apoproteins and variant polypeptides derived through mutagenesis. The apoproteins have a hydrophobic pocket, referred to as chromophore binding site, capable of forming an adduct with a bilin component. The apoproteins of the invention can be homodimeric proteins about 1100 amino acids in length, each subunit being composed of two major domains. The globular 70 kD N-terminal domain contains the hydrophobic pocket, while the more elongated 55 kD carboxyl terminal domain contains the sites at which the two subunits are associated. Apophytochromes can be readily identified by one of skill in the arts e.g., by comparison of the polypeptide sequence in question with an apophytochrome consensus sequence such as that provided in PCT publications WO 98/05944, WO 00/56355, and WO 01/94548 using standard sequence comparison methodologies. For a general discussion of apoprotein structure and function, see, Quail et al. (1997) in *Plant Cell and Environment*, 20: 657-665.

The term "bilin" as used herein refers to linear polypyrroles (e.g., di-, tri-, or tetrapyrroles) capable of fluorescing when associated with an apoprotein. Typically, the bilin components of the invention are isolated from vascular plants, algae, or cyanobacteria according to standard techniques. The bilin components can also be synthesized de novo. For a general discussion of bilins useful in the present invention see, Falk (1989) Pp. 355-399 in: *The Chemistry of Linear Oligopyrroles and Bile Pigments*. pp 355-399. Springer-Verlag, Vienna. Various bilins include, but are not limited to phycocyanobilin (PCB), phytochromobilin (PΦB), and any of the four biliverdin IX (BV) isomers—BV IXα, IXβ, IXγ or IXϑ.

The term "chromophore domain" or "minimal chromophore domain" refers to the apoprotein N-terminal subsequence sufficient for lyase activity; the ability to spontaneously assemble in the presence of a bilin to form a phytofluor. Chromophore domains typically comprise less than 600 amino acids of the N terminus of the apoprotein, preferably less than about 515 amino acids, more preferably less than about 450 amino acids and most preferably less than about 400, 390, or even 350 N-terminal amino acids. One preferred chromophore domain comprises the 514 N-terminal amino acids of a cyanobacterial phytochrome.

The phrase "far red" when referring to emission of a fluorescent adduct (e.g., phytofluor) refers to an emission spectrum where there is an emission peak or emission maximum at a wavelength greater than about 650 nm and less than about 700 nm. The phrase "near infra-red (NIR)" when referring to emission of a fluorescent adduct (e.g., phytofluor) refers to an emission spectrum where there is an emission peak or emission maximum at a wavelength greater than about 700 nm.

A "mutated apoprotein" is an apoprotein that differs from the native apoprotein in one or more amino acids (e.g. has one or more amino acid substitutions). An amino acid substitution can be indicated by the nomenclature "A000B" where "A" is the amino acid found at position "000" in the native protein and B is the amino acid found at that position in the mutated protein.

The term "vector" refers to a replicon, including, but not limited to a plasmid, phage, or cosmid, to which another DNA segment may be attached so as to bring about the replication of the attached segment. Vectors include both the expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10): 1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644, 048), phosphorodithioate (Briu et al. (1989) *J. Am. Chem. Soc.* 111:2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469, 863; Angew (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Sanghui and Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034, 506, and Chapters 6 and 7, ASC Symposium Series 580, *Carbohydrate Modifications in Antisense Research*, Ed. Sanghui and Cook. Nucleic acids containing one or more carbocyclic sugars are also included within the definition of nucleic acids (see Jenkins et al. (1995), *Chem. Soc. Rev.* pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "conservative substitution" is used herein to refer to replacement of amino acids in a protein with different amino acids that do not substantially change the functional properties of the protein. Thus, for example, a polar amino acid might be substituted for a polar amino acid, a non-polar amino acid for a non-polar amino acid, and so forth. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

A biological "binding partner" or a member of a "binding pair" refers to molecules that specifically bind other molecules to form a binding complex such as antibody-antigen, lectin-carbohydrate, nucleic acid-nucleic acid, biotin-avidin, etc.

The term "specifically binds", as used herein, when referring to a biomolecule (e.g., protein, nucleic acid, antibody, etc.), refers to a binding reaction which is determinative of the presence of a specific biomolecule within a heterogeneous population of proteins and/or other biologics. Thus, under designated conditions (e.g. immunoassay conditions in the case of an antibody), the specified ligand or antibody binds to its particular "target" biomolecule (e.g. a receptor protein) and does not bind in a significant amount to other proteins or other biomolecules present in the sample, or to other proteins or other biomolecules with which the ligand or antibody may come in contact in an organism.

The term "antibody", as used herein, includes various forms of modified or altered antibodies. Such forms include, but are not limited to, an intact immunoglobulin, an Fv fragment containing only the light and heavy chain variable regions, an Fv fragment linked by a disulfide bond (Brinkmann, et al. (1993) *Proc. Natl. Acad. Sci. USA*, 90: 547-551), an Fab or (Fab)'$_2$ fragment containing the variable regions and parts of the constant regions, a single-chain antibody and the like (Bird et al. (1988) *Science* 242: 424-426; Huston et al. (1988) *Proc. Nat. Acad. Sci. USA* 85: 5879-5883). The antibody may be of animal (especially hamster, mouse, rat, rabbit, pig, or goat) or human origin or may be chimeric (Morrison et al., *Proc Nat. Acad. Sci. USA* 81: 6851-6855 (1984)) or humanized (Jones et al. (1986) *Nature* 321: 522-525, and published UK patent application No: 8707252). Methods of producing antibodies suitable for use in the present invention are well known to those skilled in the art and can be found described in such publications as Harlow & Lane, *Antibodies: A Laboratory Manual*, Cold Spring Harbor Laboratory (1988), and Asai, *Methods in Cell Biology Vol. 37: Antibodies in Cell Biology*, Academic Press, Inc. N.Y. (1993).

The term "heterologous" when used with reference to a nucleic acid indicates that the nucleic acid is in a non-native state. The heterologous nucleic acid can be a modification (e.g., contain a deletion, mutation, insertion) of the native nucleic acid or can include or be replaced by a nucleic acid sequence not found in the resulting state in nature. Thus a virus containing a heterologous nucleic acid can contain a nucleic acid from a source other than that virus, or a nucleic acid from the same virus where the nucleic acid is reintroduced into the virus (e.g., after being deliberately modified).

BRIEF DESCRIPTION OF THE DRAWINGS

FIGS. 1A and 1B show the DNA and protein sequences of RR-1 Cph1(N514). FIG. 1A shows the nucleotide sequence (SEQ ID NO:1) of RubyRed-1 determined by sequencing (1,542 bp; 3 bp changes: G to A, T to C, and T to A). FIG. 1B shows the amino acid sequence (SEQ ID NO:2) of RubyRed-1 derived from the nucleotide sequence (514 aa; 3 amino acid changes: AA47 A to T, AA176 Y to H, and AA252 I to N)

FIGS. 2A and 2B show DNA and protein sequences of wildtype Cph1(N514). FIG. 2A shows the nucleotide sequence (SEQ ID NO:3) of Cph1(N514) from *Syncechocystis* sp. PCC6803 (1,542 bp; gene from which RubyRed-1 was derived). FIG. 2B shows the amino acid sequence (SEQ ID NO:4) of Cph1(N514) from *Syncechocystis* sp. (PCC6803, 514 aa).

FIG. 3 illustrates the mutations found in Ruby Red 1 (RR-1).

FIG. 10A: The proposed structure of the Pr and Pfr chromophores of plant ($R_{18}$=vinyl) and cyanobacterial ($R_{18}$=ethyl) phytochromes are based on vibrational spectroscopy (28, 29) and semi-empirical vibrational energy calculations (30, 31). The Pr to Pfr conversion is thought to involve large motions—a Z-to-E configurational isomerization of the C15 double bond (labeled a) followed by rotation around the C14-C15 bond (labeled b), while the reverse reaction appears to be a concerted configurational and conformational inversion (labeled c). FIG. 10B: Structural model of the Cph1 phytochrome consisting of the three related PAS, GAF, PHY domains terminated with the HKD (histidine kinase domain) module, and the truncated Cph1 photosensory construct used herein which lacks the HKD domain. Four mutagenesis libraries were generated from either single domains or a combination of the three photosensory domains. These libraries were co-expressed in *E. coli* with the bilin biosynthetic plasmid for the production of holo-phy mutants in vivo. The holoproteins were then analyzed for alterations in their absorption properties using spectroscopy or gain of function fluorescence using FACS analysis. FIG. 10C: The position and residue change of the 21 mutants having single amino acid substitutions identified from the PHY library screen. The alleles are colored with respect to phenotypic class: black—WT, purple—Mutant Class I, red—Mutant Class II, blue—Mutant Class III, and teal—Mutant Class IV. The pink bar designates the conserved HisG insert that is present in the PHY domain of all know phytochromes.

FIG. 11A: Purified WT and PR-1 PCB adducts imaged in white light (left) or ultra violet light (right). FIG. 11B: Comparative flow cytometry analysis of PR-1 and WT Cph1D in PCB-producing cell lines. FIG. 11C: The three amino acid substitutions identified in the PR-1 mutant are shown in WT Cph1. FIG. 11D: Colony fluorimaging assay of WT, PR-1 and the 6 possible PR-1 single and double amino acid substitution combinations as PCB adducts produced in *E. coli*. The membrane was imaged under ultraviolet light to observe fluorescence. See Example 2, Materials and Methods for details (17).

FIG. 12A: Absorbance difference spectra of Cph1 (dashed line) and PR-1 (solid line) as either the PCB (left) or PB adduct (right). FIG. 12B: Fluorescence excitation (solid line) and emission (dashed line) spectra of the PR-1 PCB (left) or PB (right) adduct. FIG. 12C: Pr absorption spectra of Cph1 (dashed line) and PR-1 (solid line) as either the PCB (left) or PB adducts (right).

FIG. 14 shows amino acid alignments of all sequenced PHY domain mutants categorized into five phenotypic classes. A) Mutants with WT Cph1 spectral properties. The amino acid residues noted under the consensus sequence are all of the substitutions that had no affect on the spectral properties of Cph1, totaling 30% of the PHY domain. B) Mutant Class I (MI) having both Pr and Pfr spectra shifted to the blue. C) Mutant Class II (MII) having both Pr and Pfr spectrum shifted to the blue as well as a reduction in photoconversion. D) Mutant Class III (MIII) having only the Pr spectrum shifted to the blue. E) Mutant Class IV (MIV) having only the Pfr spectrum shifted to the blue and a large reduction in the amount of Pfr formed at photoequilibrium. (32) (WT-1: SEQ ID NO: 53, WT-2: SEQ ID NO: 54, WT-3: SEQ ID NO: 55, WT-4: SEQ ID NO: 56, WT-5: SEQ ID NO: 57, WT-6: SEQ ID NO: 58, WT-7: SEQ ID NO: 59, WT-8: SEQ ID NO: 60, WT-9a: SEQ ID NO: 61, WT-10: SEQ ID NO: 62, WT-11a: SEQ ID NO: 63, WT-12: SEQ ID NO: 64, WT-13a: SEQ ID NO: 65, WT-14: SEQ ID NO: 66, WT-15: SEQ ID NO: 67, WT-16: SEQ ID NO: 68, WT-17: SEQ ID NO: 69, WT-18: SEQ ID NO: 70, WT-19: SEQ ID NO: 71, WT-20: SEQ ID NO: 72, WT-21: SEQ ID NO: 73, WT-22a: SEQ ID NO: 74, WT-23: SEQ ID NO: 75, WT-24: SEQ ID NO: 76, NS-6: SEQ ID NO: 77, WTConsen: SEQ ID NO: 78, Consensus: SEQ ID NO: 79, MI-1a: SEQ ID NO: 80, MI-2: SEQ ID NO: 81, MI-3: SEQ ID NO: 82, MI-4: SEQ ID NO: 83, MI-5: SEQ ID NO: 84, MI-6: SEQ ID NO: 85, MI-7: SEQ ID NO: 86, MI-8: SEQ ID NO: 87, MI-9: SEQ ID NO: 88, MI-10: SEQ ID NO: 89, MI-11: SEQ ID NO: 90, MI-12: SEQ ID NO: 91, MI-8a: SEQ ID NO: 92, NS-2: SEQ ID NO: 93, NS-3: SEQ ID NO: 94, NS-4: SEQ ID NO: 95, NS-5: SEQ ID NO: 96, MII-1: SEQ ID NO: 97, MII-2: SEQ ID NO: 98, MII-3: SEQ ID NO: 99, SEQ ID NO: 100, MII-4a: SEQ ID NO: 101, MII-4b: SEQ ID NO: 102, MII-5a: SEQ ID NO: 103, NS-1: SEQ ID NO: 104, MIII-1: SEQ ID NO: 105, MIII-2: SEQ ID NO: 106, MIII-2a: SEQ ID NO: 107, MIII-3a: SEQ ID NO: 108, MW-1: SEQ ID NO: 109, MW-1a: SEQ ID NO: 110, MIV-1b: SEQ ID NO: 111, MIV-1c: SEQ ID NO: 112).

FIG. 16. Recombinant *Arabidopsis* phyA_N599 WT and Y242H Mutant Spectra. Panel A: Normalized corrected fluorescence excitation (blue) and emission (green) spectra of crude protein extracts from *E. coli* cells expressing atphyA_Y242H_N599ST. Fluorescence emission and excitation maxima were 650 nm and 673 nm, respectively. Panel B: Phytochrome difference spectra from *E. coli* cells expressing atphyA_WT_N599ST (Amax=649 nm/Amin=711 nm; solid) or atphyA_Y242H_N599ST (Amax=nd/Amin=nd; dashed).

FIG. 17. Full length Cph1 Y176H mutant is fluorescent. Panel A: Normalized absorption spectra of his-tagged FL Cph1WT as Pr (max=663 nm; green), FL Cph1WT Pfr (blue) and FL Cph1Y176H (max=644 nm; red) as Pr. Panel B: Normalized phytochrome difference spectra FL Cph1WT (Amax=657 nm/Amin=704 nm; blue) and FL Cph1Y176H Pfr (Amax=647 nm/Amin=696 nm; green). Panel C: Normalized corrected fluorescence spectra FL Cph1Y176H (EX 652 nm:blue/EM 676 nm:green) and FL Cph1WT (EX 650 nm:red/EM 676 nm:yellow)

DETAILED DESCRIPTION

Figure 4:
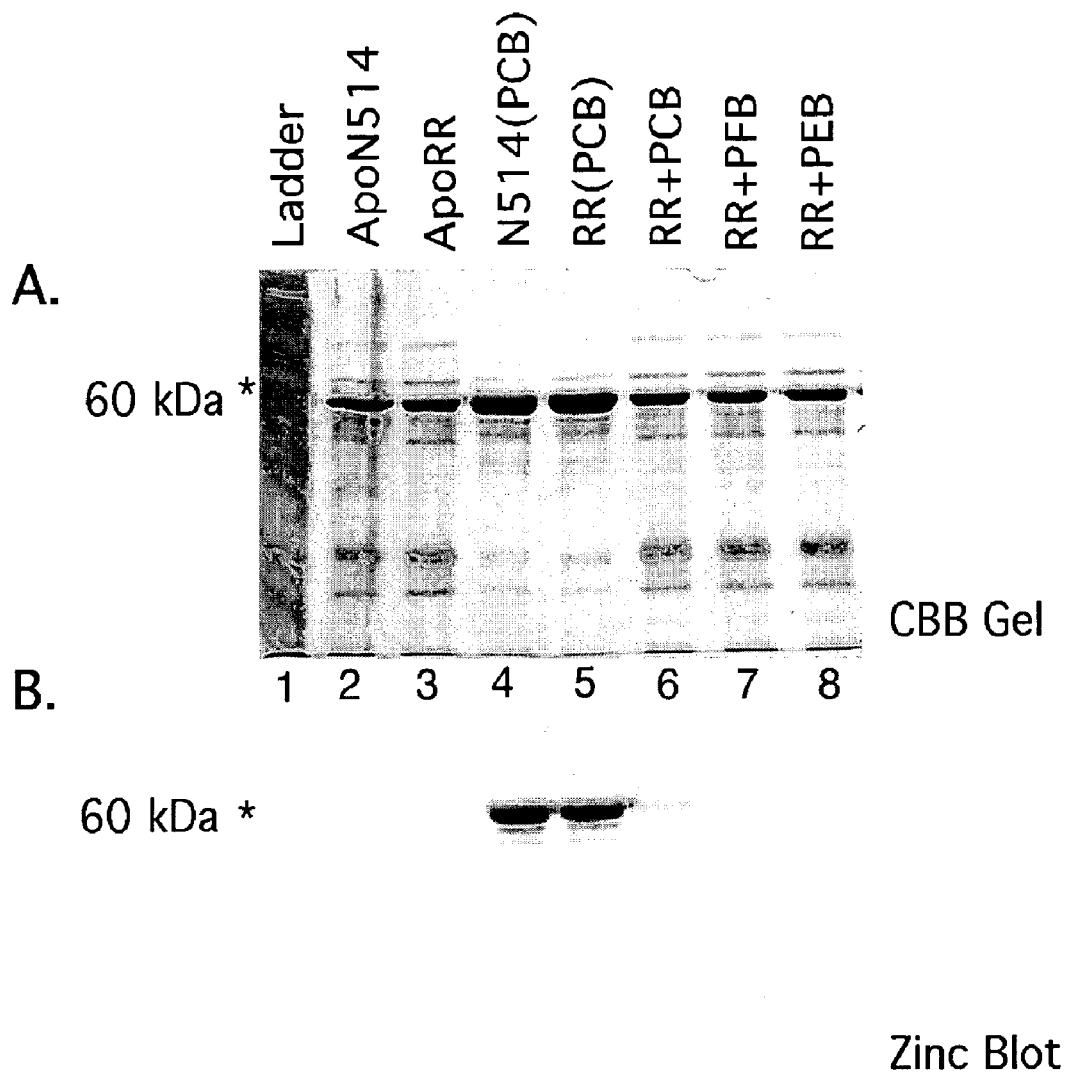
FIG. 4, panels A and B, show an SDS PAGE analysis of recombinant RR-1 and WT Cph1(N514). Panel A: Coomassie Brilliant Blue stained gel. B. Zinc blot fluorescence visualization under UV light. Lane 1 MW standards; lane 2, WT Cph1(N514) apoprotein; lane 3, RR-1 apoprotein; lane 4, WT Cph1(N514):PCB holoprotein; lane 5, RR-1:PCB holoprotein; lanes 6-8, RR-1 apoprotein after 30 min incubation with PCB, PΦB and PEB respectively.

Labeling is a tool for marking a protein, cell, or organism of interest and plays a prominent role in many biochemistry, molecular biology and medical diagnostic applications. A variety of different labels have been developed, including radiolabels, chromolabels, fluorescent labels, chemiluminescent labels, etc. There is continued interest, however, in the development of new labels. Of particular interest is the development of new protein labels, including chromo- and/or fluorescent protein labels.

This invention pertains to the surprising discovery that phytochrome and biliverdin apoproteins can be mutated so that when they are combined with bilins they form fluorescent adducts that are highly fluorescent in the far red and near infra-red region of the spectrum. In certain preferred embodiments, the phytochrome apoproteins are mutated in the chromophore binding domains, e.g., P2, P3 and/or P4 such that bound chromophore photoisomerization is inhibited. In certain embodiments, the apoprotein is a Cyanobacterial phytochrome (e.g., Cph1(N514) protein from *Synechocystis* sp PCC 6803).

The fluorescent adducts, also referred to herein as phytofluors, useful as fluorescent markers or labels in a variety of contexts. Fluorescent markers that emit in the far red and near infra-red (NIR) region of the spectrum offer a number of advantages over the "traditional" green fluorescent protein (GFP) markers. By emitting in the near red and NIR region, the fluorescent adducts described herein virtually eliminate the autofluorescence (e.g., from the media, culture dish, or cellular components) that masks a GFP variant's fluorescence. The noisy background found in the green portion of the spectrum makes it difficult to visualize low-abundance proteins or dimly emitting fusions. Because the fluorescent adducts described herein fluoresce outside the range of most autofluorescence, they stand out sharply from the background, giving the best possible signal-to-noise ratio.

For in vivo labeling, the fluorescent adducts described herein offer a further advantage over fluorescent proteins. Tissues specifically absorb the short-wavelength blues and greens of GFP variants, thereby reducing the amount of light that transmits in vivo. Because tissues absorb less energy at longer wavelengths, the red fluorescence of the adducts described herein transmits clearly through tissues. This characteristic makes the phytofluors of this invention a valuable tool for labeling tissues that have been hard to label with GFP variants.

In addition the red-emitting phytofluors of this invention are well suited for multiple labeling. The emission spectra is clearly distinct from most GFP variants. Consequently, they can be easily distinguished from GFP variants by fluorescence microscopy or flow cytometry using the appropriate filters. This spectrum makes the red phytofluors of this invention ideal for colabeling with other phytofluors or green fluorescent proteins. Together, the red phytofluors described herein and other phytofluors or green fluorescent proteins are excellent tools for a variety of applications, including, but not limited to labeling two or more proteins in a single cell or tissue, monitoring gene expression simultaneously from two or more different reporters, analyzing mixed cell populations by flow cytometry, and the like.

The phytofluors described herein, typically comprise an apoprotein component (e.g. an oat or cyanobacterial apophytochrome) joined to a bilin component (e.g., phycoerythrobilin (PEB)). The phytofluors (fluorescent adducts) can be chemically conjugated or fused (i.e. recombinantly expressed as a fusion protein) to a subject moiety that is to be so labeled. In a preferred embodiment the labeled moiety is a member of a biological binding pair for use in any known or later discovered technique involving fluorescent labeling of analytes or other moieties.

The apoproteins and bilins forming the fluorescent phytofluors of this invention can be modified from natural sources to provide the desired far red and/or near infra-red emission characteristics. These compositions find use for labeling of virtually any molecule or material that is chemically and/or biologically compatible with the fluorescent adducts. The phytofluors are well suited for labeling biological molecules and are particularly useful for labeling a biochemical binding-pair member so that the resulting conjugates or fusions can be used in assays involving non-covalent binding to the complementary member of the specific binding pair. A wide variety of methods involve competitive or non-competitive binding of ligand to receptor for detection, analysis, or measurement of the presence of ligand or receptor.

Thus, for example, in one embodiment, this invention provides for antibodies or antibody fragments to which the fluorescent adducts (phytofluors) of this invention are joined (either covalently or non-covalently). The antibodies are capable of specifically binding to the antigen to which they are directed. Detection of the presence, absence, or amount of fluorescence of the antibody-bound fluorescent adduct of this invention provides an indication of presence, absence, or amount of analyte to which the antibody is directed.

Similarly phytofluor labeled antibodies, or other ligands, can be used in immunohistochemical applications. In this context, fluorescent adduct labeled antibodies are used to probe cells, tissues, and sections thereof. When the subject sample is contacted with the labeled ligand, the ligand binds and localizes to specific regions of the sample in which the target molecule (the molecule or moiety recognized by the ligand) is located. Localization and/or quantification of the fluorescent signal produced by the attached phytofluor provides information concerning the location and/or quantity of the target molecule in the sample. One of skill in the art will appreciate that the phytofluors of this invention are also well suited for in situ and in vivo labeling of molecules, cells, and cellular components.

The phytofluor labels of this invention can be attached to a wide variety of biological molecules in addition to antibodies. This may include proteins, in particular proteins recognized by particular antibodies, receptors, enzymes, or other ligands, nucleic acids (e.g., single or double stranded DNA, cDNA, mRNA, cRNA, rRNA, tRNA, etc.) various sugars and polysaccharides, lectins, enzymes, and the like. Uses of the various labeled biomolecules will be readily apparent to one of skill in the art. Thus, for example, labeled nucleic acids can be used as probes to specifically detect and/or quantify the presence of the complementary nucleic acid in, for example, a Southern blot. In various embodiments, the apoprotein component of the phytofluor can be expressed in fusion with a heterologous protein and in this context can act as a reporter molecule (e.g., when contacted with a (native or exogenous) bilin) to identify gene activations, protein expression, and/or protein localization within a cell. Similarly, the apoprotein can act to identify particular cell populations in cell sorting procedures.

The phytofluors of this invention can be attached to non-biological molecules and various articles of manufacture. Thus, for example where it is desired to associate an article of manufacture with a particular manufacturer, distributor, or supplier, the phytofluor, or simply one component of the phytofluor can be attached to the subject article. Later "development" (e.g., by addition of the second component such as bilin or apoprotein) and exposure to an appropriate light source will provide a fluorescent signal identifying the article as one from a source of such labeled articles.

In another embodiment, the phytofluors of this invention can be used for probing protein-protein interactions. In a preferred embodiment, two apoprotein cDNA constructs are used. The first construct will encode an apoprotein species whose assembly with a given bilin emits at a well defined wavelength (donor). The second construct will encode an apoprotein species whose assembly with the same, or different, bilin produces a fluorescent species that both absorbs and emits light to longer wavelengths (acceptor). Protein-protein interaction between two proteins of interest (e.g., protein X and protein Y) is identified following their co-expression as translational fusions with apoprotein in constructs 1 (donor) and 2 (acceptor) using fluorescence energy transfer from the shorter wavelength-absorbing donor species to the longer wavelength-absorbing acceptor species. In a preferred embodiment, the fluorescent phytochrome species are selected to have good spectral overlap. Proximity caused by the protein-protein interaction between the translational fused proteins X and Y will then permit fluorescence energy transfer thereby providing an indication of proximity between protein X and protein Y. This application can utilize the uptake of exogenous bilin pigment into living cells, or alternatively, may use endogenously expressed bilins in various organisms and cell types.

In an illustrative application, a yeast or *E. coli* strain containing donor construct 1, engineered to produce a fluorescent chimeric protein "bait" with a known cDNA sequence, is co-transformed, simultaneously or sequentially, with a "prey" cDNA library (i.e., plasmid or phage). The "prey" cDNA library is constructed using acceptor construct 2 for expression of apoprotein-protein fusions which yield fluorescent tagged protein products in the presence of the correct bilin. Co-transformation events that express "prey" proteins in the library that interact with the expressed "bait" polypeptide can be identified by illuminating the shorter wavelength absorbing donor phytofluor species and viewing emission from the longer wavelength acceptor phytofluor emitting species. Actinic illumination for this screen can either be obtained with a quartz halogen projector lamp filtered through narrow bandpass filters or with a laser source and fluorescence detection of colonies using digital imaging technology (Arkin et al. (1990) *Bio-Technology* 8: 746-749). Fluorescent activated cell sorting (FACS) can also be used to identify cells co-expressing interacting donor and acceptor proteins.

In another illustrative application, chimeric apoprotein-protein X cDNA (where protein X is any protein of interest) are expressed in transgenic eukaryotes (yeast, plants, *Drosophila*, etc.) in order to study the subcellular localization of protein X in situ. Following feeding of exogenous bilin, subcellular localization can be performed using fluorescence microscopy (e.g., laser confocal microscopy).

In certain preferred embodiments, the phytofluors of this invention are used as in vitro or in vivo labels in a manner analogous to the use of Green Fluorescent Protein (GFP). This typically involves transfecting a cell with a nucleic acid encoding an apoprotein in such a manner that the cell expresses the apoprotein (e.g., the nucleic acid is a component of an expression cassette). When the apoprotein is contacted with the appropriate bilin, supplied either exogenously or produced endogenously, the phytofluor (fluorescent adduct) self assembles and thereby produces a fluorescent marker.

Uses of such a marker are well known to those of skill in the art (see, e.g., U.S. Pat. No. 5,491,084 which describes uses of GFP). In one preferred embodiment, the phytofluor can be used as a marker to identify transfected cells. In the simplest approach, a nucleic acid expressing an apoprotein such as that described in Example 1 can be provided as a marker in a vector. The apoprotein, along with the cloned protein of interest, will be expressed in the transfected host. Application of the appropriate exogenous bilin will cause formation of the fluorescent adduct permitting ready detection of the transformed cell. Alternatively, the apoprotein can form an adduct with an endogenous bilin produced by the transformed organism (e.g., a plant cell). In this embodiment, the apoprotein will be a variant which forms fluorescent adduct when combined with the naturally occurring bilin.

Based on the disclosure provided herein, one of skill will readily appreciate that there are numerous other uses to which the phytofluors (fluorescent adducts) of this invention can be applied.

Mutant Apoprotein Polypeptides.

The apoprotein polypeptides of this invention preferably comprise mutated apoproteins that, when combined with a bilin or biliverdin, form a fluorophore that emits in the far-red and/or the near infra-red (NIR). In certain preferred embodiments, the mutation comprises one or more mutations within the chromophore chromophore binding domains, e.g., P2, P3 and/or P4 that sterically inhibit bound chromophore photoisomerization.

Apoprotein polypeptides to be mutated for use in the phytofluors of this invention include, but are not limited to apoproteins from bacterial phytochrome, plant phytochromes, and algal phytochromes.

In higher plants, apoprotein polypeptides are encoded by a gene family of at least five structurally related members designated PHYA-PHYE (see, Terry et al. (1993) *Arch. Biochem. Biophys.* 306:1-15 and Scharrock et al. (1989) *Genes Dev.* 3:1745-1757). The primary structures of all apoproteins are very similar, with a polypeptide of about 1100 amino acids in length (Quail et al. (1991) Pp. 13-38 In: *Phytochrome Properties and Biological Action*, Thomas and Johnson eds. Springer-Verlag, Berlin). The native protein is a homodimer; the individual subunits being composed of two major domains. The globular 70 kD N-terminal domain contains the hydrophobic pocket in which the bilin chromophore resides (Gabriel et al. (1993) *J. Theor. Biol.* 44:617-645. The more elongated 55 kD carboxyl terminal domain contains the sites at which the two subunits are associated (Edgerton et al. (1992) *Plant Cell* 4:161-171). This domain is also responsible for phytochrome function, although both domains are thought to participate in the signal transmission process in native phytochrome.

Suitable mutants that when combined with a bilin and/or biliverdin form fluorescent adducts that emit in the far red and/or near infra-red can be identified by producing libraries of mutants (e.g., mutants in the chromophore binding domains P2, P3 and/or P4) forming adducts with appropriate bilins (e.g. PΦB) and screening the adducts for desired emission spectra. The mutant libraries can be produced by any of a number of convenient methods, e.g. sited directed and/or random mutagenesis. The construction and screening of such mutant libraries is illustrated herein in Example 1.

In certain embodiments, the mutations include the same mutations identified herein, e.g., A47T and/or Y176H, and/or I252N. In certain embodiments, the mutations are in homologous, residues. Without being bound by a particular theory, it is believed that these mutations, particularly the tyrosine to histidine substitution at residue 176, will produce red fluorescing BV adducts.

Expression Systems.

In certain embodiments, the apoprotein will be expressed as a component of a fusion protein to identify gene activation, and/or expression, and/or localization of the subject protein and/or to permit isolation of that protein or cells expressing that protein. The fluorescent adduct can be formed by reaction of the apoprotein component of the fusion protein with an endogenous bilin or biliverdin or with an exogenous supplied bilini or biliverdin.

In certain embodiments, the apoprotein is expressed alone and isolated and then combined with a bilin or biliverdin to form a fluorescent adduct that can be chemically conjugated to essentially any moiety of interest.

In certain preferred embodiments, the apoprotein mutants and/or nucleic acids encoding the apoprotein mutants are prepared using standard techniques well known to those of skill in the art. Using the sequence information for the desired mutant apoprotein, nucleic acids encoding the desired apoprotein can be chemically synthesized according to a number of standard methods known to those of skill in the art. Oligonucleotide synthesis, is preferably carried out on commercially available solid phase oligonucleotide synthesis machines (Needham-VanDevanter et al. (1984) *Nucleic Acids Res.* 12: 6159-6168) or manually synthesized using the solid phase phosphoramidite triester method described by Beaucage et. al. (Beaucage et. al. (1981) *Tetrahedron Letts.* 22(20): 1859-1862). Alternatively, nucleic acids encoding the apoprotein be amplified and/or cloned according to standard methods.

Molecular cloning techniques to achieve these ends are known in the art. A wide variety of cloning and in vitro amplification methods are suitable for the construction of recombinant nucleic acids. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) *Proc. Natl Acad. Sci. USA* 86: 10029-10033. In addition, detailed protocols for the expression of the apoproteins of this invention are provided herein in the Examples.

Preparation of Bilins.

In certain embodiments, particularly in certain in vivo applications, the apoprotein combines with an endogenous bilin and/or biliverdin to produce the fluorescent adduct. In certain embodiments, the bilin and/or biliverdin can be exogenously supplied.

The bilin component of the adducts of the invention can be isolated from the appropriate natural source or synthesized according to techniques known in the art. Methods for synthesis of the dimethyl ester of phytochromobilin are described for instance in Weller et al. (1980) *Chem. Ber.* 113:1603-1611. Conversion of the dimethyl ester to the free acid can be accomplished according to known techniques (see, e.g., Greene and Wuts, *Protective Groups in Organic Synthesis* 2d ed. (John Wiley and Sons, 1991).

Methods for isolating bilins including phytochromobilin, phycocyanobilin (PCB), and phycoerythrobilin (PEB) from natural sources are also described in the art. For instance crude phycocyanobilin can be prepared from *Spirulina platensis* as described by Terry et al. (1993) *J. Biol. Chem.* 268: 26099-26106. Crude phytochromobilin and PEB can be prepared by methanolysis of *Porphyridium cruentum* cells as described by Cornejo et al. (1992) *J. Biol. Chem.* 267: 14790-14798.

Attachment of Fluorescent Adducts (Phytofluors) to Subject Molecules.

Tagged Moiety.

The conjugates of the subject invention are fluorescent adducts bound either covalently or non-covalently, normally covalently, to a particular moiety to be detected. Virtually any moiety to which it is desired to attach a fluorescent label is suitable. The moiety can be a macroscopic article such as an article of manufacture that is to be fluorescently tagged, or alternatively, the moiety can be microscopic, such as cell, an organelle, or a single molecule.

Virtually any molecule can be tagged. Typically, however, the moiety to be tagged and detected will be a biomolecule such as a polypeptide, oligopeptide, nucleic acid, polysaccharide, oligosaccharide, lipid, and the like. For instance, the subject molecule may be a ligand or receptor. A "ligand", as used herein, refers generally to all molecules capable of reacting with or otherwise recognizing or binding to a second biological macromolecule e.g., a receptor, antigen, or other molecule on a target cell. Specifically, examples of ligands include, but are not limited to antibodies, lymphokines, cytokines, receptor proteins (e.g., CD4, CD8), solubilized receptor proteins (e.g., solubilized T-cell receptor, soluble CD4), hormones, growth factors, and the like which specifically bind particular target cells. A "growth factor" as used herein refers to a protein ligand that stimulates cell division or differentiation or inhibits cell division or stimulates or inhibits a biological response like motility or secretion of proteins. Growth factors are well known to those of skill in the art and include, but are not limited to, platelet-derived growth factor (PDGF), epidermal growth factor (EGF), insulin-like growth factor (IGF), transforming growth factor β (TGF-β), fibroblast growth factors (FGF), interleukin 2 (IL2), nerve growth factor (NGF), interleukin 3 (IL3), interleukin 4 (IL4), interleukin 1 (IL1), interleukin 6 (IL6), interleukin 7 (IL7), granulocyte/macrophage colony-stimulating factor (GM-CSF), granulocyte colony-stimulating factor (G-CSF), macrophage colony-stimulating factor (M-CSF), erythropoietin and the like. One of skill in the art recognizes that the term growth factor as used herein generally includes cytokines and colony stimulating factors.

Attachment of the Phytofluor to the Moiety

The proteinaceous portions of the fluorescent adducts (phytofluors) referred to here as the apoproteins provide a wide range of functional groups for conjugation to proteinaceous and non-proteinaceous molecules. Functional groups which are present include, but are not limited to amino, thio, hydroxyl, and carboxy. In some instances, it may be desirable to introduce, delete, or modify functional groups, particularly thio groups where the apoprotein is to be conjugated to another protein.

In certain embodiments it is also possible to bind the bilin component of the phytofluor to the moiety that is to be labeled.

Depending upon the nature of the molecule (e.g., member of a specific binding pair) to be conjugated to the phytofluor, the ratio of the two moieties will vary widely, where there may be a plurality of subject molecules to one phytofluor or apoprotein or, conversely, where there may be a plurality of phytofluors or apoproteins to one subject molecule. Of course, the molar ratio of the molecule (moiety) to be labeled to the phytofluor or apoprotein may be about 1:1. In addition, in some instances, initial intermediates are formed by covalently conjugating a small ligand to a fluorescent adduct and then forming a specific binding pair complex with the complementary receptor, where the receptor then serves as a ligand or receptor in a subsequent complex or is itself covalently attached to a ligand or receptor intended for use in a subsequent complex.

The procedure for attaching a subject molecule to the phytofluor or an apoprotein of the fluorescent adduct will vary according to the chemical structure of the agent. As indicated above, the apoproteins contain a variety of functional groups (e.g., —OH, —COOH, —SH, or —NH$_2$) groups, which are available for reaction with a suitable functional group on an agent molecule to bind the agent thereto. Alternatively, the apoprotein may be derivatized to expose or attach additional reactive functional groups. The derivatization may involve attachment of any of a number of linker molecules such as those available from Pierce Chemical Company, Rockford Ill. A bifunctional linker having one functional group reactive with a group on a particular agent, and another group reactive with an antibody, may be used to form the desired immunoconjugate.

Alternatively, derivatization may involve chemical treatment of the antibody; e.g., glycol cleavage of the sugar moiety of the glycoprotein antibody with periodate to generate free aldehyde groups. The free aldehyde groups on the antibody may be reacted with free amine or hydrazine groups on an agent to bind the agent thereto (see, e.g., U.S. Pat. No. 4,671, 958). Procedures for generation of free sulfhydryl groups on antibodies or antibody fragments are also known (see, e.g., U.S. Pat. No. 4,659,839). Many procedure and linker molecules for attachment of various compounds including radionuclide metal chelates, toxins and drugs to proteins (e.g., to antibodies) are known. See, for example, European Patent Application No. 188,256; U.S. Pat. Nos. 4,671,958, 4,659, 839, 4,414,148, 4,699,784; 4,680,338; 4,569,789; and 4,589, 071; and Borlinghaus et al. (1987) *Cancer Res.* 47: 4071-4075).

Linking agents suitable for joining the adducts of this invention to nucleic acids are also well known. For example, linking agents which are specific to the free secondary hydroxyl normally present at the 3' end include phosphites, succinic anhydride and phthalamide. Linking agents which are specific to the phosphate normally present on the sugar at the 5' end (at least for most naturally occurring polynucleotides or products of most cleavage reactions) include carbodiimides such as 1-ethyl-,3'dimethylamino propylcarbodiimide, with or without imidazole or 1-methylimidazole. See Chu et al. (1983) *Nucleic Acids Res.* 11: 6513-6529.

Vectors for Expression of Apoprotein Fusion Proteins.

A nucleic acid of the invention encoding a polypeptide fused to a mutant apoprotein, e.g., as described above, can be incorporated into a recombinant expression vector in a form suitable for expression in a host cell. The term "in a form suitable for expression of the fusion protein in a host cell" is intended to mean that the recombinant expression vector includes one or more regulatory sequences operably linked to the nucleic acid encoding the enzyme(s) in a manner that allows for transcription of the nucleic acid into mRNA and translation of the mRNA into the subject protein(s). The term "regulatory sequence" is art-recognized and intended to include promoters, and/or enhancers and/or other expression control elements (e.g., polyadenylation signals). Such regulatory sequences are known to those skilled in the art (see, e.g., Goeddel (1990) *Gene Expression Technology: Meth. Enzymol.* 185, Academic Press, San Diego, Calif.; Berger and Kimmel, *Guide to Molecular Cloning Techniques, Methods in Enzymology* 152 Academic Press, Inc., San Diego, Calif.; Sambrook et al. (1989) *Molecular Cloning—A Laboratory Manual* (2nd ed.) Vol. 1-3, Cold Spring Harbor Laboratory, Cold Spring Harbor Press, NY, etc.).

In certain embodiments, this invention provides expression vectors designed specifically for expressing a protein "tagged" (e.g., fused to) a mutant apoprotein as described herein. Such expression vectors typically comprise a nucleic acid sequence encoding the mutant apoprotein. In preferred embodiments, the vectors additionally comprise one or more cloning sites (e.g. restriction sites) for insertion of a nucleic acid encoding the a polypeptide that is to be tagged with the apoprotein.

In preferred embodiments, the cloning site is placed in the vector such that when a nucleic acid encoding a polypeptide is inserted in the cloning site the polypeptide and the apoprotein "tag" are in frame and expressed as a fusion protein. The mutant apoprotein tag can be directly joined to the amino or carboxyl terminus of the subject polypeptide, or joined to the polypeptide through a peptide linker.

The design of the expression vector can depend on such factors as the choice of the host cell to be transfected and/or particular protein(s) to be expressed. When used in mammalian cells, a recombinant expression vector's control functions are often provided by viral genetic material. Preferred promoters include, but are not limited to CMV immediate early, HSV thymidine kinase, early and late SV40, LTRs from retrovirus, and mouse metallothionein-I. Use of appropriate regulatory elements can allow for high level expression of the polypeptide(s) in a variety of host cells. A number of suitable expression systems are commercially and can be modified to produce the vectors of this invention. Illustrative expression systems include, but are not limited to baculovirus expression vectors (see, e.g., O'Reilly et al. (1992) *Baculovirus Expression Vectors: A Laboratory Manual*, Stockton Press) for expression in insect (e.g. SF9) cells, a wide variety of expression vectors for mammalian cells (see, e.g., pCMV-Script® Vector, pCMV-Tag1, from Stratagene), vectors for yeast (see, e.g, pYepSec1, Baldari et al. (1987) *EMBO J.* 6: 229-234, pMFa (Kurjan and Herskowitz, (1982) *Cell* 30: 933-943), pJRY88 (Schultz et al., (1987) *Gene* 54:113-123), pYES2 (Invitrogen Corporation, San Diego, Calif.), and the like), prokaryotic vectors (see, e.g, arabinose-regulated promoter (Invitrogen pBAD Vector), T7 Expression Systems (Novagen, Promega, Stratagene), Trc/Tac Promoter Systems (Clontech, Invitrogen, Kodak, Life Technologies, MBI Fermentas, New England BioLabs, Pharmacia Biotech, Promega), PL Promoters (Invitrogen pLEX and pTrxFus Vectors), Lambda PR Promoter (Pharmacia pRIT2T Vector), Phage T5 Promoter (QIAGEN), tetA Promoter (Biometra pASK75 Vector), and the like.

It will be appreciated that desired polypeptides can be operably linked to constitutive promoters for high level, continuous expression. Alternatively, inducible and/or tissue-specific promoters can be utilized.

In certain embodiments, the recombinant expression vector of the invention is a plasmid or cosmid. In other preferred embodiments, a recombinant expression vector of the invention can be a virus, or portion thereof, that allows for expression of a nucleic acid introduced into the viral nucleic acid. For example, replication defective retroviruses, adenoviruses and adeno-associated viruses can be used.

Kits.

In certain embodiments, this invention provides kits for the practice of the methods described herein. Certain kits will comprise a container containing a mutant apoprotein and/or a nucleic acid encoding the mutant apoprotein, and/or a vector for expressing a heterologous polypeptide in fusion with a mutant apoprotein, and/or a fluorescent adduct (phytofluor) as described herein. The kits can additionally and optionally further include a bilin and/or biliverdin for forming an adduct with the mutant apoprotein. In certain embodiments, the kits can optionally include filters for use in visualizing emission of the phytofluor.

The kits can, optionally, further include instructional materials teaching the use of the apoprotein adduct as a label that provides a fluorescent signal in the far red and/or near infrared portion of the spectrum. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Isolation and Characterization of a Red and Near Infrared Fluorescent Phytochrome RubyRed-1 050304

In this example, a directed evolution approach was undertaken with the goal of creating novel fluorescent phytochrome mutants. Error-prone PCR was employed to generate point mutations at random positions within Cph1. We hypothesized that mutations within the chromophore pocket that sterically inhibit chromophore photoisomerization will result in a greatly enhanced fluorescence quantum yield. Such mutants were predicted to yield R or NIR fluorescence. A mutant was identified with this screen and is described herein.

Methods.

Expression Strains and Constructs.

The cyanobacterial phytochrome 1 construct pBAD-Cph1 (N514) and the bilin biosynthetic plasmid pPL-PCB were previously described by Gambetta and Lagarias (Gambetta and Lagarias (2001) *Proc. Natl. Acad. Sci. USA*, 98(19): 10566-10571). These plasmids were routinely co-transformed into *E. coli* LMG194 (Invitrogen) cells and selected by growth on agar media containing 50 μg/ml of ampicillin and 25 μg/ml of kanamycin.

Error-Prone PCR Library Construction.

Random mutagenesis of Cph1(N514) was performed using the GeneMorph PCR Mutagenesis Kit (Stratagene). All mutagenesis reactions were carried out in a total volume of 50 μl and contained the following components: 1× Mutazyme reaction buffer, 800 μM dNTP mixture (200 μM each final), 62.5 ng of each primer, template DNA (varied), 2.5 U of Mutazyme DNA polymerase, and deionized H$_2$O (to 50 μl). The following amounts of template DNA (pBAD-Cph1 (N514) plasmid) were used to obtain different degrees of mutagenesis: 3.7 pg, 37 pg, 3.7 ng and 37 ng of DNA. PCR reaction conditions were set as follows: 95° C. 1 min.; 95° C. 1 min., 55° C. 1 min., 72° C. 2.5 min. (30-40 cycles); 72° C. 10 min. Cph1(N514) was amplified under these conditions using the sense primer NcoIFCph1P2, 5'-GGGCTAACAG-GAGGAATTA<u>CCATG</u>-3' (SEQ ID NO:5) and the antisense primer Cph1(N514)HindIII, 5'-GC<u>AAGCTT</u>GTTCTTCTGCCTGGCG-3' (SEQ ID NO:6) (restriction sites are underlined).

The 1.5 kbp PCR products, generated from the different mutagenesis reactions of the N-terminal 514 amino acid region of Cph1, were pooled and gel-purified using QiaQuick PCR columns (Qiagen). The purified PCR fragments were restricted with NcoI and HindIII and ligated with the gel-purified NcoI-HindIII fragment from pBAD-Cph1(N514). The resulting ligation mixtures were used to contruct libraries by transformation of electro-competent cells of *E. coli* strain LMG194. Libraries were maintained as isolated plasmid DNA.

Flow Cytometry Screening.

A Cytomation MoFlo high-speed cell sorting flow cytometer at the UC Davis Optical Biology Lab was used to screen for fluorescent phytochrome mutants expressed in *E. coli* cells. Fluoresence excitation was performed using a tunable argon/krypton mixed gas laser with the 647 nm laser line. A HQ660lp long-pass filter (CHROMA) was used to detect fluorescence at wavelengths longer than 660 nm. For screening, electro-competent cells of *E. coli* strain LMG194 containing the pPL-PCB plasmid were transformed with Cph1 (N514) mutant plasmid libraries. Transformants were selected by growth at 37° C. on RM/AK agar plates. Colonies that grew on the selection plate following overnight incubation at 37° C. were diluted into 3 ml of RM liquid media followed by dilution 1 to 500 in 2 ml of RM/AK. After overnight growth at 37° C., cultures were diluted 1 to 250 with 25 ml of RM/AK and grown to an OD 600 of 0.5. To induce Cph1(N514) expression, cultures were then diluted in half with LB/AK containing 2 mM IPTG and 0.008% L-arabinose and grown at 37° C. for 3 h in darkness with shaking at 250 RPM. Following this induction, a 1.5 ml aliquot was centrifuged 1,500×g for 2 min and the resulting cell pellet was gently washed three times with 1 ml of 0.25μ filtered PBS buffer (with centrifugation each time). The optical density at 600 nm (OD 600) was determined and the cells were diluted to a final concentration of 2×10$^8$ cells/ml (i.e. OD 600 of 0.8) using filtered PBS. The cell suspensions were then passed over a nylon filter fitted falcon tube to remove residual dust and debris prior to flow cytometry. For cell sorting, forward scatter was used to define events and a suitable window of forward-scatter and fluoresence to identify 'positives' was chosen empirically. Cells were sorted with the pressure differential set to 1.0 at a rate of approximately 5,000 events per second. Data was acquired using Summit software from Cytomation. Putative fluorescent mutant-containing cells were collected into a tube containing 0.5 ml of sterile liquid LB media, which were subsequently plated onto LB/AK media. Plasmid DNA from each AK-resistant colony was isolated and re-transformed electro-competent cells of *E. coli* strain LMG194. Plasmid DNA, isolated from ampicillum-resistant colonies, was characterized by nucleotide sequencing (Davis Sequencing Inc, Davis, Calif.) and used to transform electro-competent cells of *E. coli* strain LMG194 containing the pPL-PCB plasmid. The fluoresent mutant Cph1(N5145) phytochrome RR-1 was isolated as described.

Phytochrome Expression and Purification.

Competent cells of *E. coli* strain LMG194 (Invitrogen) and *E. coli* strain LMG194 containing plasmid pPL-PCB (LMG194:pPL-PCB) were transformed with sorted or purified pBAD-Cph1(N514) plasmid DNA using standard protocols. For in vivo assembled (holo)phytochromes, dual ampicillin- and kanamycin-resistant transformants of LMG194: pPL-PCB were cultured overnight at 37° C. in 2 ml of RM liquid media containing 50 μg/ml of ampicillin and 25 μg/ml of kanamycin (RM/AK). Following 1:250 dilution into 100 ml of RM/AK, cells were grown at 37° C. to an $OD_{580}$ of ≈0.5. The 100 ml cultures were then diluted with 900 ml of LB medium containing 50 μg/ml of ampicillin and 25 μg/ml of kanamycin (LB/AK). Isopropyl β-D-thiogalactoside (IPTG) was added to a final concentration of 0.5 mM to induce expression of the bilin biosynthetic operon. After incubation for 1 h at 37° C., L-arabinose was added to a final concentration of 0.002% (w/v) to induce the expression of the apophytochrome and to hyper-induce the bilin biosynthetic operon. Cell cultures were grown at 37° C. for 4 h, after which cells were collected by centrifugation and resuspended in 5 ml of extraction/wash (EW) buffer (50 mM Tris-HCl pH 7.0, 300 mM NaCl, 10% (v/v), 1 mM 2-mercaptoethanol, and 20 mM imidazole). Cell suspensions were passed through a French press twice at 10,000 psi to lyse the cells, and insoluble material was removed by ultracentrifugation at 75,000 rpm for 20 min (TLA100.2 rotor). Recombinant N514 phytochrome protein was then purified from the crude soluble protein extract using TALON spin columns that contain 0.5 ml bed volume of TALON-NX metal affinity resin (Clontech Laboratories). Crude soluble protein extracts were applied to TALON spin columns that had been pre-equilibrated with EW buffer. Following washing with EW buffer (2× column volume), bound protein was eluted with EW buffer containing 200 mM imidazole adjusted to pH 7.0. Prior to spectropotometric analysis, purified Cph1(N514) solutions were dialyzed overnight at 4° C. against 25 mM TES KOH pH 7.5 containing 10% (v/v) glycerol. Apophytochromes were isolated similarly except that kanamycin and IPTG were not included in the growth media. All expressions and purifications were carried out in the dark or under green light to reduce phytochrome photoconversion.

Absorption and Fluorescence Measurements.

All absorption spectra were obtained using an HP8453 ultraviolet-visible spectrophotometer. Phytochrome difference spectra were obtained as described previously (Li and Lagarias (1994) *Proc. Natl. Acad. Sci. USA*, 91(26): 12535-12539). Red light (650+/−5 nm) and far-red light (720±5 nm) used for difference spectroscopy had fluence rates of 150 μM $m^{-2}s^{-1}$. For comparative purposes, the in vivo assembled adducts were adjusted to an $A_{280}$ of 0.35 (0.33 mg/ml or 5.3 μM). The in vitro assembled adducts were adjusted to an A280 of 0.25 (0.24 mg/ml or 3.8 μM). Assembly experiments were performed by mixing 100 μl of purified apoprotein with 2 μl of 2 mM bilin in DMSO followed by incubation for 30 min at room temperature in the dark. These mixtures were adjusted to 500 μl using buffer alone prior to fluorescence measurements. Corrected fluorescence excitation and emission spectra were obtained with an SLM Aminco Bowman AB2 fluorimeter. Monochromators were adjusted to 4 nm bandpass for all fluorescence measurements on the AB2. For comparative purposes, fluorescence measurements shown on the same graphs were performed using samples adjusted to equal absorbance at 280 nm (0.4) and equal excitation voltages were used.

SDS-PAGE and Zinc-Blot Analysis.

Protein samples were analyzed by SDS-PAGE using the Laemmli buffer system (Laemmli (1970) *Nature*, 227: 680-685). After electrophoresis, proteins were electrophoretically transferred to polyvinylidene difluoride (PVDF) membranes at 100 V for 60 minutes. The PVDF membranes were incubated in 1.3 M zinc acetate overnight at 4° C., and the fluorescence was detected using a Storm 860 Fluorimager in red fluorescence mode (Li and Lagarias (1994) *Proc. Natl. Acad. Sci. USA*, 91(26): 12535-12539; Berkelman and Lagarias (1986) *Analytical Biochem.*, 156: 194-201).

Results & Discussion.

Error-prone PCR was used to generate random point mutations throughout the Cph1(N514) gene construct. In the error-prone PCR reaction, Mutazyme polymerase (Stratagene) was used because it has an inherently low polymerase fidelity. Based on the amount of target DNA amplified, the amount of template DNA, the number of amplification cycles, and the mutagenesis factor for Mutazyme polymerase, it is possible to mathematically estimate the mutation range that has been generated from a particular mutagenesis reaction. For this reason, we used multiple PCR reactions using different amounts of template DNA and different numbers of amplification cycles. Sequential mutagenesis reactions using mutated PCR products from a previous mutagenesis reaction as template for a second mutagenesis reaction were also performed. This was done in order to increase the mutation frequency. Equal amounts of PCR product from each of the mutagenesis reactions were used to construct the final library. Using the variables described above, it could be estimated that the library of mutants generated from this experiment contains 3-21 bp changes per kbp (i.e. 4-32 bp changes in the Cph1(N514) gene or 11 bp changes per gene on average).

Upon ligating the mutant PCR products with the expression vector, the mixture was transformed and 1,500 colonies were isolated. Based on the number of colonies found on the control vector alone ligation plate, we estimate that 70% of the 1,500 clones contain a mutant gene. Therefore this library contains about 1,050 different mutant clones.

Flow cytometry is a high-throughput technique for screening fluorescence from single particles. In our screen of the library described above, we were able to sort 4.3 million cells with a scan rate of about 6,500 events per second (390,000 evm). During the sorting, we set the machine to collect two different fluorescent populations based on intensity, R1 moderate intensity and R2 high intensity fluorescence. We identified 840 clones in the R1 gate, and 5 in the R2 gate. The R2 class of mutants were rescued by growth on an agar plate containing antibiotic selection. Following 24 hours of growth, 14 individual colonies were isolated. This increase in colony number from the expected 5 to 14 was probably a result of sorting the cells on enrich mode, which may result in the collection of non-fluorescent cells collected with the desired mutant. By analyzing the fluorescent and spectroscopic properties of protein from each of the 14 cell lines using small-scale expression batches, an intensely red fluorescent mutant that we call Rudy Red 1 (RR-1) was identified.

Plasmid DNA was isolated from this red fluorescent strain and sequenced. Nucleotide sequence analysis revealed that the mutant had three base pair changes which caused three amino acid changes (compare RR-1 and WT sequences in FIGS. 1 and 2). These correspond to changes in the P2 PAS domain (A47T) and two changes in the P3 GAF domain (Y176H and I252N) as depicted in FIG. 3.

Figure 5:
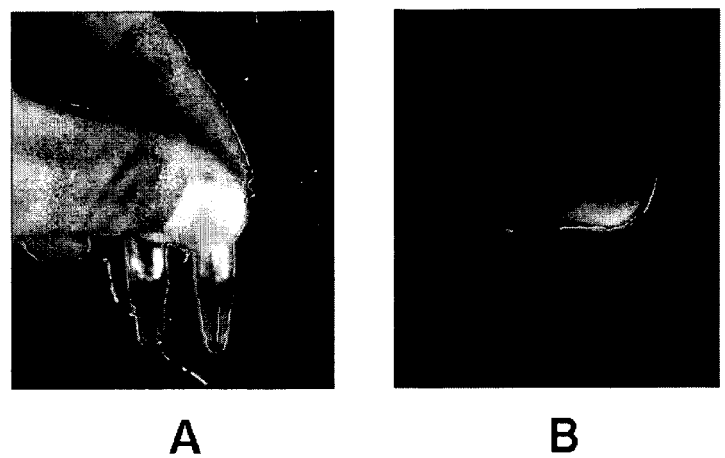
FIG. 5 shows color photographs of WT (right) and RR-1 (left) PCB adducts viewed under white light (panel A) or under UV light (Panel B).

To confirm that these mutations were responsible for the enhanced fluorescence of the original RR-1 isolate, the RR-1 plasmid DNA that was sequenced above was transformed back into new *E. coli* cells—one containing the bilin biosynthetic plasmid pPL-PCB (for holoprotein) and another lacking this plasmid (for apoprotein). The resulting strains were used to purify holo- and apo-protein for a detailed spectroscopic comparison with WT Cph1(N514). The mutant protein was expressed to levels comparable to that of wild-type (data not shown). Purified RR-1 mutant and wild-type apo- and holo-protein preparations were analyzed by SDS PAGE which showed that all four proteins were 60 kDa in mass as expected (FIG. 4, panel A). Zinc blot analysis revealed that the in vivo assembled holoproteins possessed a covalently attached bilin chromophore (FIG. 4, panel B, compare lanes 4 and 5 from the left) which the apoproteins lacked (FIG. 4, panel B, compare lanes 2 and 3 from the left). As shown in FIG. 5, the wild-type and mutant holoproteins can be distinguished both by their color and by the intense red fluorescence of RR-1 not seen in WT when viewed under UV irradiation.

Figure 6:
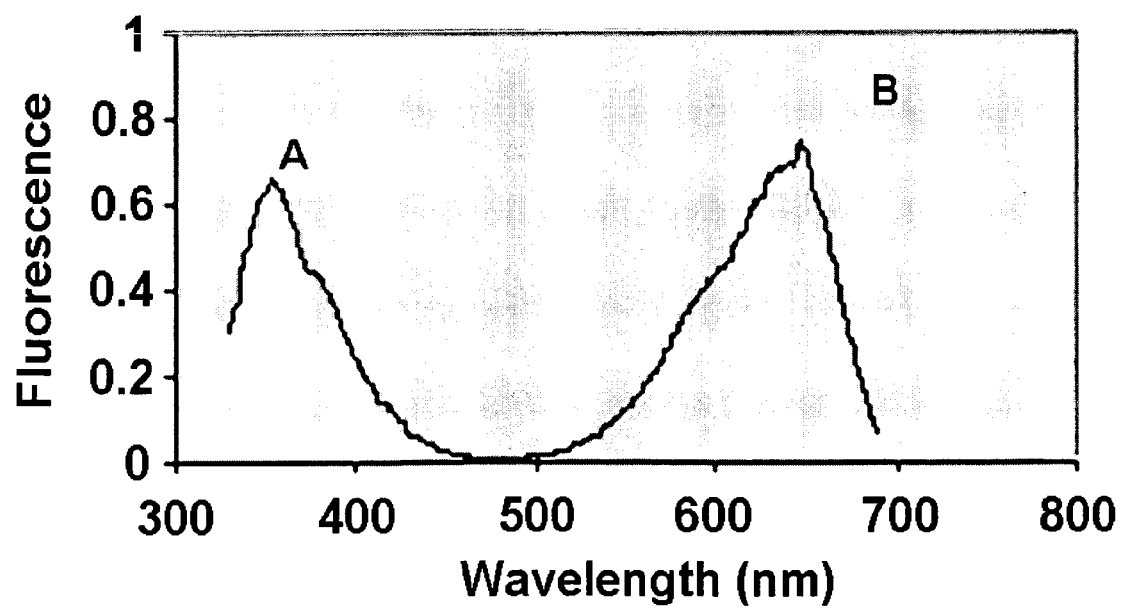
FIG. 6 shows fluorescence excitation (A) and emission (B) spectrum of RR-1 (PCB adduct).

Purified RR-1 and WT Cph1(N514) holoproteins were adjusted to the same protein concentration (i.e. $A_{280}$ value) to facilitate direct comparison of their spectroscopic properties. As shown in FIG. 6, the fluorescence spectrum of the RR-1 mutant revealed excitation peaks at 356 and 648 nm with an emission peak at 672 nm. Although WT possessed a similar fluorescence spectrum, RR-1's was more than 100-fold greater than observed for WT (FIG. 6). Taken together, these results indicate that the three mutations are responsible for the enhanced fluorescence quantum yield of the Cph1(N514) phytochrome mutant, RR-1.

Figure 7:
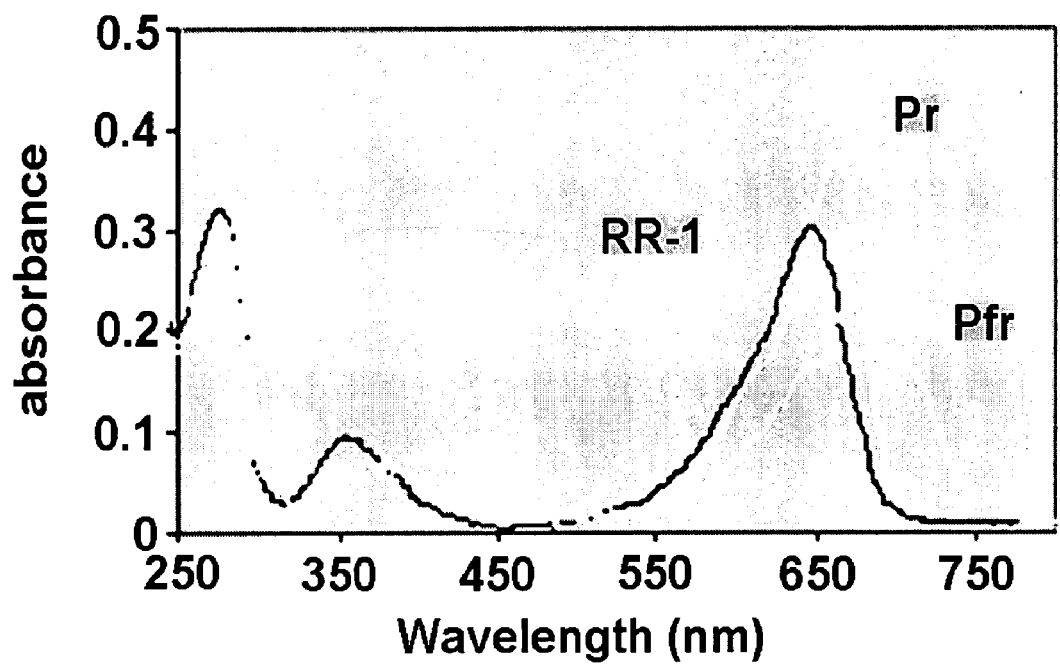
FIG. 7 shows absorption spectra of PCB adducts of RR-1 (black) and WT Cph1(N514) after saturating FR (Pr) or R (Pfr) irradiation (yellow).
Figure 8:
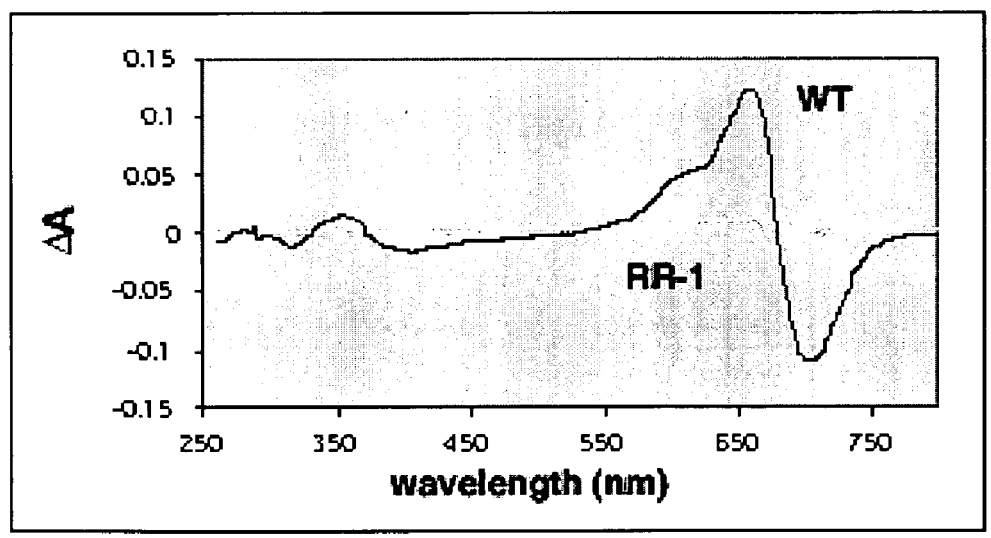
FIG. 8 shows phytochrome red minus far-red difference spectra of PCB adducts of RR-1 (yellow) and WT Cph1 (N514) (black).

FIG. 7 shows that the absorption spectrum of the RR-1 mutant is markedly blue-shifted by comparison with wild-type—with absorption maxima at 648 nm and 663, respectively (Table 1). The similar ratio of the near UV to red absorption maxima of RR-1 and WT, i.e. 0.36 and 0.27 respectively, further indicates that the conformation of their bilin chromophores are both similar. Since this comparison was performed at the same protein concentration, we conclude that the molar absorptivity of RR-1 at its absorption maximum is similar to that of WT. By comparison with WT, RR-1 also shows very little R/FR photoconversion under R or FR light, i.e. less than 5% of WT (FIG. 8). In contrast with the fluorescence spectra however, the difference spectrum of the RR-1 mutant was shifted to the blue in both Pr and Pfr forms compared to wild-type. These results indicate that the three mutations in RR-1 reduce the rate of photoisomerization which is likely responsible for its enhanced fluorescence yield.

TABLE 1

Absorbance Properties of RubyRed-1 and Cph1(N514)

| Adduct | Absorbance λmax (Pr) | Difference Spec. A. λmax/λmin | ΔΔA/A280 [ ] % conversion | UV: Red Ratio (Pr) |
|---|---|---|---|---|
| Cph1(N514)-PCB (in vivo assembly) | 663 | 659/804 (45 nm) | 322 ug/ml 330 ug/ml 98% | (364/663) 0.27 |
| RR-1-PCB (in vivo assembly) | 647 | 645/691 (46 nm) | 18 ug/ml 350 ug/ml 5% | (354/647) 0.36 |

Figure 9:
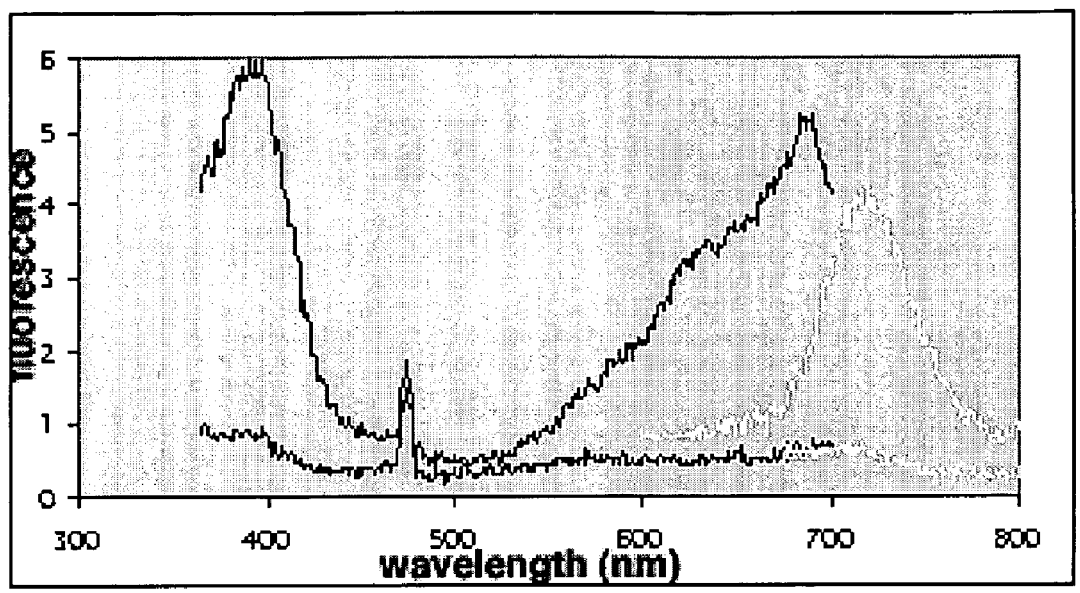
FIG. 9 shows fluorescence excitation (black) and emission (yellow) spectrum of RR-1 (PΦB adduct) prepared by in vitro incubation of apoproteins with PΦB.

In vitro biliprotein assembly studies were also performed by co-incubation of the bilin precursors phycocyanobilin (PCB) or phytochromobilin (PΦB) to purified apo-RR-1. The PCB studies confirm the results of in vivo co-expression of apoRR-1 with a PCB biosynthetic operon, indicating that the in vitro PCB-adduct of RR-1 has a fluorescence excitation and emission spectrum that is identical with that of the in vivo adduct (data not shown). As expected, PΦB assembly studies revealed a marked red-shift of the fluorescence spectrum of the PΦB-adduct of RR-1 which exhibits a fluorescence emission maximum that is shifted into the NIR (FIG. 9). Table 2 compares the fluorescence properties of PCB and PΦB adducts of RR-1 with those of the phytofluor, Cph1(N514)-PEB, recombinant c-phycocyanin alpha subunit (rCpcA) and the fluorescent protein dsRed.

TABLE 2

Fluorescence Properties of Red Fluorescent Proteins

| Adduct | Excitation λmax (nm) | Emission λmax (nm) | Stokes Shift (nm) | Date/Author |
|---|---|---|---|---|
| Cph1(N514)-PEB (in vitro assembled) | 580 | 590 | 10 | Lagarias (1997) Curr. Biol., 7(11) 870-876 |
| Ds Red (mRFP1 variant) | 584 | 607 | 23 | Campbell et al. (2002) PNAS, 99(12) 7877-7882 |
| Recombinant Cpc-A (rCpc-A) | 369/625 | 641 | 16 | Tooley & Glazer PNAS 2001, 98(19) 10560-10565 |
| Ruby Red-PCB (in vivo assembled) | 356/648 | 672 | 24 | AJF (2004) |
| Ruby Red-PΦB (in vitro assembled) | 393/684 | 717 | 33 | AJF (2004) |

In summary, molecular engineering of phytochromes has yielded the first far red and NIR-emitting, genetically encoded fluorescent biliprotein.

Example 2

Mutation of Phytochromes to Produce Fluorescent Molecules

In this example, directed evolution of a cyanobacterial phytochrome was undertaken to elucidate the structural basis of its light sensory activity by remodeling the chemical environment of its linear tetrapyrrole prosthetic group. In addition to identifying a small region of the apoprotein critical for maintaining phytochrome's native spectroscopic properties, our studies revealed a tyrosine-tohistidine mutation that transformed phytochrome into an intensely red fluorescent biliprotein. This tyrosine is conserved in all members of the phytochrome superfamily, implicating an essential role in light signaling. Since they are self-assembling biliproteins that can be generated in living cells, fluorescent phytochromes also hold great promise to expand the present repertoire of genetically encoded fluorescent proteins into the near infrared.

Background

Figure 10A:
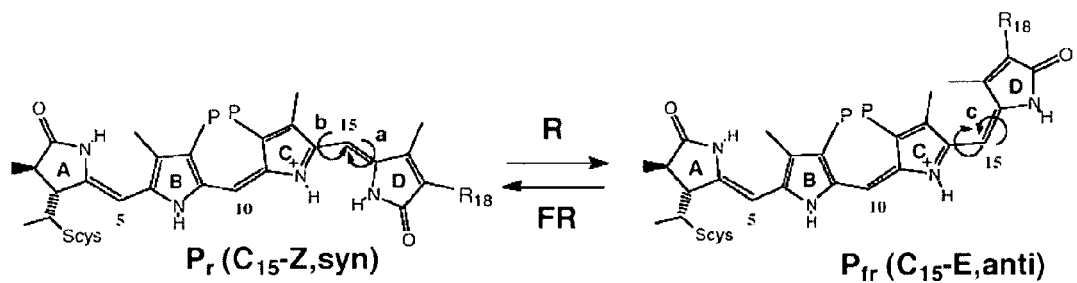
FIGS. 10A through 10C illustrate the structure of the phytochrome chromophore and domain arrangement of the Cyanobacterial phytochrome Cph1 and Cph1 used for mutagenesis.

The spectroscopic and photophysical properties of linear tetrapyrroles (bilins) are profoundly influenced by their chemical environment (1). In aqueous solution, bilins adopt cyclic porphyrinlike conformations, which strongly absorb in the near ultraviolet. Upon association with proteins such as the phycobiliprotein antennae of blue-green, red and cryptomonad algae (2) or the phytochrome photoreceptors of plants and cyanobacteria (3), bilins assume more extended conformations which significantly increases their visible light absorption and alters the pathways of light de-excitation. Adapted for efficient transfer of excitation energy to membrane-bound photosynthetic reaction centers, phycobiliproteins are intensely fluorescent proteins (4). By contrast, phytochromes are poorly fluorescent biliproteins due to the reversible photointerconversion between red (R) and far-red (FR) light absorbing forms, Pr and Pfr. This weak fluorescence reflects the efficient Z-to-E isomerization of the C15 double bond of phytochrome's bilin prosthetic group that occurs in the picosecond time scale (FIG. 10A) (5, 6). Despite extensive biochemical and spectroscopic characterization, the structural basis of phytochrome photoactivation remains poorly understood. To address this question, we have exploited the technique of directed evolution to identify mutations that either alter phytochrome's absorption spectra and/or enhance its fluorescence emission.

Figure 10B:
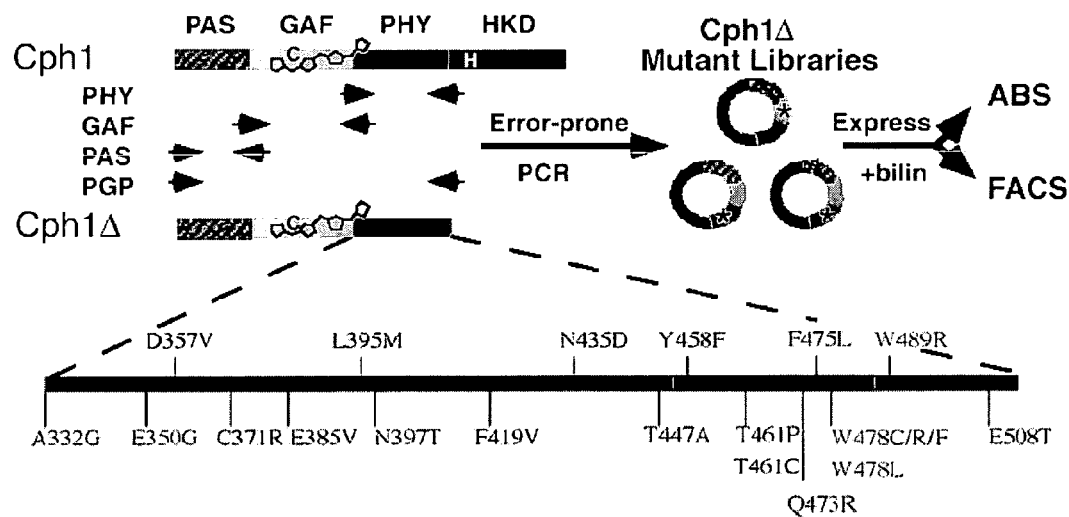
Figure 13:
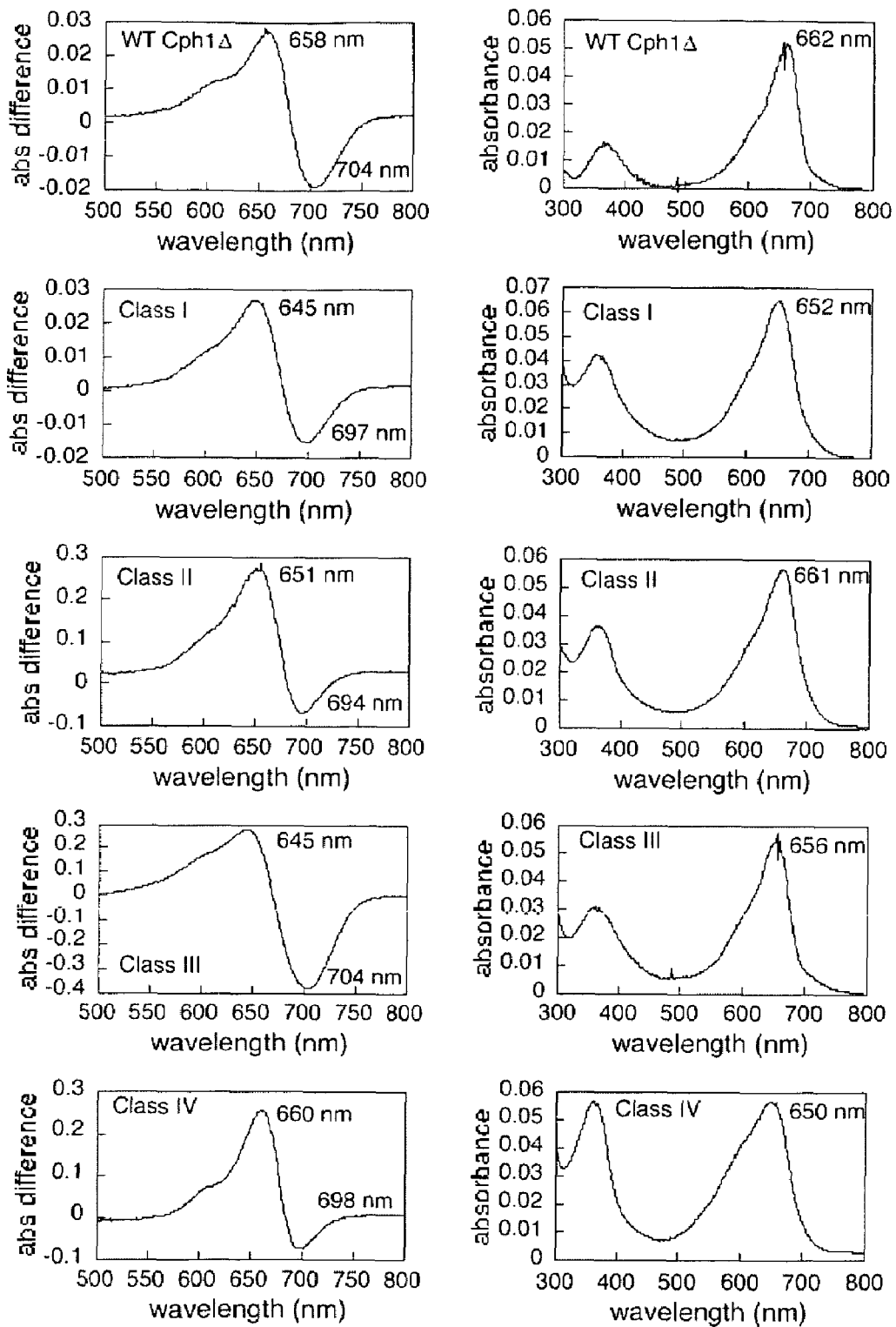
FIG. 13 shows spectroscopic properties of representative PHY domain mutants, from the four different phenotypic classes compared with WT Cph1. The left hand column shows the absorbance difference spectra and the respective $\lambda_{max}$ and $\lambda_{min}$ of WT and Mutant Classes I-IV. The right hand column shows the respective Pr absorption spectra.
Figure 15:
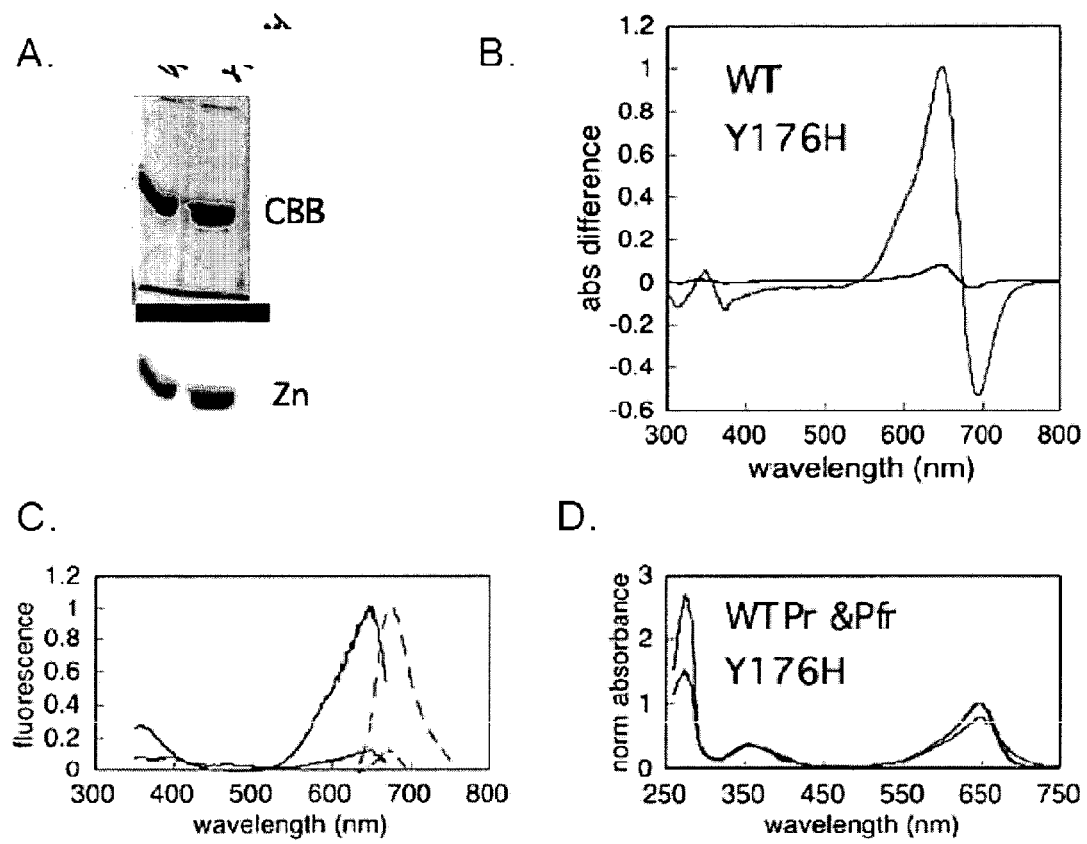
FIG. 15. Recombinant Cph1 P2P3 Domain WT and Y176H Mutant. Panel A: Coomassie Blue stained (top) and zinc-blot (bottom) 7.5% SDS polyacrylamide gel analysis of purified WT and Y176H mutant Cph1_P2P3 his. Both protein migrate at 42 kDa. Panel B: Normalized phytochrome difference spectrum of purified WT (Amax=648 nm/Amin=694 nm; red) and Y176H mutant (Amax=644 nm/Amin=689 nm; blue) Cph1_P2P3 his. Panel C: Normalized fluorescence excitation (solid) and emission (dashed) spectra of purified Y176H Cph1_P2P3his (EX 647 nm:blue/EM 674 nm:red) and WT Cph1_P2P3his (EX 649 nm:green/EM 672 nm: purple). Panel D: Normalized absorption spectra of WT Pr (max=358/650 nm; red) and Pfr (green) forms and the Pr form of Y176H mutant (Pr max=355/646 nm; red) blue) Cph1_P2P3 his.

The hallmark of the phytochrome superfamily is a photosensory 'input' domain, minimally consisting of a GAF-PHY subdomain pair that is often associated with a histidine kinase 'output' module (FIG. 10B)(7, 8). The bilin chromophores of plant (Phy) and cyanobacterial (Cph1 and Cph2) phytochromes are all covalently attached to an invariant cysteine residue within the conserved GAF 'bilin lyase' subdomain (9). Unlike phycobiliprotein assembly which requires bilin lyase enzymes to catalyze holoprotein assembly (10), bilin attachment to apophytochromes occurs autocatalytically (11). Phytochromes can therefore be produced in apophytochrome-expressing cells treated with exogenous bilins (12-14) as well as in cells engineered to biosynthesize bilins from endogenous heme (15, 16). The truncated Cph1 monomer (Cph1) was chosen for mutagenesis since it retained the ability to bind the native chromophore precursor phycocyanobilin (PCB) and yield a spectroscopically native holophytochrome (FIG. 10B) (15). Since the PHY domain stabilizes both the extended configuration of the bilin prosthetic group and the FR absorbing form of the phytochrome photoreceptor (9), we initially analyzed a Cph1 library in which the PHY domain was mutagenized by error-prone PCR (17). A subpopulation of this library, i.e. 91 clones, was characterized by DNA sequencing. Three Cph1 clones containing amino acid substitutions (58 total) were expressed, assembled with bilin and purified as holoproteins for spectrophotometric analyses (17). Many of these mutants possessed Cph1 wild type (WT) spectra (25 total) despite multiple mutations; those with altered spectra (33 total) fell into four phenotypic classes—none of them fluorescent (FIG. 13). Class I mutants, the largest class representing 51% of the mutants identified, exhibited 8-12 nm blue shifts in both the Pr and Pfr absorption maxima. Class II mutants, 24% of the total identified, displayed spectral shifts similar to Class I, with the exception of a significant reduction in the amount of Pfr formed at photoequilibrium—a phenotype that was quite similar to a Cph2 which lacked the PHY domain entirely (9). The final two classes displayed blue shifted Pr, i.e. Class III (12%), or blue-shifted Pfr, i.e. Class IV (12%), absorption maxima and increased non-photochemical dark reversion of Pfr to Pr.

Figure 10C:
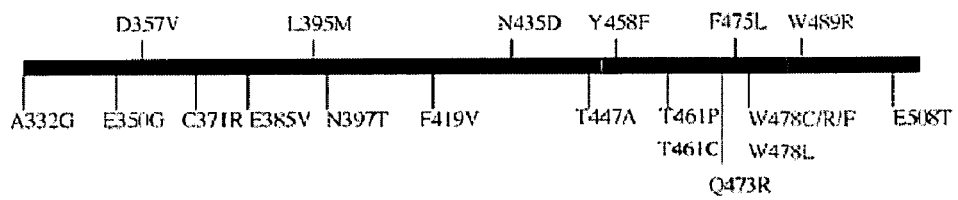

Since most of the spectrally altered Cph1 mutants contained multiple amino acid changes (FIG. 14), individual point mutations were introduced into WT to ascribe the spectral shifts to specific amino acid substitutions (17). This process was simplified by the observation that many of the same residues mutated in other Cph1 mutant clones had no effect on the spectrum (see FIG. 14). With this guiding principle, single mutants responsible for the observed spectral changes were identified following their re-introduction into a WT template. These analyses revealed that the spectrally altering mutations clustered in a small region of the PHY domain of Cph1, between residues 440 and 490 (FIG. 10C). This region of Cph1 is of particular interest since it corresponds to a sequence similar to the HisG family of ATP phosphoribosyltransferases that is inserted into the GAF-related PHY domains of all known phytochromes (7). A number of mutations that alter plant phytochrome function also fall in this region, i.e. phyA-112 (18), phyB-401 and phyB-GFP-4 (19, 20). These results implicate a key role for the HisG insert in phytochrome signaling, e.g. the stabilization of the active Pfr state of the photoreceptor. Saturation mutagenesis of this region should prove useful in understanding how the biochemical role of this region relates to the basic structure and function of phytochromes.

While the absorbance screen demonstrates the power of directed evolution to identify a key region of the PHY domain critical to phytochrome's photosensory activity, fluorescent mutants were not obtained from this PHY mutant library. This suggested that such gain-of-function mutations might be rare, requiring multiple amino acid changes throughout the entire photosensory domain. For this reason, we constructed new mutant libraries encompassing all three photosensory subdomains of Cph1 and exploited the higher throughput screening method of fluorescence activated cell sorting (FACS). Utilizing a bacterial cell line engineered to express genes encoding two enzymes for the conversion of endogenous heme to PCB (15), we introduced four Cph1 mutant libraries on a second plasmid with mutations in the PAS, GAF and/or PHY domains (FIG. 10B) (17). Following in vivo assembly of holoCph1, fluorescent mutants were selected by FACS using a red (647 nm) laser as an excitation source (17). A total of $4.9 \times 10^7$ cells were sorted from the four Cph1 mutant libraries (FIG. 10B), from which we isolated 18 red fluorescent mutant cell lines.

Figure 11A:
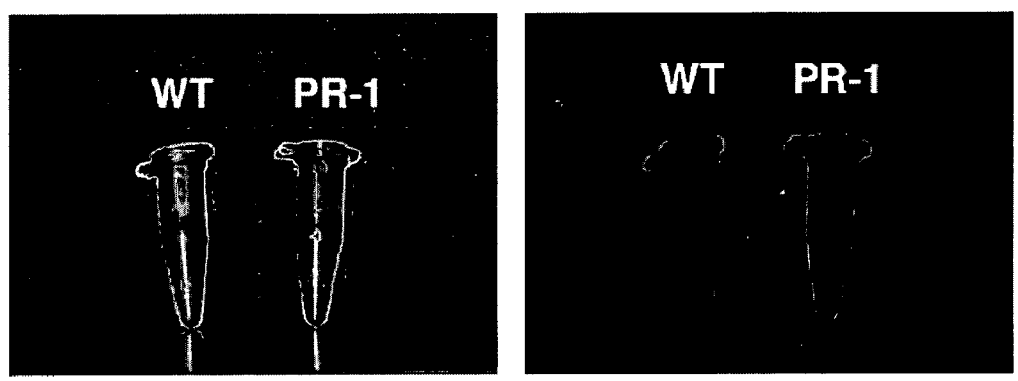
FIGS. 11A through 11D illustrate properties of the red fluorescent phytochrome mutant PR-1.
Figure 11B:
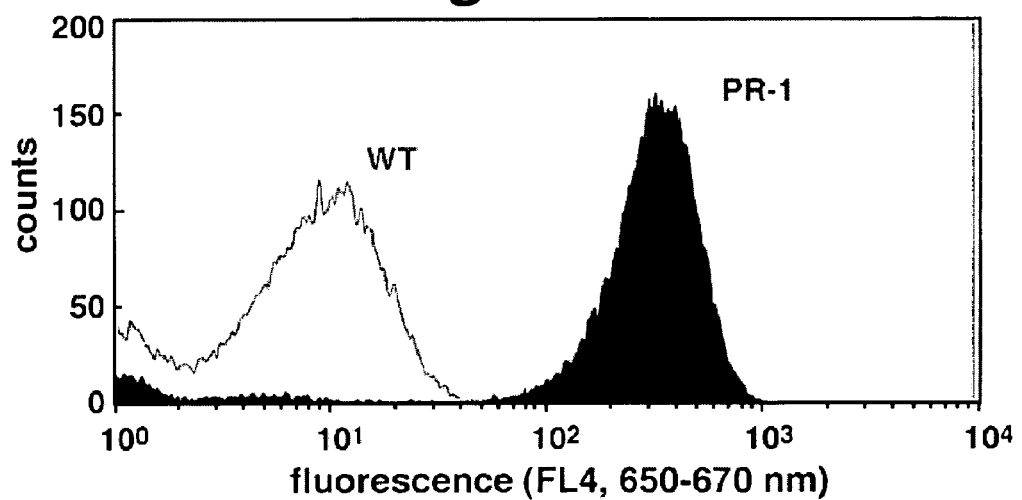
Figure 11C:
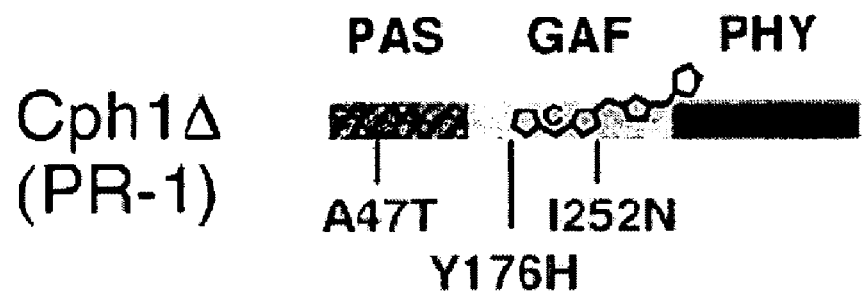

Five of these cell lines produced holophytochrome judging from their deep blue color and one of these lines was strongly fluorescent, that we name Phytofluor Red-1 (PR-1) using the nomenclature proposed in an earlier study (21) (FIG. 11A). Comparative flow cytometry showed that PR-1 expressing cells are well resolved from the WT parental cell line (FIG. 11B), thereby confirming the validity of the FACS screen (17). Plasmid DNA isolated from PR-1 expressing cells revealed three base pair mutations which resulted in three amino acid changes, i.e. A47T, Y176H, and I252N (FIG. 11C) (17). To determine whether all three mutations were necessary for PR-1's red fluorescence, all single mutants and double mutant combinations were constructed by site-directed mutagenesis and their corresponding holoproteins were produced in PCB-producing bacterial cell lines (17).

Figure 11D:
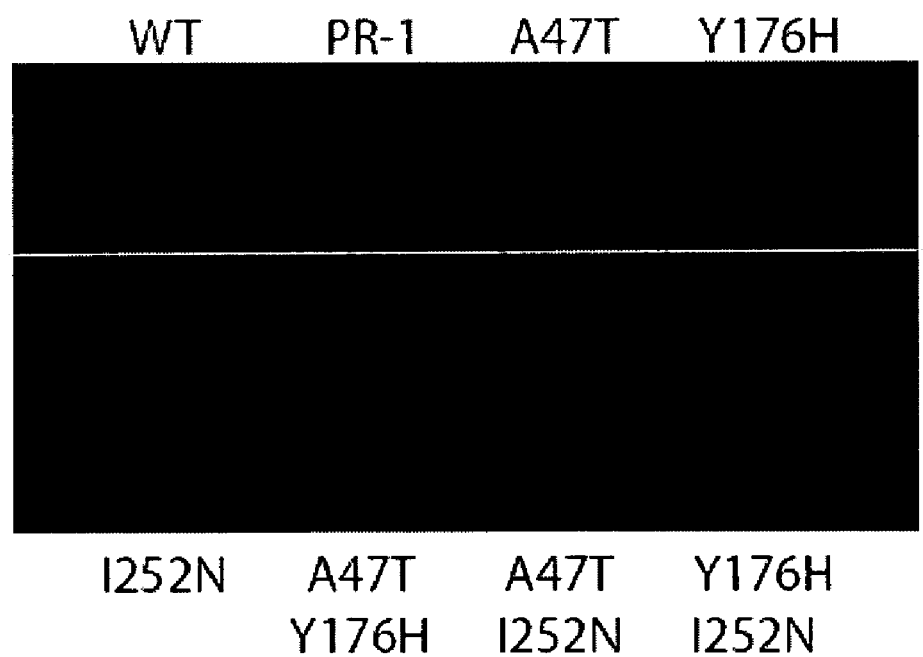

Fluorescence colony imaging revealed that the Y176H mutation was both necessary and sufficient for the enhanced red fluorescence of PR-1 since all mutants lacking this mutation were nonfluorescent (FIG. 11D) (17). Optical measurements showed that the non-fluorescent mutant cell lines possessed photoactive holophytochrome, indicating that their non-fluorescence did not reflect the lack of expression and/or bilin attachment (22). Taken together, these results showed that the single Y176H mutation was sufficient to convert WT into an intensely red fluorescent biliprotein.

Figure 12A:
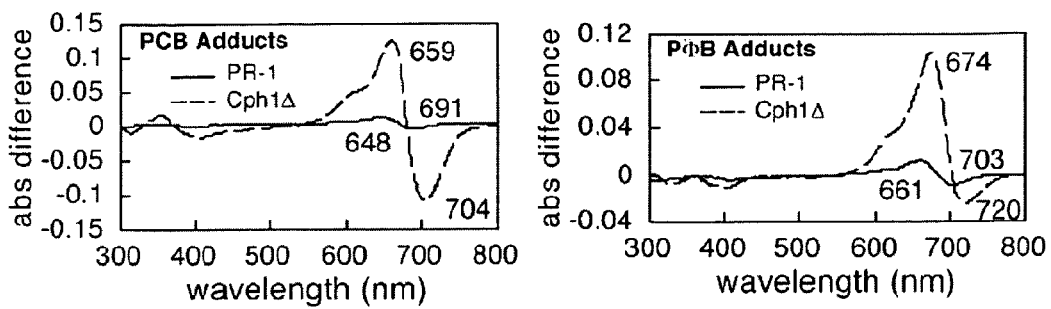
FIGS. 12A through 12C illustrate spectroscopic and fluorescence properties of PCB and PB bilin adducts of Cph1 and PR-1.
Figure 12B:
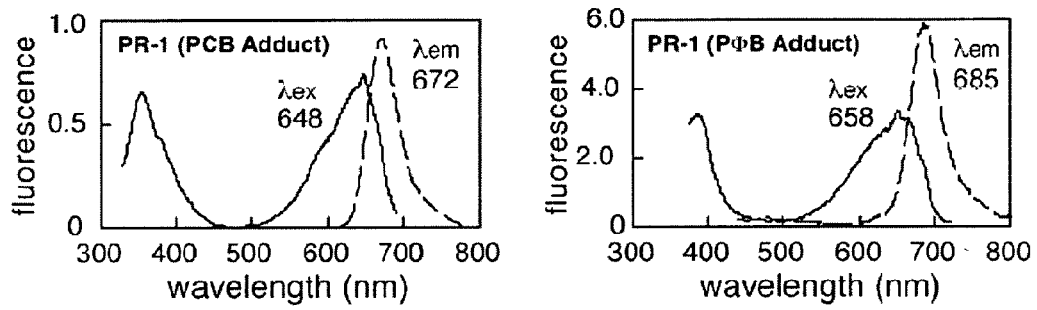
Figure 12C:
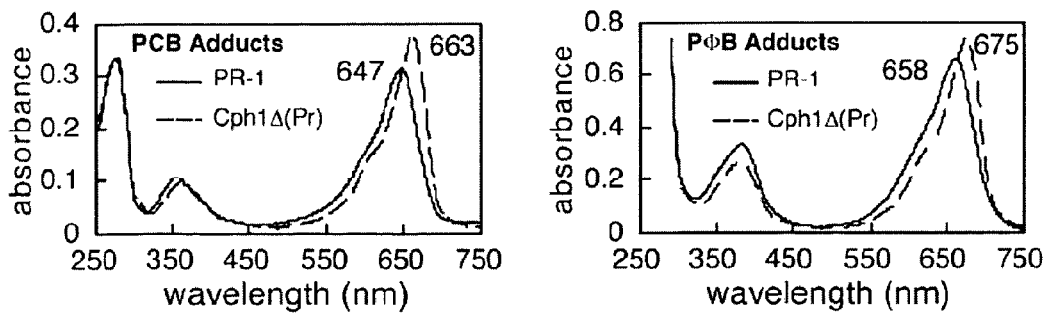

PR-1, affinity-purified as either the PCB- or the plant phytochrome chromophore precursor phytochromobilin (PB)-adduct (17), was shown to be poorly photoactive with a phytochrome difference spectrum that is considerably less than WT (FIG. 12A). The decreased photoconversion efficiency of PR-1 correlates with its enhanced fluorescence emission at 672 and 685 nm for the respective PCB and PB adducts (FIG. 12B) (17). The absorption spectra of PCB- and PBadducts of PR-1 are qualitatively similar to those of the Pr form of WT except that their long wavelength absorption maxima are slightly blue-shifted and broadened (FIG. 12C) (17). We estimate the molar absorption coefficient of the PCB adduct of PR-1 at 648 nm to be 85,000 $M^{-1}cm^{-1}$ which is slightly smaller than that of WT (23). SDS PAGE and zinc-blot analyses (24) also confirm that the PCB-derived chromophore of PR-1 is covalently attached to the mutant apoprotein (22). Taken together, these results indicate that the structure, conformation and protonation state of the bilin prosthetic groups of WT and PR-1 are qualitatively similar.

The discovery that a single Y176H amino acid substitution can transform a phytochrome into a redemitting phytofluor is of significance for a number of reasons. This result implicates a critical role for this tyrosine in the primary Z-to-E photoisomerization reaction of phytochrome's bilin prosthetic group since it is conserved in GAF domains of all known phytochromes (9). We can only speculate whether this tyrosine plays a direct or indirect role in phytochrome's bilin prosthetic group photochemistry since no phytochrome structure has been solved by x-ray crystallography. Introduction of the corresponding Y176H mutation into other phytochromes, including members of the bacteriophytochrome family of biliverdin binding proteins (8, 25), should shed light on the role that this conserved tyrosine residue plays in the photoactivation pathway of the extended phytochrome family in general. While our results show that photoconversion is greatly reduced in PR-1, it is not completely eliminated by the tyrosine-to-histidine mutation. This latent photochemistry suggests that phytochromes with the corresponding Y176H mutation may retain their ability to regulate plant photomorphogenesis at the same time they can visualized by fluorescence in situ. With additional rounds of mutagenesis on PR-1, phytofluors with emission extending into the infrared may ultimately be engineered. The ability of yeast and plants to incorporate PCB into apophytochromes (12-14) suggests that any genetically encoded protein of interest can potentially be tagged with a PR-1 derived phytofluor for visualization in living cells using techniques well established for members of the green fluorescent protein family (26, 27).

Materials and Methods.

Construction of the Initial PHY Subdomain Mutant Library.

An error-prone PCR library of the PHY subdomain was generated using the Diversify PCR Random Mutagenesis Kit (CLONTECH), the pBAD-Cph1 plasmid template (15) and sense primer 5'-CTT CGA TTA CCG GGT GCA GCT G-3' (SEQ ID NO:7) and antisense primer 5'-GCA AGC TTG TTC TTC TGC CTG GCG-3' (SEQ ID NO:8). Six variations in MnSO4 and dGTP final concentrations were used: 0 and 40 µM, 320 and 40 µM, 480 and 40 µM, 640 and 80 µM, 640 and 120 µM, and 640 and 200 µM, respectively. PCR products from all six mutagenesis reactions were pooled and purified using QiaQuick PCR columns (Qiagen). After restriction with PvuII and HindIII, the purified fragments were ligated with the PvuII- and HindIII-restricted pBAD-Cph1 plasmid from which the PHY domain had been removed. A library of approximately 2000 clones was generated.

Construction of PAS, GAF and PHY Subdomain and PGP Mutant Libraries.

The GeneMorph PCR Mutagenesis Kit (Stratagene) was used to generate four new Cph1 mutant libraries comprising individual PAS, GAF or PHY subdomains or all three together, i.e. the PGP library. The following variations in template DNA amount were used: 1 pg, 10 pg, 100 pg and 2 ng. PCR reaction cycling conditions were 95° C. 1 min.; 95° C. 1 min., 55° C. 1 min., 72° C. 2.5 min. (30-40 cycles); 72° C. 10 min. The PAS subdomain was amplified using sense primer 5'GGG CTA ACA GGA GGA ATT AAC CAT G-3' (SEQ ID NO:9) and antisense primer 5'CGG AAG TGT AGG CTG GCT CG-3' (SEQ ID NO:10). The GAF domain was amplified using the sense primer 5'GAC GGT TTA TGG TAT GTG AAC TCG-3' (SEQ ID NO:11) and the antisense primer 5'CAA TAA AAC CGC TTC ATG CTC CGC CAG-3' (SEQ ID NO:12). The PHY domain was amplified with the primers described above. The PGP library was constructed by amplifying the entire Cph1 gene using the PAS domain sense primer and the PHY domain antisense primer. The PCR products generated from the different mutagenesis reactions were gel-purified using QiaQuick PCR columns (Qiagen) and restricted with the appropriate restriction endonucleases followed by ligation with the gelpurified pBAD-Cph1 fragment digested in the same way. The estimated number of clones per library is as follows: PAS 7,500, GAF 1,000, PHY#2 6,000, and PGP 4,500.

Recombinant Protein Expression, Purification and Spectroscopic Analysis.

Mutants were expressed and purified as described previously (15). All absorption spectra were obtained using an HP8453 ultraviolet-visible spectrophotometer. Red light (650±5 nm) and far-red light (720±5 nm) used for difference spectroscopy had fluence rates of 150 $\mu M^{m-2}s^{-1}$. Corrected fluorescence excitation and emission spectra were obtained with an SLM Aminco Bowman AB2 fluorimeter with the monochromators adjusted to 4 nm bandpass.

Flow Cytometry.

A Cytomation MoFlo high-speed cell sorting flow cytometer at the UC Davis Optical Biology Lab was used to screen for fluorescence from phytochrome mutants expressed in *E. coli* cells. Fluorescence excitation was performed using a tunable argon/krypton mixed gas laser with the 647 nm laser line. A HQ660lp long-pass filter (CHROMA) was used to detect fluorescence at wavelengths longer than 660 nm. Small-scale holophytochrome expressions of the mutant libraries were carried out as described previously (15). Following induction, a 1.5 ml aliquot was centrifuged 1,500×g for 2 min and the resulting cell pellet was gently washed three times with 1 ml of 0.25µ filtered PBS buffer. The cells were diluted to a final concentration of $2 \times 10^8$ cells/ml (i.e. OD 600 of 0.8) using filtered PBS. The cell suspensions were then passed over a nylon filter fitted falcon tube to remove residual dust and debris prior to flow cytometry. For cell sorting, forward scatter was used to define events and a suitable window of forward-scatter and fluorescence to identify 'positives' was chosen empirically. Cells were sorted with the pressure differential set to 1.0 at a rate of approximately 5,000 events per second. Data was acquired using Summit software from Cytomation. For a direct comparison of the fluorescence properties of Cph1 and PR-1 expressed as PCB adducts in *E. coli*, the Becton Dickinson FACSCalibur flow cytometer was used with the 635 nm red diode laser and FL4 APC emission window (650-670 nm).

Site Directed Mutagenesis.

The QuickChange Site-Directed Mutagenesis kit (STRATAGENE) was used to generate site specific mutations in Cph1. Primers were designed based on the kit specifications. The mutagenesis reactions were carried out using 10 ng of dsDNA template. Mutants were sequenced for verification purposes.

Colony Fluorimaging.

Small-scale holophytochrome expressions of either WT, PR-1, or one of the single or double mutants, were grown as described previously (15). The cultures were then diluted 1:100 and 15 µl of this dilution was spotted onto a sterile polyester 0.2µ, 47 mm membrane (OSMONICS INC.) which was placed on top of a selective RM plate. The membranes were incubated overnight at 30° C. and were subsequently transferred to induction plates (RM ampicillin, kanamcyin, 1 mM IPTG, and 0.004% w/v L-arabinose). The membranes were incubated overnight at 30° C. and then at 37° C. for 5 hours. The membranes were transferred to 1% agarose/PBS plates for imaging. Photographs were taken under ultraviolet light (365 nm) using a Tiffen 67 mm yellow 12 UV-cutoff filter.

REFERENCES AND NOTES

1. H. Falk, The Chemistry of Linear Oligopyrroles and Bile Pigments. (Springer-Verlag, Vienna, 1989).
2. A. N. Glazer, *Methods Enzymol* 167, 291-303 (1988).
3. H. Smith, *Nature* 407, 585-591 (2000).
4. A. N. Glazer, *J. Appl. Phycol.* 6, 105-112 (1994).
5. A. R. Holzwarth, J. Wendler, B. P. Ruzsicska, S. E. Braslavsky, K. Schaffner, *Biochim. Biophys. Acta* 791, 265-273. (1984).
6. M. Bischoff, G. Hermann, S. Rentsch, D. Strehlow, *Biochem.* 40, 181-186 (2001).
7. B. L. Montgomery, J. C. Lagarias, *Trends in Plant Science* 7, 357-366 (2002).
8. R. D. Vierstra, S. J. Davis, *Sem. Cell Dev. Biol.* 11, 511-521 (2000).
9. S. H. Wu, J. C. Lagarias, *Biochem.* 39, 13487-13495 (2000).
10. W. M. Schluchter, A. N. Glazer, in *The Photosynthetic Prokaryotes*. G. A. Peschek, W. Loffelhardt, G. Schmetterer, Eds. (Kluwer Academic/Plenum Press, New York, 1999) pp. 83-95.
11. J. C. Lagarias, D. M. Lagarias, *Proc. Natl. Acad. Sci. USA* 86, 5778-5780. (1989).
12. L. Li, J. C. Lagarias, *Proc. Natl. Acad. Sci. USA* 91, 12535-12539 (1994).
13. T. Kunkel, V. Speth, C. Buche, E. Schafer, *J. Biol. Chem.* 270, 20193-20200 (1995).
14. S. Shimizu-Sato, E. Huq, J. M. Tepperman, P. H. Quail, *Nature Biotechnology* 20, 10411044 (2002).
15. G. A. Gambetta, J. C. Lagarias, *Proc. Natl. Acad. Sci. USA* 98, 10566-10571 (2001).
16. F. T. Landgraf, C. Forreiter, A. H. Pico, T. Lamparter, J. Hughes, *FEBS Lett.* 508, 459-462 (2001).
17. Materials and Methods are available as supporting materials.
18. J. N. Maloof et al., *Nat Genet* 29, 441-446 (2001).
19. J. W. Reed, A. Nagatani, T. D. Elich, M. Fagan, J. Chory, *Plant Physiol.* 104, 1139-1149 (April 1994).
20. M. Chen, R. Schwabb, J. Chory, *Proc. Natl. Acad. Sci. USA* 100, 14493-14498 (Nov. 25, 2003).
21. J. T. Murphy, J. C. Lagarias, *Curr. Biol.* 7, 870-876 (1997).
22. FootnoteG, (2004).
23. T. Lamparter, B. Esteban, J. Hughes, *Eur. J. Biochem.* 268, 4720-4730 (2001).
24. L. Li, J. C. Lagarias, *J. Biol. Chem.* 267, 19204-19210 (Sep. 25, 1992).
25. S. H. Bhoo, S. J. Davis, J. Walker, B. Karniol, R. D. Vierstra, *Nature* 414, 776-779 (2001).
26. J. Zhang, R. E. Campbell, A. Y. Ting, R. Y. Tsien, *Nat Rev Mol Cell Biol* 3, 906-918 (2002).
27. M. V. Matz, K. A. Lukyanov, S. A. Lukyanov, *Bioessays* 24, 952-959 (2002).
28. S. P. A. Fodor, J. C. Lagarias, R. A. Mathies, *Biochem.* 29, 11141-11146 (Dec. 18, 1990).
29. A. Remberg et al., *Biochem.* 36, 13389-13395 (1997).
30. F. Andel, J. C. Lagarias, R. A. Mathies, *Biochem.* 35, 15997-16008 (1996).
31. F. Andel et al., *Biochem.* 39, 2667-2676 (2000).

Example 3

Isolation and Characterization of a Red and Near Infrared Fluorescent Phytochrome RubyRed-1 (a.k.a. Phytofluor Red 1)

As described above, we identified a red fluorescent cyanobacterial phytochrome 1 (Cph1) mutant Ruby Red 1 using flow cytometry, that we later named Phytofluor Red 1 or PR1 (see also Fischer and Lagarias (2004) [1]). We showed that the intense red fluorescence of the PCB adduct of PR1 was due to mutation of a single conserved tyrosine residue, i.e. tyrosine 176, to a histidine residue in the P3GAF bilin lyase domain of the 514 amino acid Cph1 polypeptide.

In this example, we show that introduction of the Y176H mutation into 1) into a more truncated Cph1 consisting of the N-terminal 350 amino acids (Cph1_P2P3), 2) into full length Cph1 constructs, and 3) into a truncated *Arabidopsis* phytochrome A (atPHYA:N599; Y242H) all yield red fluorescent PCB adducts. We also show that substitution of the PCB prosthetic group with the plant phytochrome PB prosthetic group produces a fluorescent adduct of Cph1 with red-shifted fluorescence excitation/emission maxima. Other site-directed mutations were also introduced at residue Y176 in the Cph1construct, i.e. Y176A, Y176C, Y176E, Y176F, Y176Q, Y176S and Y176W. All of these mutations profoundly alter the spectroscopic properties of the resulting PCB adduct, supporting the conclusion that tyrosine 176 (or the corresponding tyrosine residue in the P3GAF bilin lyase domain of other phytochromes; see alignment in Wu and Lagarias [2]) directly participates in the primary photochemistry of all phytochromes.

Methods

Phytochrome Expression Plasmids.

The cyanobacterial phytochrome 1 (Cph1) construct pBAD_Cph1_N514his was that previously described [3]. The QuickChange Site-Directed Mutagenesis Kit (Stratagene) was used to generate site-specific mutations in Cph1. The plasmid pBAD_Cph1_N514his was used as the DNA template along with the primer pairs shown in Table 3 to construct the following Cph1 mutants: Y176A, Y176C, Y176E, Y176H, Y176F, Y176Q, Y176S and Y176W. The truncated Cph1 plasmid pBAD_Cph1_P2P3his, consisting of the N-terminal 350 amino acids of Cph1, was constructed by PCR amplification of pBAD_Cph1_N514his plasmid using the primers NcoI_P2_F and HindIII_P3_R (see Table 3), restriction digestion with NcoI/HindIII and ligation with NcoI/HindIII-digested pBAD-myc,his vector (Invitrogen). The Y176H mutant version of the P2P3 domain plasmid, i.e. pBAD_Cph1Y176H_P2P3his, was constructed by site-directed mutagenesis of plasmid pBAD_Cph1_P2P3his using the Y176H primer pair in Table 3. Full-length histagged Cph1 clones, pBAD_Cph1_FLhis and pBAD_Cph1Y176H_FLhis, were similarly prepared by PCR amplification of the 3-end of Cph1 using pASK_Cph1_FLST [4] as a DNA template. The plasmid pBAD_Cph1Y176H_FLhis was derived from pBAD_Cph1_FLhis using the QuickChange Site-Directed Mutagenesis Kit and the Y176H primer pair in Table 3. The full-length strep-tagged Cph1Y176H mutant clone (pASK_Cph1Y176H_FLST) was constructed by sub-cloning a 1.2 kb AvrII/SacI fragment from pBAD_Cph1Y176H_N514his into the AvrII/SacI digested pASK75_Cph1_FLST vector fragment. Full-length strep-tagged Cph1Y176H mutant clone (pBAD_Cph1Y176H_FLST) was constructed by sub-cloning a 1.9 kb XhoI/HindIII fragment from pASK-Cph1Y176H_FLST into the XhoI/HindIII digested pBAD-Cph1_N514his vector fragment. The *Arabidopsis* PHYA expression plasmid pASK_atPHYA_N599ST that encodes the amino terminal 599 amino acids of *Arabidopsis* PHYA (Murphy, J. T. and Lagarias, J. C., unpublished data) was used as a DNA template to construct the Y242H mutant plasmid pASK_atPHYAY242H_N599ST by PCR mutagenesis using the primers Y242H_F and Y242H_R (Table 3). The DNA sequences of all plasmid inserts were verified by Davis Sequencing and the protein sequences are shown in Table 4.

TABLE 3

PCR primers used for construction of site-directed and deletion mutagenesis.

```
Cph1 Y176X Site-Directed Mutants
Cph1 Y176A_F: N = 36, Changes: 8.33%, GC: 50%, Tm = 75 C.           13
GACCGGGTGATGCTAGCGCGCTTTGATGAAAATAAC
Cph1 Y176A_R: N = 36, Changes: 8.33%, GC: 50%, Tm = 75 C.           14
GTTATTTTCATCAAAGCGCGCTAGCATCACCCGGTC Cph1 Y176C_F: N = 36, Changes: 2.77%, GC: 47%, Tm = 79 C.           15
GACCGGGTGATGCTATGCCGCTTTGATGAAAATAAC
Cph1 Y176C_R: N = 36, Changes: 2.77%, GC: 47%, Tm = 79 C.           16
GTTATTTTCATCAAAGCGGCATAGCATCACCCGGTC Cph1 Y176E_F: N = 36, Changes: 5.55%, GC: 44%, Tm = 75 C.           17
GACCGGGTGATGCTAGAACGCTTTGATGAAAATAAC
Cph1 Y176E_R: N = 36, Changes: 5.55%, GC: 44%, Tm = 75 C.           18
GTTATTTTCATCAAAGCGTTCTAGCATCACCCGGTC Cph1_Y176F-F: N = 39, Changes = 2.56%, GC = 49%, Tm = 82° C.        19
CCGGGTGATGCTATTTCGCTTTGATGAAAATAACCACGG
Cph1_Y176F-R: N = 36, Changes = 2.78%, GC = 50%, Tm = 80° C.        20
TTCATCAAAGCGGAATAGCATCACCCGGTCAAAGCC Cph1_Y176H-F RRmut2-Fd: N = 35, Changes = 2.86%, GC = 49%, Tm =     21
79° C.
CCGGGTGATGCTACACCGCTTTGATGAAAATAACC
Cnh1_Y176H-R RRmut2-REV: N = 34. Changes = 2.94%, GC = 56%, Tm      22
= 82° C.
CATCAAAGCGGTGTAGCATCACCCGGTCAAAGCC Cph1 Y176Q_F: N = 36, Changes: 5.55%, GC: 47%, Tm = 77 C.C          23
GACCGGGTGATGCTACAGCGCTTTGATGAAAATAAC
Cph1 Y176Q_R: N = 36, Changes: 5.55%, GC: 47%, Tm = 77 C.C          24
GTTATTTTCATCAAAGCGCTGTAGCATCACCCGGTC Cph1 Y176S_F: N = 36, Changes: 5.55%, GC: 47%, Tm = 77 C.C          25
GACCGGGTGATGCTAAGCCGCTTTGATGAAAATAAC
Cph1 Y176S_R: N = 36, Changes: 5.55%, GC: 47%, Tm = 77 C.C          26
GTTATTTCATCAAAGCGGCTTAGCATCACCCGGTC Cph1 Y176W_F: N = 39, Changes: 5.13%, GC: 51%, Tm = 80° C.          27
CCGGGTGATGCTATGGCGCTTTGATGAAAATAACCACGG
Cph1 Y176W_R: N = 36, Changes: 5.55%, GC: 53%, Tm = 79° C.          28
TTCATCAAAGCGCCATAGCATCACCCGGTCAAAGCC Cph1 Truncation Primers
NcoI, P2, F: GC = 60%, N = 30, Tm = 68° C.                          29
CATGCCATGGCCACCACCGTACAACTCAGC
HindIII, P3, R: 60%, N = 30, Tm = 68° C.                            30
CCCAAGCTTCTTCGACAAAATCCGCCGCCG AtPhyA Y242H
AtPhyA Y242H_F: N = 34, GC = 47%, Tm = 75° C.                       31
GACAGGGTGATGGCTCACAAGTTTCATGAAGATG
AtPhyA Y242H_R: N = 34, GC = 47%, Tm = 75° C.                       32
CATCTTCATGAAACTTGTGAGCCATCACCCTGTC
```

TABLE 4

Protein Sequences and Construct Information.

```
Yap110904
>Cph1_FLST748aa (+15 aa)
MATTVQLSDQSLRQLETLAIHTAHLIQPHGLVVVLQEPDLTISQISANCTGILGRSPEDLLG
RTLGEVFDSFQIDPIQSRLTAGQISSLNPSKLWARVMGDDFVIFDGVFHRNSDGLLVCELEP
AYTSDNLPFLGFYHMANAALNRLRQQANLRDFYDVIVEEVRRMTGFDRVMLYRFDENNHGDV
IAEDKRDDMEPYLGLHYPESDIPQPARRLFIHNPIRVIPDVYGVAVPLTPAVNPSTNRAVDL
TESILRSAYHCHLTYLKNMGVGASLTISLIKDGHLWGLIACHHQTPKVIPFELRKACEFFGR
VVFSNISAQEDTETFDYRVQLAEHEAVLLDKMTTAADFVEGLTNHPDRLLGLTGSQGAAICF
GEKLILVGETPDEKAVQYLLQWLENREVQDVFFTSSLSQIYPDAVNFKSVASGLLAIPIARH
NFLLWFRPEVLQTVNWGGDPNHAYEATQEDGKIELHPRQSFDLWKEIVRLQSLPWQSVEIQS
```

TABLE 4-continued

Protein Sequences and Construct Information.

```
ALALKKAIVNLILRQAEELAQLARNLERSNADLKKFAYIASHDLQEPLNQVSNYVQLLEMRY
SEALDEDAKDFIDFAVTGVSLMQTLIDDILTYAKVDTQYAQLTFTDVQEVVDKALANLKQRI
EESGAEIEVGSMPAVMADQIQLMQVFQNLIANGIKFAGDKSPKIKIWGDRQEDAWVFAVQDN
GIGIDPQFFERIFVIFQRLHTRDEYKGTGMGLAICKKIIEGHQGQIWLESNPGEGSTFYFSI
PIG NGRPAGSAWRHPQFGG (SEQ ID NO: 33)

>Cph1_FLhis748aa (+26 aa)
MATTVQLSDQSLRQLETLAIHTAHLIQPHGLVVVLQEPDLTISQISANCTGILGRSPEDLLG
RTLGEVFDSFQIDPIQSRLTAGQISSLNPSKLWARVMGDDFVIFDGVFHRNSDGLLVCELEP
AYTSDNLPFLGFYHMANAALNRLRQQANLRDFYDVIVEEVRRMTGFDRVMLYRFDENNHGDV
IAEDKRDDMEPYLGLHYPESDIPQPARRLFIHNPIRVIPDVYGVAVPLTPAVNPSTNRAVDL
TESILRSAYHCHLTYLKNMGVGASLTISLIKDGHLWGLIACHHQTPKVIPFELRKACEPFGR
VVFSNISAQEDTETFDYRVQLAEHEAVLLDKMTTAADFVEGLTNHPDRLLGLTGSQGAAICF
GEKLILVGETPDEKAVQYLLQWLENREVQDVFFTSSLSQIYPDAVNFKSVASGLLAIPIARH
NFLLWFRPEVLQTVNWGGDPNHAYEATQEDGKIELHPRQSFDLWKEIVRLQSLPWQSVEIQS
ALALKKAIVNLILRQAEELAQLARNLERSNADLKKFAYIASHDLQEPLNQVSNYVQLLEMRY
SEALDEDAKDFIDFAVTGVSLMQTLIDDILTYAKVDTQYAQLTFTDVQEVVDKALANLKQRI
EESGAEIEVGSMPAVMADQIQLMQVFQNLIANGIKFAGDKSPKIKIWGDRQEDAWVFAVQDN
GIGIDPQFFERIFVIFQRLHTRDEYKGTGMGLAICKKIIEGHQGQIWLESNPGEGSTFYFSI
PIG NGRSFLEQKLISEEDLNSAVDHHHHHH (SEQ ID NO: 34)

>Cph1Y176H_FLST748aa (+15 aa)
AbbyYapMATTVQLSDQSLRQLETLAIHTAHLIQPHGLVVVLQEPDLTISQISANCTGILGR
SPEDLLGRTLGEVFDSFQIDPIQSRLTAGQISSLNPSKLWARVMGDDFVIFDGVFHRNSDGL
LVCELEPAYTSDNLPFLGFYHMANAALNRLRQQANLRDFYDVIVEEVRRMTGFDRVMLHRFD
ENNHGDVIAEDKRDDMEPYLGLHYPESDIPQPARRLFIHNPIRVIPDVYGVAVPLTPAVNPS
TNRAVDLTESILRSAYHCHLTYLKNMGVGASLTISLIKDGHLWGLIACHHQTPKVIPFELRK
ACEFFGRVVFSNISAQEDTETFDYRVQLAEHEAVLLDKMTTAADFVEGLTNHPDRLLGLTGS
QGAAICFGEKLILVGETPDEKAVQYLLQWLENREVQDVFFTSSLSQIYPDAVNFKSVASGLL
AIPIARHNFLLWFRPEVLQTVNWGGDPNHAYEATQEDGKIELHPRQSFDLWKEIVRLQSLPW
QSVEIQSALALKKAIVNLILRQAEELAQLARNLERSNADLKKFAYIASHDLQEPLNQVSNYV
QLLEMRYSEALDEDAKDFIDFAVTGVSLMQTLIDDILTYAKVDTQYAQLTFTDVQEVVDKAL
ANLKQRIEESGAEIEVGSMPAVMADQIQLMQVFQNLIANGIKFAGDKSPKIKIWGDRQEDAW
VFAVQDNGIGIDPQFFERIFVIFQRLHTRDEYKGTGMGLAICKKIIEGHQGQIWLESNPGEG
STFYFSIPIG NGRPAGSAWRHPQFGG (SEQ ID NO: 35)

Figure 23A:
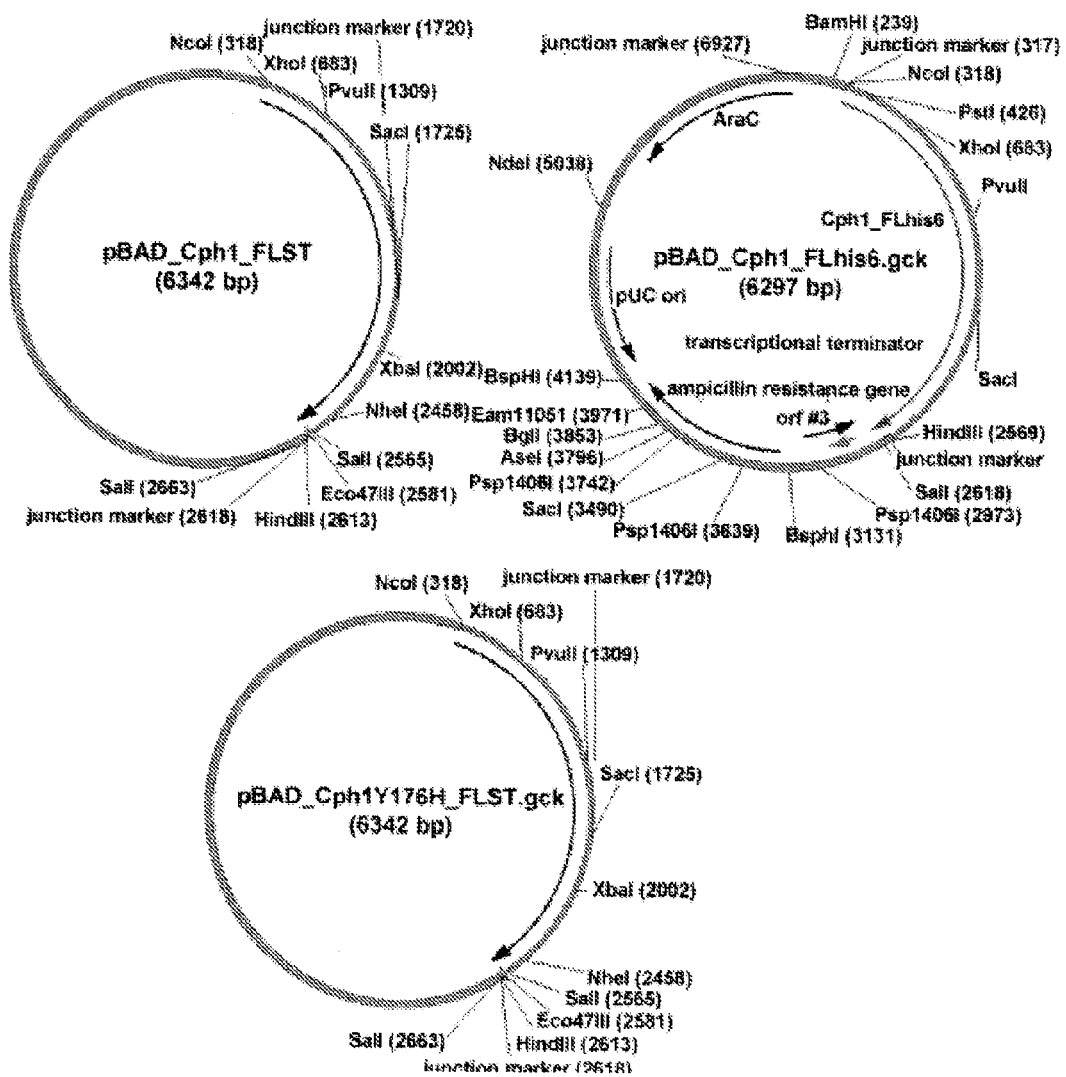
FIGS. 23A-23D show plasmid constructs encoding CPH1 mutants.

See plasmids in FIG. 23A.

>Cph1_N514 (Cph1 = P2P3P4) 514 aa (+25 aa)
MATTVQLSDQSLRQLETLAIHTAHLIQPHGLVVVLQEPDLTISQISANCTGILGRSPEDLLG
RTLGEVFDSFQIDPIQSRLTAGQISSLNPSKLWARVMGDDFVIFDGVFHRNSDGLLVCELEP
AYTSDNLPFLGFYHMANAALNRLRQQANLRDFYDVIVEEVRRMTGFDRVMLYRFDENNHGDV
IAEDKRDDMEPYLGLHYPESDIPQPARRLFIHNPIRVIPDVYGVAVPLTPAVNPSTNRAVDL
TESILRSAYHCHLTYLKNMGVGASLTISLIKDGHLWGLIACHHQTPKVIPFELRKACEFFGR
VVFSNISAQEDTETFDYRVQLAEHEAVLLDKMTTAADFVEGLTNHPDRLLGLTGSQGAAICF
GEKLILVGETPDEKAVQYLLQWLENREVQDVFFTSSLSQIYPDAVNFKSVASGLLAIPIARH
NFLLWFRPEVLQTVNWGGDPNHAYEATQEDGKIELHPRQSFDLWKEIVRLQSLPWQSVEIQS
AL ALKKAIVNLILRQAEEQAYVEQKLISEEDLNSAVDHHHHHH (SEQ ID NO: 36)

>Cph1Y176H_N514his 514 aa (+25 aa)
MATTVQLSDQSLRQLETLAIHTAHLIQPHGLVVVLQEPDLTISQISANCTGILGRSPEDL
LGRTLGEVFDSFQIDPIQSRLTAGQISSLNPSKLWARVMGDDFVIFDGVFHRNSDGLLVCELEPA
YTSDNLPFLGFYHMANAALNRLRQQANLRDFYDVIVEEVRRMTGFDRVMLHRFDENNHGDVIAEDKRD
DMEPYLGLHYPESDIPQPARRLFIHNPIRVIPDVYGVAVPLTPAVNPSTNRAVDLTESILRSAYHCHL
TYLKNMGVGASLTISLIKDGHLWGLIACHHQTPKVIPFELRKACEFFGRVVFSNISAQEDTETFDYRV
QLAEHEAVLLDKMTTAADFVEGLTNHPDRLLGLTGSQGAAICFGEKLILVGETPDEKAVQYLLQWLEN
REVQDVFFTSSLSQIYPDAVNFKSVASGLLAIPIARHNFLLWFRPEVLQTVNWGGDPNHAYEATQEDG
KIELHPRQSFDLWKEIVRLQSLPWQSVEIQSALALKKAIVNLILRQAEEQAYVEQKLISEEDLNSAVD
HHHHHH (SEQ ID NO: 37)

Figure 23B:
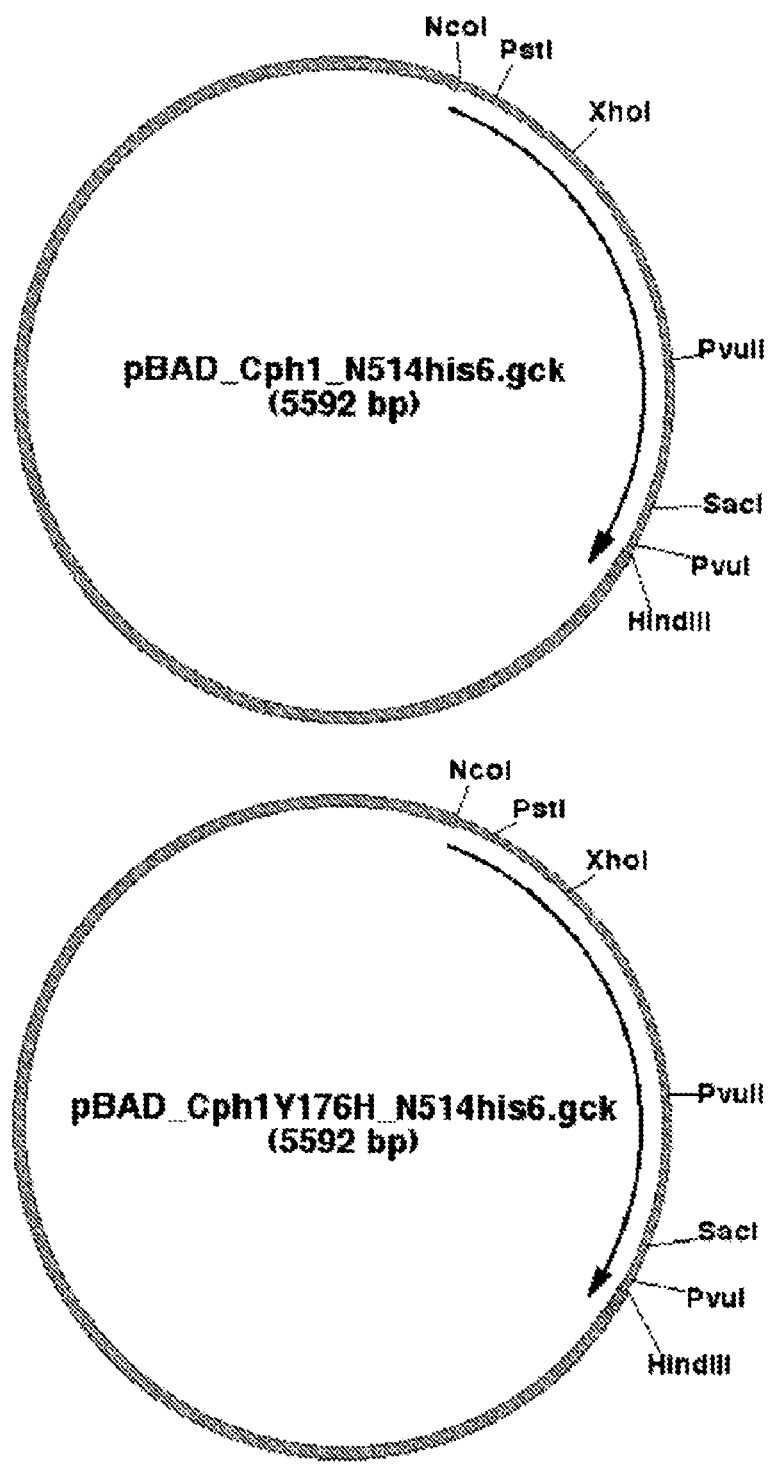

See plasmids in FIG. 23B.

>Cph1_P2P3his 350 aa (+25 aa)
MATTVQLSDQSLRQLETLAIHTAHLIQPHGLVVVLQEPDLTISQISANCTGILGRSPEDLLGRTLGEV
FDSFQIDPIQSRLTAGQISSLNPSKLWARVMGDDFVIFDGVFHRNSDGLLVCELEPAYTSDNLPFLGF
YHMANAALNRLRQQANLRDFYDVIVEEVRRMTGFDRVMLYRFDENNHGDVIAEDKRDDMEPYLGLHYP
ESDIPQPARRLFIHNPIRVIPDVYGVAVPLTPAVNPSTNRAVDLTESILRSAYHCHLTYLKNMGVGAS
LTISLTKDGHLWGLIACHHQTPKVIPFELRKACEFFGRVVFSNISAQEDTETFDYRVQLAEHEAVLLD
KMTTAADFVEEAYVEQKLISEEDLNSAVDHHHHHH (SEQ ID NO: 38)

>Cph1Y176H_P2P3his 350 aa (+25 aa)
MATTVQLSDQSLRQLETLAIHTAHLIQPHGLVVVLQEPDLTISQISANCTGILGRSPEDLLGRTLGEV
FDSFQIDPIQSRLTAGQISSLNPSKLWARVMGDDFVIFDGVFHRNSDGLLVCELEPAYTSDNLPFLGF
YHMANAALNRLRQQANLRDFYDVIVEEVRRMTGFDRVMLHRFDENNHGDVIAEDKRDDMEPYLGLHYP
ESDIPQPARRLFIHNPIRVIPDVYGVAVPLTPAVNPSTNRAVDLTESILRSAYHCHLTYLKNMGVGAS
LTISLIKDGHLWGLIACHHQTPKVIPFELRKACEFFGRVVFSNISAQEDTETFDYRVQLAEHEAVLLD
KMTTAADFVEEAYVEQKLISEEDLNSAVDHHHHHH (SEQ ID NO: 39)
```

TABLE 4-continued

Protein Sequences and Construct Information.

Figure 23C:
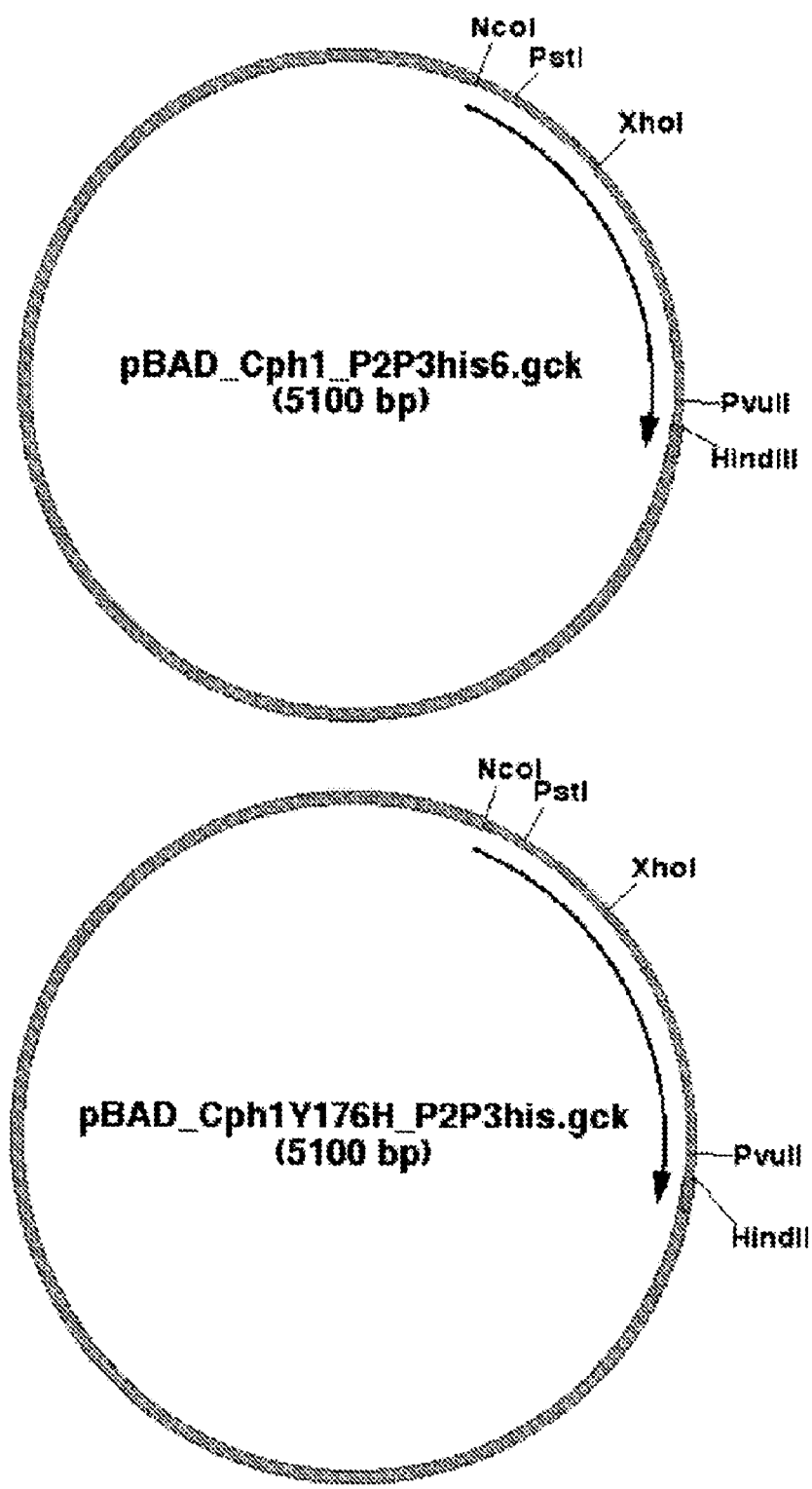

See plasmids in FIG. 23C.

>Cph1_P3P4his 364 aa (+26 aa)
MANLRDFYDVIVEEVRRMTGFDRVMLYRFDENNHGDVIAEDKRDDMEPYLGLHYPESDIPQPARRLFI
HNPIRVIPDVYGVAVPLTPAVNPSTNRAVDLTESILRSAYHCHLTYLKNMGVGASLTISLIKDGHLWG
LIACHHQTPKVIPFELRKACEFGRVVFSNISAQEDTETFDYRVQLAEHEAVLLDKMTTAADFVEGLT
NHPDRLLGLTGSQGAAICFGEKLILVGETPDEKAVQYLLQWLENREVQDVFFTSSLSQIYPDAVNFKS
VASGLLAIPIARHNFLLWFRPEVLQTVNWGGDPNHAYEATQEDGKIELHPRQSFDLWKEIVRLQSLPW
QSVEIQSALALKKAIVNLILRQAEEQAYVEQKLISEEDLNSAVDHHHHHH (SEQ ID NO: 40)

>Cph1_P3his 200 aa (+26 aa)
MANLRDFYDVIVEEVRRMTGFDRVMLYRFDENNHGDVIAEDKRDDMEPYLGLHYPESDIPQPA
RRLFIHNPIRVIPDVYGVAVPLTPAVNPSTNRAVDLTESILRSAYHCHLTYLKNMGVGASLTI
SLIKDGHLWGLIACHHQTPKVIPFELRKACEFFGRVVFSNISAQEDTETFDYRVQLAEHEAV
LLDKMTTAADFVEEAYVEQKLISEEDLNSAVDHHHHHH (SEQ ID NO: 41)

Figure 23D:
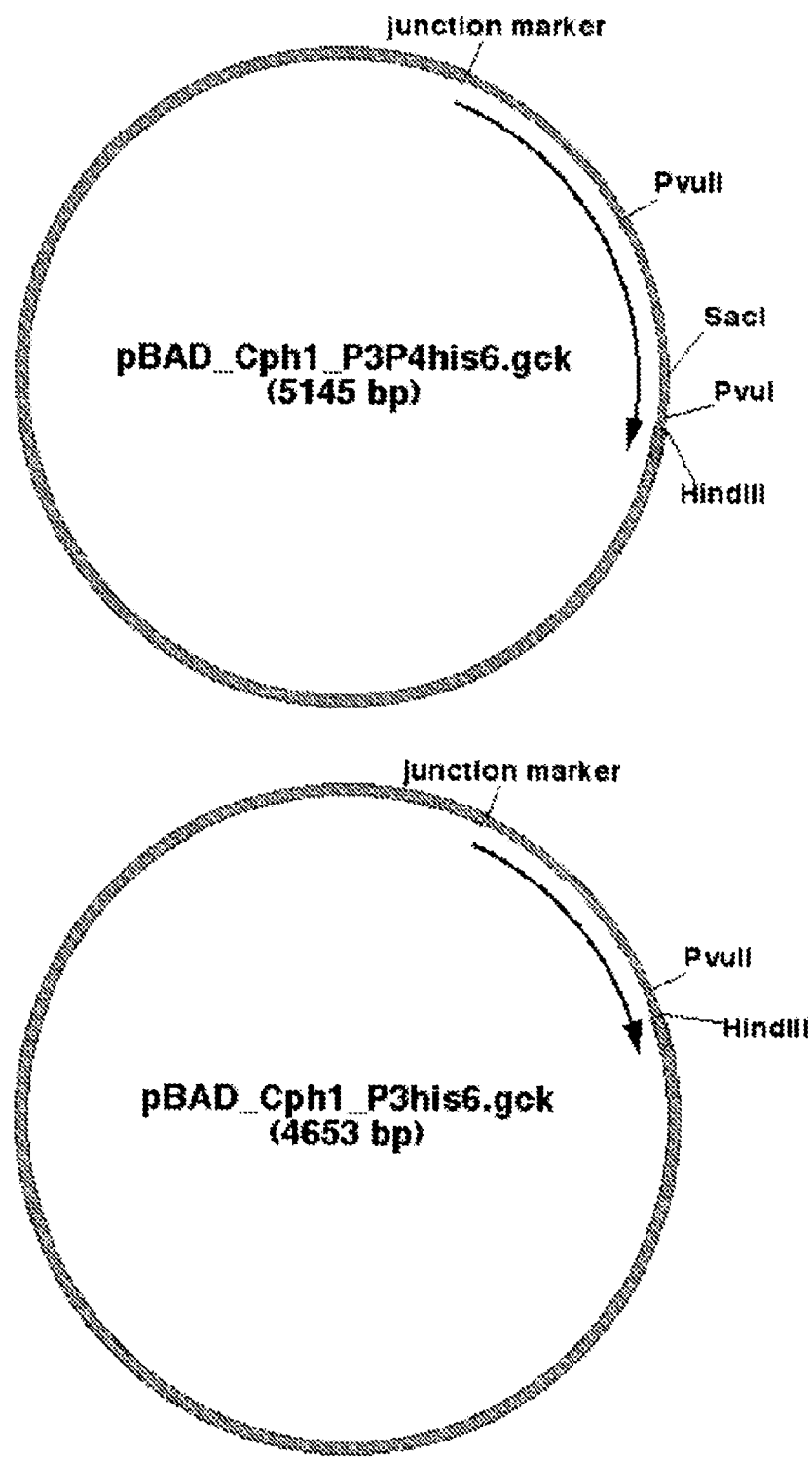

See plasmids in FIG. 23D.

Site Directed Cph1 (N514) Mutants
>Cph1Y176H_N514his 514 aa (+25 aa)
MATTVQLSDQSLRQLETLAIHTAHLIQPHGLVVVLQEPDLTISQISANCTGILGRSPEDLLG
RTLGEVFDSFQIDPIQSRLTAGQISSLNPSKLWARVMGDDFVIFDGVFHRNSDGLLVCELEP
AYTSDNLPFLGFYHMANAALNRLRQQANLRDFYDVIVEEVRRMTGFDRVMLHRFDENNHGDV
IAEDKRDDMEPYLGLHYPESDIPQPARRLFIHNPIRVIPDVYGVAVPLTPAVNPSTNRAVDL
TESILRSAYHCHLTYLKNMGVGASLTISLIKDGHLWGLIACHHQTPKVIPFELRKACEFFGR
VVFSNISAQEDTETFDYRVQLAEHEAVLLDKMTTAADFVEGLTNHPDRLLGLTGSQGAAICF
GEKLILVGETPDEKAVQYLLQWLENREVQDVFFTSSLSQIYPDAVNFKSVASGLLAIPIARH
NFLLWFRPEVLQTVNWGGDPNHAYEATQEDGKIELHPRQSFDLWKEIVRLQSLPWQSVEIQS
AL ALKKAIVNLILRQAEEQAYVEQKLISEEDLNSAVDHHHHHH (SEQ ID NO: 42)

>Cph1Y176A_N514his 514 aa (+25 aa)
MATTVQLSDQSLRQLETLAIHTAHLIQPHGLVVVLQEPDLTISQISANCTGILGRSPEDLLG
RTLGEVFDSFQIDPIQSRLTAGQISSLNPSKLWARVMGDDFVIFDGVFHRNSDGLLVCELEP
AYTSDNLPFLGFYHMANAALNRLRQQANLRDFYDVIVEEVRRMTGFDRVMLARFDENNHGDV
IAEDKRDDMEPYLGLHYPESDIPQPARRLFIHNPIRVIPDVYGVAVPLTPAVNPSTNRAVDL
TESILRSAYHCHLTYLKNMGVGASLTISLIKDGHLWGLIACHHQTPKVIPFELRKACEFFGR
VVFSNISAQEDTETFDYRVQLAEHEAVLLDKMTTAADFVEGLTNHPDRLLGLTGSQGAAICF
GEKLILVGETPDEKAVQYLLQWLENREVQDVFFTSSLSQIYPDAVNFKSVASGLLAIPIARH
NFLLWFRPEVLQTVNWGGDPNHAYEATQEDGKIELHPRQSFDLWKEIVRLQSLPWQSVEIQS
AL ALKKAIVNLILRQAEEQAYVEQKLISEEDLNSAVDHHHHHH (SEQ ID NO: 43)

>Cph1Y176C_N514his 514 aa (+25 aa)
MATTVQLSDQSLRQLETLAIHTAHLIQPHGLVVVLQEPDLTISQISANCTGILGRSPEDLLG
RTLGEVFDSFQIDPIQSRLTAGQISSLNPSKLWARVMGDDFVIFDGVFHRNSDGLLVCELEP
AYTSDNLPFLGFYHMANAALNRLRQQANLRDFYDVIVEEVRRMTGFDRVMLCRFDENNHGDV
IAEDKRDDMEPYLGLHYPESDIPQPARRLFIHNPIRVIPDVYGVAVPLTPAVNPSTNRAVDL
TESILRSAYHCHLTYLKNMGVGASLTISLIKDGHLWGLIACHHQTPKVIPFELRKACEFFGR
VVFSNISAQEDTETFDYRVQLAEHEAVLLDKMTTAADFVEGLTNHPDRLLGLTGSQGAAICF
GEKLILVGETPDEKAVQYLLQWLENREVQDVFFTSSLSQIYPDAVNFKSVASGLLAIPIARH
NFLLWFRPEVLQTVNWGGDPNHAYEATQEDGKIELHPRQSFDLWKEIVRLQSLPWQSVEIQS
AL ALKKAIVNLILRQAEEQAYVEQKLISEEDLNSAVDHHHHHH (SEQ ID NO: 44)

>Cph1Y176E_N514his 514 aa (+25 aa)
MATTVQLSDQSLRQLETLAIHTAHLIQPHGLVVVLQEPDLTISQISANCTGILGRSPEDLLG
RTLGEVFDSFQIDPIQSRLTAGQISSLNPSKLWARVMGDDFVIFDGVFHRNSDGLLVCELEP
AYTSDNLPFLGFYHMANAALNRLRQQANLRDFYDVIVEEVRRMTGFDRVMLERFDENNHGDV
IAEDKRDDMEPYLGLHYPESDIPQPARRLFIHNPIRVIPDVYGVAVPLTPAVNPSTNRAVDL
TESILRSAYHCHLTYLKNMGVGASLTISLIKDGHLWGLIACHHQTPKVIPFELRKACEFFGR
VVFSNISAQEDTETFDYRVQLAEHEAVLLDKMTTAADFVEGLTNHPDRLLGLTGSQGAAICF
GEKLILVGETPDEKAVQYLLQWLENREVQDVFFTSSLSQIYPDAVNFKSVASGLLAIPIARH
NFLLWFRPEVLQTVNWGGDPNHAYEATQEDGKIELRPRQSFDLWKEIVRLQSLPWQSVEIQS
ALALKKAIVNLILRQAEEQAYVEQKLISEEDLNSAVDHHHHHH (SEQ ID NO: 45)

>Cph1Y176F_N514his 514 aa (+25 aa) Abby Yap
MATTVQLSDQSLRQLETLAIHTAHLIQPHGLVVVLQEPDLTISQISANCTGILGRSPEDLLG
RTLGEVFDSFQIDPIQSRLTAGQISSLNPSKLWARVMGDDFVIFDGVFHRNSDGLLVCELEP
AYTSDNLPFLGFYHMANAALNRLRQQANLRDFYDVIVEEVRRMTGFDRVMLFRFDENNHGDV
IAEDKRDDMEPYLGLHYPESDIPQPARRLFIHNPIRVIPDVYGVAVPLTPAVNPSTNRAVDL
TESILRSAYHCHLTYLKNMGVGASLTISLIKDGHLWGLIACHHQTPKVIPFELRKACEFFGR
VVFSNISAQEDTETFDYRVQLAEHEAVLLDKMTTAADFVEGLTNHPDRLLGLTGSQGAAICF
GEKLILVGETPDEKAVQYLLQWLENREVQDVFFTSSLSQIYPDAVNFKSVASGLLAIPIARH
NFLLWFRPEVLQTVNWGGDPNHAYEATQEDGKIELHPRQSFDLWKEIVRLQSLPWQSVEIQS
ALALKKAIVNLILRQAEEQAYVEQKLISEEDLNSAVDHHHHHH (SEQ ID NO: 46)

>Cph1Y176Q_N514his 514 aa (+25 aa)
MATTVQLSDQSLRQLETLAIHTAHLIQPHGLVVVLQEPDLTISQISANCTGILGRSPEDLLG
RTLGEVFDSFQIDPIQSRLTAGQISSLNPSKLWARVMGDDFVIFDGVFHRNSDGLLVCELEP

TABLE 4-continued

Protein Sequences and Construct Information.

```
AYTSDNLPFLGFYHMANAALNRLRQQANLRDFYDVIVEEVRRMTGFDRVMLQRFDENNHGDV
IAEDKRDDMEPYLGLHYPESDIPQPARRLFIHNPIRVIPDVYGVAVPLTPAVNPSTNRAVDL
TESILRSAYHCHLTYLKNMGVGASLTISLIKDGHLWGLIACHHQTPKVIPFELRKACEFFGR
VVFSNISAQEDTETFDYRVQLAEHEAVLLDKMTTAADFVEGLTNHPDRLLGLTGSQGAAICF
GEKLILVGETPDEKAVQYLLQWLENREVQDVFFTSSLSQIYPDAVNFKSVASGLLATPIARH
NFLLWFRPEVLQTVNWGGDPNHAYEATQEDGKIELHPRQSFDLWKEIVRLQSLPWQSVEIQS
ALALKKAIVNLILRQAEEQAYVEQKLISEEDLNSAVDHHHHHH (SEQ ID NO: 47)

>Cph1Y176S_N514his 514 aa (+25 aa)
MATTVQLSDQSLRQLETLAIHTAHLIQPHGLVVVLQEPDLTISQISANCTGILGRSPEDLLG
RTLGEVFDSFQIDPIQSRLTAGQISSLNPSKLWARVMGDDFVIFDGVFHRNSDGLLVCELEP
AYTSDNLPFLGFYHMANAALNRLRQQANLRDFYDVIVEEVRRMTGFDRVMLSRFDENNHGDV
IAEDKRDDMEPYLGLHYPESDIPQPARRLFIHNPIRVIPDVYGVAVPLTPAVNPSTNRAVDL
TESILRSAYHCHLTYLKNMGVGASLTISLIKDGHLWGLIACHHQTPKVIPFELRKACEFFGR
VVFSNISAQEDTETFDYRVQLAEHEAVLLDKMTTAADFVEGLTNHPDRLLGLTGSQGAAICF
GEKLILVGETPDEKAVQYLLQWLENREVQDVFFTSSLSQIYPDAVNFKSVASGLLAIPIARH
NFLLWFRPEVLQTVNWGGDPNHAYEATQEDGKIELHPRQSFDLWKEIVRLQSLPWQSVEIQS
ALALKKAIVNLILRQAEEQAYVEQKLISEEDLNSAVDHHHHHH (SEQ ID NO: 48)

>Cph1Y176W_N514his 514 aa (+25 aa) Abby Yap
MATTVQLSDQSLRQLETLAIHTAHLIQPHGLVVVLQEPDLTISQISANCTGILGRSPEDLLG
RTLGEVFDSFQIDPIQSRLTAGQISSLNPSKLWARVMGDDFVIFDGVFHRNSDGLLVCELEP
AYTSDNLPFLGFYHMANAALNRLRQQANLRDFYDVIVEEVRRMTGFDRVMLWRFDENNHGDV
IAEDKRDDMEPYLGLHYPESDIPQPARRLFIHNPIRVIPDVYGVAVPLTPAVNPSTNRAVDL
TESILRSAYHCHLTYLKNMGVGASLTISLIKDGHLWGLIACHHQTPKVIPFELRKACEFFGR
VVFSNISAQEDTETFDYRVQLAEHEAVLLDKMTTAADFVEGLTNHPDRLLGLTGSQGAAICF
GEKLILVGETPDEKAVQYLLQWLENREVQDVFFTSSLSQIYPDAVNFKSVASGLLAIPIARH
NFLLWFRPEVLQTVNWGGDPNHAYEATQEDGKIELHPRQSFDLWKEIVRLQSLPWQSVEIQS
ALALKKAIVNLILRQAEEQAYVEQKLISEEDLNSAVDHHHHHH (SEQ ID NO: 49)
```

Bilin Biosynthetic Vector Constructs.

The phycocyanobilin (PCB) biosynthetic plasmid pPL-PCB was previously described [3]. The pPL-PB plasmid contains a synthetic operon consisting of Synechocystis heme oxygenase (HO 1; Cyanobase Locus sl11184) and Arabidopsis phytochromobilin synthase (HY2) coding regions [5, 6]. pPL-PB was produced by initially cloning a GST-fusion of HY2 into plasmid pCR2.1/HO1-RBS [3] to produce plasmid pCR2.1/HO1-RBS-GSTmHY2. Arabidopsis HY2 cDNA was PCR-amplified using plasmid DNA template pGEX-GSTmHY2 and sense primer mHY2-EcoRV, 5'-CGG ATA TCA TGT CCC CTA TAC TA-3' (SEQ ID NO:50) and antisense primer mHY2-NotI 5'-GCG CGG CCG CTT AGC CGA TAA ATT GTC C-3' (SEQ ID NO:51). pGEX-GST-mHY2 encodes a GST-fusion of the mature HY2 protein that lacks the stromal transit peptide. The PCR reaction was carried out using a standard reaction mix, Pfu polymerase, and a 35 cycle run with an annealing temperature of 55° C. The PCR product was restricted with EcoRV/NotI and then subcloned into the similarly restricted plasmid pCR2.1/HO1-RBS to produce the plasmid pCR2.1/HO1-RBS-GSTmHY2. Plasmid pCR2.1/HO1-RBS-GSTmHY2 was restricted with KpnI/NotI and the resulting fragment was ligated into KpnI/NotI-restricted pPROLarA122 (Clontech Laboratories) to yield pPL-PB. The red fluorescent PR1 triple mutant (pBAD_Cph1A47TY176HI252N_N514his) and PR1-derived Y176H single mutant construct (pBAD_Cph1Y176H_N514his) were those reported previously (see supra and [1]).

Phytochrome Expression and Purification.

Holophytochromes were typically produced in E. coli strain LMG194 (Invitrogen) co-transformed with two plasmids—a phytochrome expression plasmid and a bilin biosynthetic plasmid [3]. In some experiments, plasmid pPL-PB was used to produce a WT or mutant apophytochrome assembled with a phytochromobilin (PB) prosthetic group. Protein expression and purification of his-tagged Cph1s were performed as described above. Full length Cph1ST and truncated Arabidopsis phyAST preparations were spectroscopically analyzed in crude extracts from E. coli host strain DH5.

Absorption and Fluorescence Measurements.

All absorption spectra were obtained using an HP8453 ultraviolet-visible spectrophotometer as decribed previously (see Disclosure 050304). Corrected fluorescence excitation and emission spectra were obtained with an SLM Aminco Bowman AB2 fluorimeter. Monochromators were adjusted to 4 nm bandpass for all fluorescence measurements on the AB2. For comparative purposes, fluorescence measurements shown on the same graphs were performed using samples adjusted to equal absorbance at 280 nm (0.4) and equal excitation voltages were used.

SDS-PAGE and Zinc-Blot Analysis.

Protein samples were analyzed by SDS-PAGE using the Laemmli buffer system [7]. After electrophoresis, proteins were electrophoretically transferred to polyvinylidene difluoride (PVDF) membranes at 100 V for 60 minutes. The PVDF membranes were incubated in 1.3 M zinc acetate overnight at 4° C., and the fluorescence was detected using a Storm 860 Fluorimager in red fluorescence mode [8, 9].

TABLE 5

Spectroscopic Properties of Recombinant Holophytochrome WT and Mutants

| | Red/NUV max ABS Ratio | Pr Red ABS max (nm) | Pr NUV ABS max (nm) | A max (nm)/min (nm) | A/A(Pr max) Ratio | ex. Max (nm) | em Max (nm) | Relative Emission Intensity |
|---|---|---|---|---|---|---|---|---|
| PCB Adducts | | | | | | | | |
| Cph1 P2/P3 WT his | 2.14 | 650 | 358 | 649/694 | 0.28 | Weak | 672 | |
| Cph1 P2/P3 Y176H his | 2.56 | 646 | 355 | 648/689 | 0.022 | 356/647 | 674 | |
| AtN599 WT ST | n.d. | 651 | n.d. | 649/711 | 0.43 | n.d. | n.d. | |
| AtN599 Y242H ST | n.d. | 638 | n.d. | (638/704) | 0.036 | 398/650 | 673 | |
| Cph1 FL WT his | 1.5 | 663 | 357 | 657/704 | 0.71 | 395/650 | 676 | |
| Cph1 FL Y176H his | n.d. | 644 | n.d. | 647/696 | 0.050 | 357/647 | 669 | |
| Cph1 FL WT ST | n.d. | 667 | n.d. | n.d./707 | n.d. | 408/652 | 681 | |
| Cph1 FL Y176H ST | n.d. | n.d. | n.d. | none | n.d. | 370/646 | 674 | |
| Cph1 WT his | 2.9-3.5 | 661-662 | 363 | 658-9/704-5 | 0.76 | 652 | 672 weak | 8.6 |
| Cph1 Y176H his | 2.5-2.7 | 645 | 355 | 642-4/688- | 0.067 | 353- | 668 | 134 |
| Cph1 Y176W his | 0.98 | 645 | 357 | none | n.d. | 360/652 | 678 | 115 |
| Cph1 Y176F his | 0.53 | 599 | 363 | 658/712 | 0.037 | 361/647 | 686 | 38.5 |
| Cph1 Y176Q his | 2.5 | 656 | 357 | 656/698 | 0.056 | 357/657 | 681 | 150.5 |
| Cph1 Y176C his | 1.1 | 646 | 366 | 650/693 | 0.14 | 355/646 | 672 | 38.1 |
| Cph1 Y176A his | 0.7 | 641 | 367 | 650/699 | 0.20 | 354/646 | 673 | 33 |
| Cph1 Y176E his | 1.3 | 662 | 352 | 656/701 | 0.088 | 362/659 | 683 | 83 |
| Cph1 Y176S his | n.d. | 645 | n.d. | 644/698 | 0.41 | 641 | 673 | 38 |
| PB Adducts | | | | | | | | |
| Cph1 WT his | 1.25 | 674 | 380 | 675/721 | 0.50 | 652 | n.d. | |
| Cph1 Y176H his | 1.96 | 656 | 380 | 661/701 | 0.027 | 371/652 | 682 | |

Results & Discussion.

The P4PHY Domain of Cph1 is Unnecessary for Bilin Binding.

We previously proposed that both the P3GAF and P4PHY domains are required for maintaining the bilin prosthetic group of phytochrome in an extended conformation [2]. Deletion mutagenesis was undertaken to remove the P4PHY domain of Cph1_WT (and Cph1_Y176H mutant) to yield 42 kDa WT P2P3 (and Y176H P2P3 mutant) polypeptides that were purified from PCB-expressing cells. Both proteins were expressed in PCB-producing bacteria and the purified proteins possessed covalently bound bilin prosthetic groups as revealed by zinc blot analysis (FIG. 6A). The photochemical activity of the Y176H_P2P3 mutant was notably lower than that of WT_P2P3 (FIG. 6B), reflecting the former's enhanced fluorescence emission (FIG. 6C). The fluorescence spectrum of Cph1Y176H_P2P3 is quite similar with the Y176H mutant of Cph1 [1]. Surprisingly, the WT_P2P3 polypeptide exhibited Pr and Pfr absorption maxima nearly identical with those of Y176H_P2P3 mutant polypeptide (FIG. 6D). Compared with WT_Cph1 however, the photochemical activity of Cph1WT_P2P3 was considerably reduced (FIG. 6D). These data indicate that the 'complete' bilin binding pocket is present in the truncated Cph1_P2P3 domain fragment, and supports the hypothesis that the P4 domain 'tunes' the bilin's spectral properties. Along with previous results [2], these data indicate that the bilin prosthetic group of Cph1 is entirely contained within its P3GAF domain. Photochemically active and/or fluorescent phytochromes as small as 200 residues in length (i.e. the size of a GFP monomer) that comprise a single bilin-binding GAF domain thus appear to be feasible to make.

Tyrosine 176 is Critical for the Photochemistry of Plant Phytochromes.

To test the role of the conserved tyrosine residue in the photochemical activity of plant phytochromes, this residue was mutagenized to histidine in the truncated Arabidopsis phytochrome A construct atPHYA_N599ST. This Y242H mutant of atPHYA_N599ST was co-expressed with pPL-PCB and the spectroscopic properties were compared with WT atPHYA_N599ST in crude E. coli cell extracts. FIG. 7 shows that the PCB adduct of atPHYA(Y242H)_N599ST shows reduced photochemistry and enhanced fluorescence compared with the PCB adduct of WT atPHYA_N599ST. These results indicate that this conserved tyrosine residue participates in photochemical gating in this plant phytochrome, thus supporting the hypothesis that photochemical gating in all phytochromes is mediated by this conserved tyrosine residue. Similar experiments were performed using full length Arabidopsis and oat PHYA constructs, but unfortunately these proteins were poorly expressed and/or proved to be insoluble in E. coli (data not shown). Experiments with cyanobacterial phytochrome 2 (cph2) representatives and the biliverdin-binding bacteriophytochrome (BphP) family are in progress.

The Presence of the C-Terminal Regulatory Domains does not Affect the Fluorescence of the Y176H Mutant.

To ascertain whether the histidine kinase regulatory domain affects the fluorescence of the Y176H mutation in Cph1, full-length Cph1 constructs were co-expressed with pPL-PCB. While the expression of the his-tagged Y176H mutant was considerably less than that of WT, the Y176H was fluorescent and poorly photochromic (FIG. 17). Similar results were observed with the strep-tagged versions of full-length Cph1 that were more poorly expressed (data not shown). The absence/presence of the C-terminal regulatory domain therefore is not responsible for the enhanced fluorescence caused by the Y176H mutation.

Substitution of PCB with PB Red-Shifts the Fluorescent Emission from Cph1_Y176H.

Figure 18:
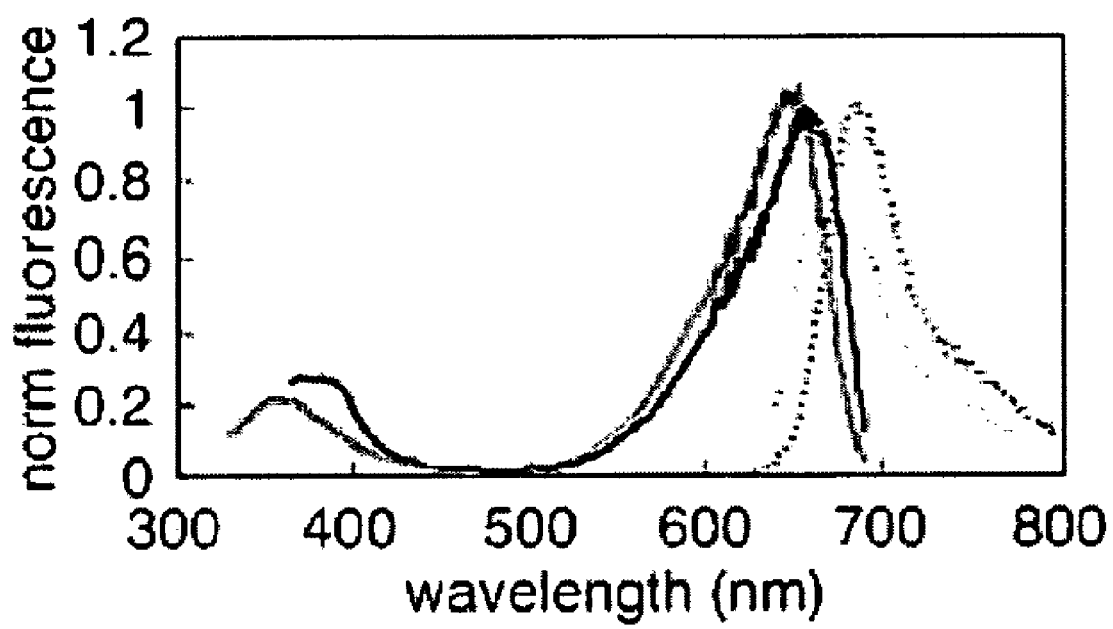
FIG. 18. Fluorescence spectra comparison of PCB and PB-adducts of Cph1_Y176Hhis. Normalized corrected fluorescence spectra of Cph1_Y176H mutant PCB (EX 648 nm/EM 671 nm; blue) and PB (EX 652 nm/EM 682 nm; red) adducts.

Expression of Cph1_Y176H_his in cells harboring the plasmid pPL-PB was show to yield a fluorescent biliprotein which was purified. For comparative purpose, the corrected fluorescence excitation/emission spectra of the PCB- and PB-adducts of Cph1_Y176H were obtained (FIG. 18). These measurements show that substitution of the different bilin chromophores into the Y176H mutant (and other apophytochrome mutants) can be used to shift the excitation/emission spectrum of the resulting phytofluor.

Comparative Spectroscopic Analysis of Cph1Y176H Mutants Reveals the Critical Role for H-Bonding of Residue 176 in Photochemical Gating.

Figure 19:
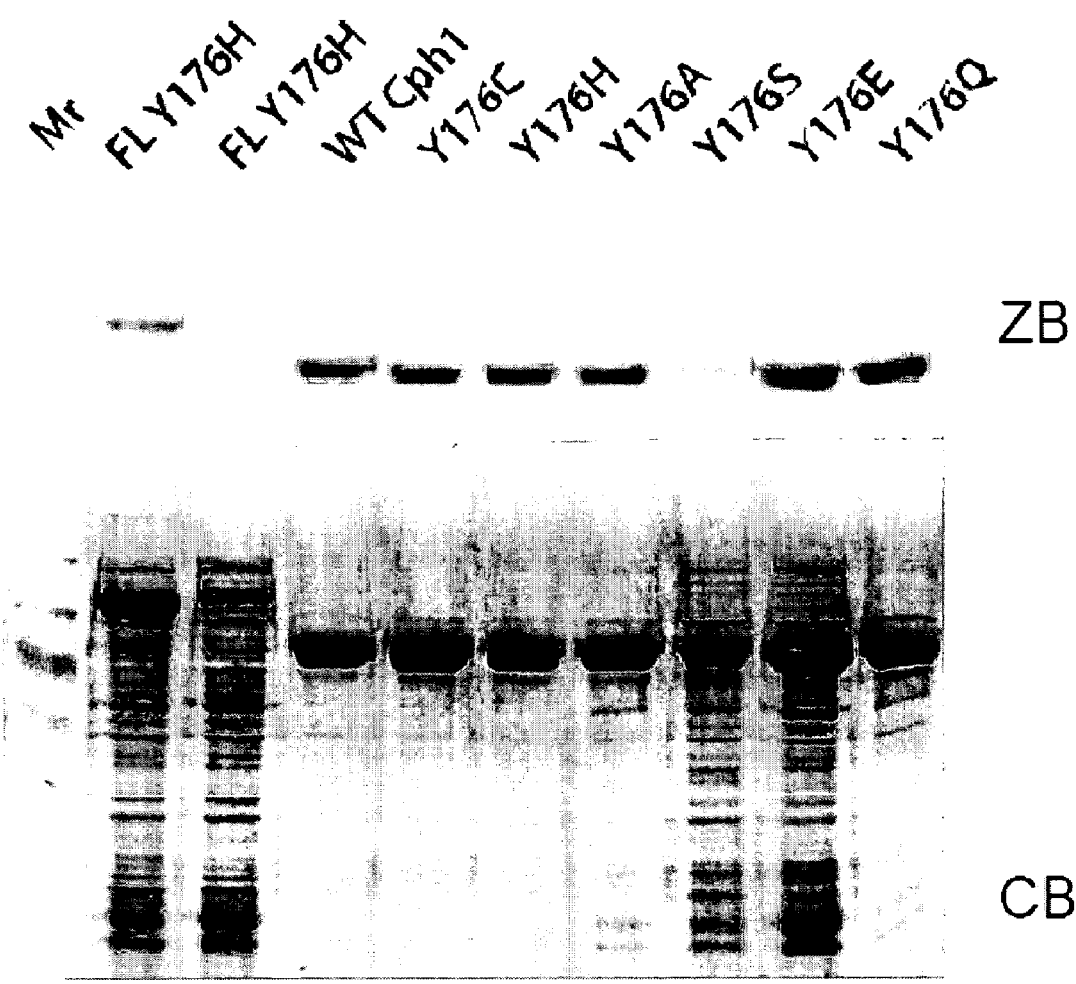
FIG. 19. SDS PAGE and zinc blot analysis of Cph1_Y176Xhis mutants. Coomassie Blue stained (bottom; CB) and zinc-blot (top; ZB) 10% SDS polyacrylamide gel analysis of purified WT and Y176X mutants for full length (FL) Cph1 and Cph1. All proteins were his-tagged. Molecular mass markers (labeled Mr) included.
Figure 20:
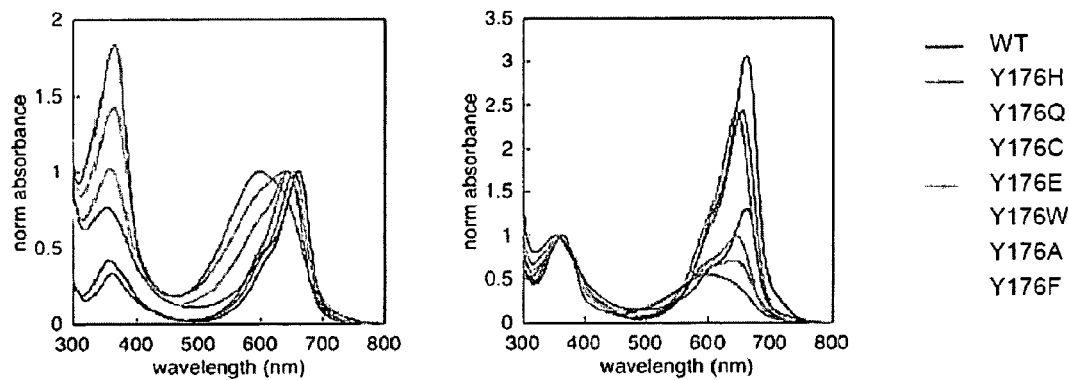
FIG. 20. Comparative absorption spectra of Cph1_Y176Xhis mutants. Normalized baseline corrected absorbance spectra of Cph1_Y176X mutants, normalized to the red (left) and blue (middle) absorption maxima. Legend is on the right. Y176S mutant data (not shown).
Figure 21:
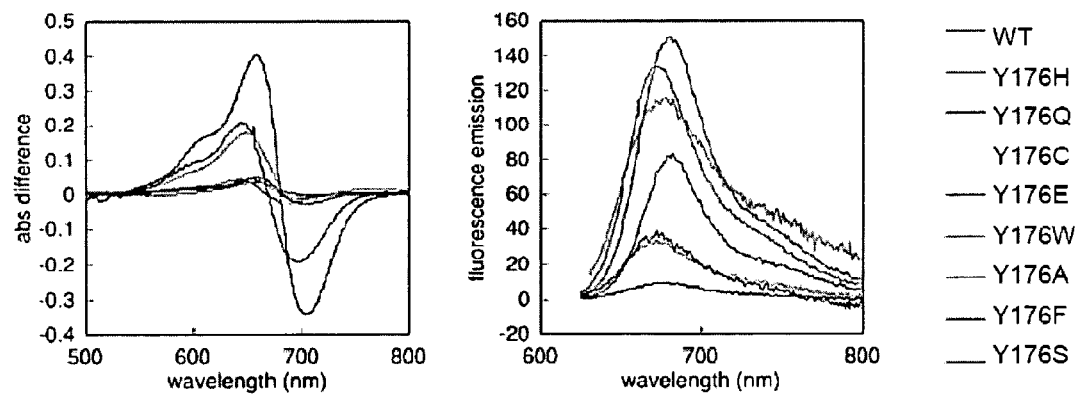
FIG. 21. Comparative phytochrome difference spectra and fluorescence emission spectra of Cph1_Y176Xhis mutants. Normalized phytochrome difference spectra and corrected fluorescence emission spectra of Cph1_Y176X mutants showing the relative fluorescence of the various mutants. Y176W mutant difference spectral data (not shown).
Figure 22:
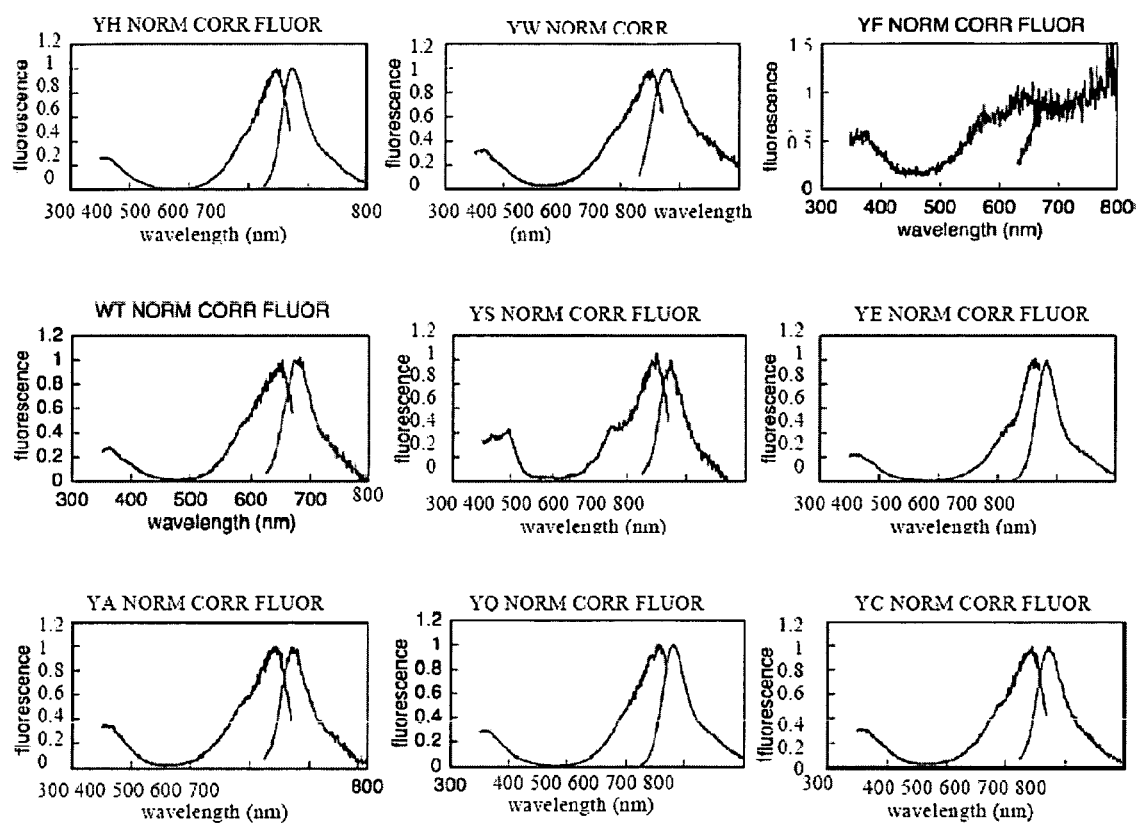
FIG. 22. Comparative fluorescence excitation and emission analysis of Cph1_Y176Xhis mutants. Normalized corrected fluorescence spectra of Cph1D_Y176X mutants.

To address the role of Y176 in Cph1's photochemistry, other site directed mutations were introduced into this position. These include replacement of Y176 with aromatic residues, i.e. Y176F and Y166W, replacement with polar H-bonding residues, i.e. Y176C, Y176E, Y176Q and Y176S, and replacement with a small nonpolar amino acid, i.e. Y176A. All of the mutants yielded covalent adducts with PCB as revealed by zinc blot analysis (FIG. 19), however the polar amino acid substitution mutants Y176S and Y176E were poorly expressed which led to difficulties for their purification and spectral characterization. As depicted in FIG. 20, all Y176X mutants exhibited spectra alterations—a result consistent with the hypothesis that Y176 plays a direct role in photochemical gating. Based on the ratio of the red to blue/nearUV absorption maxima of their Pr form ($A^R/A^{BUV}$), the Y176X mutants can be categorized into three spectral classes. This ratio reflects the conformation of the bilin prosthetic group with the largest values corresponding to more extended conformations (and largest molar absorption coefficients for their red absorption maxima) while smaller values corresponding to more cyclic, porphyrin-like conformations [10]. For reference purposes, $A^R/A^{BUV}$ for WT Cph1 was determined to be 3.0-3.5. Class I mutants possess spectra most similar to WT Cph1 with the largest $A^R/A^{BUV}$ ratio, i.e. 2.5-2.7. Members of this class include the PR1-derived Y176H mutant and the Y176Q mutant. Class II mutants Y176C, Y176E and Y176W exhibit an intermediate $A^R/A^{BUV}$ ratio, i.e. 1.0-1.3. Class III mutants Y176A and Y176F have the smallest $A^R/A^{BUV}$ ratio, i.e. 0.5-0.7, indicating that the PCB prosthetic group adopts a more cyclic conformation in these proteins. FIG. 21 shows that the photochemical interconvertibility of each Y176X mutant is inversely correlated with its fluorescence emission intensity. The photointerconvertibility of the Y176X mutants varied significantly depending on the nature of the Y176 amino acid substitution (FIG. 21, left panel). Compared with WT Cph1, the amount of photoconversion decreased in the following rank order WT>Y176A, Y176S>Y176C>Y176E, Y176F, Y176H, Y176Q and Y176W. Based on magnitude of the difference spectrum (A), we estimate the relative photoconversion efficiencies to be 100% (WT), 50% (Y176A,S), 25% (Y176C) and <10% (Y176E,F,H,Q&W). By comparison, the fluorescence emission intensities for the Y176X mutants were inversely related to their photoconversion efficiencies (FIG. 21, middle panel). The Y176Q and Y176H mutants proved to be the most intensely fluorescent followed by Y176W, Y176E and Y176A/176C/176F/Y176S. Based on integrated fluorescence emission spectra, the relative fluorescence intensities were estimated to be 100% (Y176Q & Y176H), 80% (Y176W), 50% (Y176E) and 25% (Y176A,C,F &S) and <10% WT. The absorption and fluorescence excitation of Y176Q in particular are red-shifted compared with those of Y176H, suggesting that the conformation/protonation state of its bilin prosthetic group is more similar to WT. Taken together, these results document the critical role of Y176 in WT Cph1 in gating the photochemical Pr-to-LumiR interconversion. From this data, we conclude that 1) Q and H are the most effective substitutions of Y176 to yield fluorescent PCB adducts of Cph1 with extended chromophore conformations, 2) substitution of Y176 with other large residues capable of H-bonding, i.e. W, E, yield the next most fluorescent PCB adducts, 3) H-bonding between 'fluorescent' Y176X substitutions and another protein residue (or the bilin chromophore itself) appears responsible for inhibiting Pr excited state decay via photoisomerization, 4) proton transfer to/from residue 176 does not account for the enhanced fluorescence of the Y176X mutants, 5) substitution of Y176 for non-polar amino acids, i.e. Y176A and Y176F, effected complete loss of the extended conformation of the bilin chromophore (in part) by inhibiting its protonation significantly blueshifting the long wavelength absorption maximum of the PCB adduct and 6) substitution of Y176 by other natural and non-natural amino acids can be used to further 'tune' the photophysical and spectroscopic properties of phytochromes.

REFERENCES

1. Fischer, A. J., and Lagarias, J. C. (2004). Harnessing Phytochrome's Glowing Potential. Proceedings Of The National Academy Of Sciences Of The United States Of America, in press.
2. Wu, S. H., and Lagarias, J. C. (2000). Defining the bilin lyase domain: Lessons from the extended phytochrome superfamily. Biochemistry 39, 13487-13495.
3. Gambetta, G. A., and Lagarias, J. C. (2001). Genetic engineering of phytochrome biosynthesis in bacteria. Proceedings of the National Academy of Sciences of the United States of America 98, 10566-10571.
4. Yeh, K.-C., Wu, S.-H., Murphy, J. T., and Lagarias, J. C. (1997). A cyanobacterial phytochrome two-component light sensory system. Science 277, 1505-1508.
5. Cornejo, J., Willows, R. D., and Beale, S. I. (1998). Phytobilin biosynthesis: cloning and expression of a gene encoding soluble ferredoxin-dependent heme oxygenase from *Synechocystis* sp. PCC 6803. Plant Journal 15, 99-107.
6. Kohchi, T., Mukougawa, K., Frankenberg, N., Masuda, M., Yokota, A., and Lagarias, J. C. (2001). The *Arabidopsis* HY2 gene encodes phytochromobilin synthase, a ferredoxin-dependent biliverdin reductase. The Plant Cell 13, 425-436.
7. Laemmli, U. K. (1970). Cleavage of structural proteins during the assembly of bacteriophage T4. Nature 227, 680-685.
8. Berkelman, T. R., and Lagarias, J. C. (1986). Visualization of bilin-linked peptides and proteins in polyacrylamide gels. Analytical Biochemistry 156, 194-201.
9. Li, L., and Lagarias, J. C. (1992). Phytochrome Assembly—Defining Chromophore Structural Requirements for Covalent Attachment and Photoreversibility. Journal of Biological Chemistry 267, 19204-19210.
10. Falk, H. (1989). The Chemistry of Linear Oligopyrroles and Bile Pigments. (Vienna: Springer-Verlag).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated nucleic acid encoding a phytochrome protein comprising a mutation in the P3 GAF domain, wherein said mutation is an amino acid substitution for tyrosine at the position corresponding to tyrosine 176 (Y176) in the reference cyanobacterial phytochrome 1 (Cph1) phytochrome from Synechocystis (SEQ ID NO:4), whereby the fluorescence emission of a bilin-protein adduct formed from said phytochrome protein is enhanced relative to the fluorescence emission of a bilin-protein adduct formed from the corresponding wild type phytochrome protein with the same bilin.

2. The nucleic acid of claim 1, wherein said phytochrome protein, when combined with a bilin, produces a far red and/or NIR-emitting phytofluor.

3. The nucleic acid of claim 1, wherein said nucleic acid encodes a phytochrome protein consisting of a single bilin-binding GAF domain, that when combined with a bilin produces a far red and/or NIR-emitting phytofluor.

4. The nucleic acid of claim 1, wherein said substitution is a substitution of histidine for said tyrosine.

5. The nucleic acid according to any one of claims 1 through 4, wherein said nucleic acid encodes a chimeric protein comprising a phytofluor tag.

6. The nucleic acid of claim 1, wherein said nucleic acid comprises the nucleotide sequence depicted in FIG. 1A (SEQ ID NO:1).

7. The nucleic acid of claim 1, wherein said nucleic acid consists of the nucleotide sequence depicted in FIG. 1A (SEQ ID NO:1).

8. The nucleic acid of claim 1, wherein said phytochrome protein is a cyanobacterial phytochrome protein.

9. The nucleic acid of claim 1, wherein said phytochrome protein is a plant phytochrome protein.

10. The nucleic acid of any one of claims 1, 2, 3, 4, 5, 8, and 9, wherein said nucleic acid comprises a vector.

11. A cell or cell line that expresses an apoprotein encoded by a nucleic acid according to any of claims 1-5, 6, 7, 8, and 9.

* * * * *